United States Patent
Delbeck et al.

(10) Patent No.: US 10,414,765 B2
(45) Date of Patent: Sep. 17, 2019

(54) SUBSTITUTED PERHYDROPYRROLO[3,4-C]PYRROLE DERIVATIVES AND THE USE OF SAME

(71) Applicant: BAYER PHARMA AKTIENGESELLSCHAFT, Berlin (DE)

(72) Inventors: Martina Delbeck, Heiligenhaus (DE); Michael Hahn, Langenfeld (DE); Thomas Müller, Langenfeld (DE); Heinrich Meier, Wuppertal (DE); Klemens Lustig, Wuppertal (DE); Johanna Mosig, Dortmund (DE); Luisella Toschi, Berlin (DE); Udo Albus, Florstadt (DE); Doris Gehring, Kelkheim (DE); Björn Rosenstein, Bad Soden-Salmünster (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/781,848

(22) PCT Filed: Dec. 2, 2016

(86) PCT No.: PCT/EP2016/079544
§ 371 (c)(1),
(2) Date: Jun. 6, 2018

(87) PCT Pub. No.: WO2017/097671
PCT Pub. Date: Jun. 15, 2017

(65) Prior Publication Data
US 2018/0370965 A1    Dec. 27, 2018

(30) Foreign Application Priority Data
Dec. 10, 2015  (EP) ................................... 15199268

(51) Int. Cl.
*C07D 471/04* (2006.01)
*C07D 519/00* (2006.01)
*A61P 11/00* (2006.01)
*A61K 31/437* (2006.01)
*A61K 45/06* (2006.01)

(52) U.S. Cl.
CPC .......... *C07D 471/04* (2013.01); *A61K 31/437* (2013.01); *A61K 45/06* (2013.01); *A61P 11/00* (2018.01); *C07D 519/00* (2013.01)

(58) Field of Classification Search
CPC ... C07D 471/04; C07D 519/00; A61K 31/437
See application file for complete search history.

(56) References Cited

U.S. PATENT DOCUMENTS

| | | |
|---|---|---|
| 6,833,364 B1 | 12/2004 | Straub et al. |
| 6,864,287 B1 | 3/2005 | Alonso-Alija et al. |
| 9,127,001 B2* | 9/2015 | Bialy .................... C07D 471/18 |
| 9,284,333 B2* | 3/2016 | Bialy .................... C07D 471/04 |
| 2002/0022624 A1 | 2/2002 | Dinnell et al. |
| 2002/0173514 A1 | 11/2002 | Stasch et al. |
| 2004/0082798 A1 | 4/2004 | Alonso-Alija et al. |
| 2004/0176446 A1 | 9/2004 | Alonso-Alija et al. |
| 2004/0224945 A1 | 11/2004 | Straub et al. |
| 2005/0239823 A1 | 10/2005 | Oberbörsch et al. |
| 2006/0052397 A1 | 3/2006 | Alonso-Alija et al. |
| 2006/0094769 A1 | 5/2006 | Alonso-Alija et al. |
| 2008/0058314 A1 | 3/2008 | Alonso-Alija et al. |
| 2012/0022084 A1 | 1/2012 | Follmann et al. |
| 2013/0267548 A1 | 10/2013 | Follmann et al. |
| 2014/0148433 A1 | 5/2014 | Follmann et al. |
| 2014/0350020 A1 | 11/2014 | Follmann et al. |
| 2015/0018342 A1 | 1/2015 | Bialy et al. |
| 2019/0062326 A1 | 2/2019 | Delbeck |

FOREIGN PATENT DOCUMENTS

| | | |
|---|---|---|
| EP | 1974729 A1 | 10/2008 |
| EP | 2671582 B1 | 7/2016 |
| WO | WO200006568 A1 | 2/2000 |
| WO | WO200006569 A1 | 2/2000 |
| WO | WO200119355 A2 | 3/2001 |
| WO | WO200119776 A2 | 3/2001 |
| WO | WO200119778 A1 | 3/2001 |
| WO | WO200119780 A2 | 3/2001 |
| WO | WO2002002557 A2 | 1/2002 |
| WO | WO200242301 A1 | 5/2002 |

(Continued)

OTHER PUBLICATIONS

Jungbauer, Respiroatyr Physiology & Neurobiology, vol. 245, 13-28, 2017. (Year: 2017).*

(Continued)

*Primary Examiner* — D Margaret M Seaman
(74) *Attorney, Agent, or Firm* — Morrison & Foerster LLP

(57) ABSTRACT

The present application relates to novel (2-phenylimidazo[1,2-a]pyridin-3-yl)methyl-substituted perhydropyrrolo[3,4-c]pyrrole derivatives, to methods for the preparation thereof, to the use thereof alone or in combinations for treatment and/or prevention of diseases, and to the use thereof for production of medicaments for treatment and/or prevention of diseases, especially for treatment and/or prevention of respiratory disorders including sleep-related respiratory disorders such as obstructive sleep apneas and central sleep apneas and snoring.

8 Claims, No Drawings

(56) References Cited

FOREIGN PATENT DOCUMENTS

| | | |
|---|---|---|
| WO | WO2002066478 A1 | 8/2002 |
| WO | WO200270462 | 9/2002 |
| WO | WO200270510 A2 | 9/2002 |
| WO | WO200395451 | 11/2003 |
| WO | WO200435578 A1 | 4/2004 |
| WO | WO2009143156 A3 | 1/2010 |
| WO | WO2011147809 A1 | 12/2011 |
| WO | WO2012028647 A1 | 3/2012 |
| WO | WO2012059549 A1 | 5/2012 |
| WO | WO2012004258 A9 | 6/2012 |
| WO | WO2011113606 A8 | 10/2012 |
| WO | WO2012130322 A1 | 10/2012 |
| WO | WO2013037736 A1 | 3/2013 |
| WO | WO2013037914 A1 | 3/2013 |
| WO | WO2012143796 A3 | 6/2013 |
| WO | WO2014187922 A1 | 11/2014 |
| WO | WO2015144605 A1 | 10/2015 |
| WO | WO2016084866 A1 | 6/2016 |
| WO | WO2016088813 A1 | 6/2016 |
| WO | WO2017097671 A1 | 6/2017 |
| WO | WO2017097792 A1 | 6/2017 |
| WO | WO2018015196 A1 | 1/2018 |

OTHER PUBLICATIONS

Roy, J appl Physiol, vol. 112, 212-224, 2014. (Year: 2014).*

"FLIPR Membrane Potential Assay Kits," located at https://www.moleculardevices.com/products/assay-kits/ion-channel/flipr-membrane-potential, last visited on Dec. 6, 2018, three pages.

Artursson, P. et al. (Mar. 1991). "Correlation Between Oral Drug Absorption in Humans and Apparent Drug Permeability Coefficients in Human Intestinal Epithelial (CACO-2) Cells," Biochemical and Biophysical Research Communications 175(3): 880-885.

Bayliss et al., (2015). "The role of pH-sensitive TASK channels in central respiratory chemoreception," Pflugers Arch. 467, 467:917-929.

Berg et al., (Jul. 28, 2004). "Motoneurons Express Heteromeric TWIK-Related Acid-Sensitive K+ (TASK) Channels Containing TASK-1 (KCNK3) and TASK-3 (KCNK9) Subunits," The Journal of Neuroscience 24(30):6693-6702.

Berry et al., (Mar. 12, 1997). "Upper Airway Anesthesia Reduces Phasic Genioglossus Activity During Sleep Apnea," Am J Respir Crit Care Med 156:127-132.

Bittner et al., (2009). "TASK1 modulates inflammation and neurodegeneration in autoimmune inflammation of the central nervous system," Brain 132:2501-2516.

Brouillette et al. (1979). "A neuromuscular mechanism maintaining extrathoracic airway patency," American Physiological Society 49:772-779.

Comer, J. et al. (2001). "Lipophilicity Profiles: Theory and Measurement" in Pharmacokinetic Optimization in Drug Research Biological, Physicochemical, and Computational Strategies, Testa, B. et al. eds., Verlag Helvetica Chimica Acta: Zürich, Switzerland, pp. 275-304.

Czirják et al. (2000). "TASK (TWIK-Related Acid-Sensitive K+ Channel) is Expressed in Glomerulosa Cells of Rat Adrenal Cortex and Inhibited by Angiotensin II," Molecular Endocrinology 14(6):863-874.

Decher et al. (2001). "Characterization of TASK-4, a novel member of the pH-sensitive, two-pore domain potassium channel family," FEBS Letters 492:84-89.

Decher et al. (2011). "Knock-Out of the Potassium Channel TASK-1 Leads to a Prolonged QT Interval and a Disturbed QRS Complex," Cell Physiol Biochem 28:77-86.

Ertl, P. et al. (2000). "Fast Calculation of Molecular Polar Surface Area as a Sum of Fragment-Based Contributions and Its Application to the Prediction of Drug Transport Properties," J. Med. Chem. 43(20):3714-3717.

Hollandt et al. (2000). "Upper Airway Resistance Syndrome (UARS)—Obstructive Snoring," HNO 48:628-634.

International Preliminary Report on Patentability dated Jun. 12, 2018, for PCT Application No. PCT/EP2016/079973, filed on Dec. 7, 2016, 9 pages.

International Search Report & Written Opinion dated Feb. 20, 2017, for PCT/EP2016/079973, filed Dec. 7, 2016, 11 pages (German Language).

International Search Report & Written Opinion dated Jan. 26, 2017, for PCT/EP2016/079544, filed Dec. 2, 2016, 13 pages (German Language).

International Search Report and Written Opinion dated Oct. 17, 2017, for PCT/EP2017/067273, filed on Jul. 10, 2017, 13 pages (German Language).

Jungbauer, S. et al. (2017). "Sex-dependent differences in the in vivo respiratory pheynotype of the TASK-1 potassium channel knockout mouse," Respiratory Physiology & Neurobiology 245: 13-28.

Kim et al., (1999). "TBAK-1 and TASK-1, two-pore K+ channel subunits: kinetic properties and expression in rat heart," American Physiological Society H1669-H1678.

Kim et al., (2004). "Altered expression of KCNK9 in colorectal cancers," APMIS 112:588-594.

Kiper et al., (2015) "Kv1.5 blockers preferentially inhibit TASK-1 channels: TASK-1 as a target against atrial fibrillation and obstructive sleep apnea?" Pfluger Arch—EurJ Physiol 467:1081-1090.

Kuppens, T. et al. (2004). "Determination of absolute configuration via vibrational circular dichroism," Drug Discovery Today: Technologies 1(3): 269-275.

Limberg et al., (Oct. 28, 2011). "TASK-1 Channels May Modulate Action Potential Duration of Human Atrial Cardiomyocytes," Cell Physiol Biochem 25:613-624.

Liu et al., (2005). "Protective effects of TASK-3 (KCNK9) and related 2P K channels during cellular stress," Brain Research 1031:164-173.

Meuth et al., (May 23, 2008). "TWIK-related Acid-sensitive K+ Channel 1 (TASK1) and TASK3 Critically Influence T Lymphocyte Effector Functions," The Journal of Biological Chemistry 283(21):14559-14579.

Mu et al., (Mar. 2003). "Genomic amplification and oncogenic properties of the KCNK9 potassium channel gene," Cancer Cell 3:297-302.

Pocsai et al., (2006). "Melanoma cells exhibit strong intracellular TASK-3-specific immunopositivity in both tissue sections and cell culture," Cell Mol Life Sci 63:2364-2376.

Rinné et al., (2015). "TASK-1 and TASK-3 may form heterodimers in human atrial cardiomyocytes," Journal of Molecular and Cellular Cardiology 81:71-80.

Rowland, M. et al. (2011). "Well-Stirred Model of Hepatic Clearance" Appendix E in Clinical Pharmacokinetics and Pharmacodynamics Concepts and Applications, Fourth Edition, Troy, D. et al. eds., Lippincott Williams & Wilkins: Baltimore, MD, pp. 705-708.

Roy, A. et al. (2014). "Anandamide modulates carotid sinus nerve afferent activity via TRPV1 receptors increasing responses to heat," J. Appl. Physiol. 112: 212-224.

Stephens, P.J., (2004). "Vibrational Circular Dichroism Spectroscopy: A New Tool for the Stereochemical Characterization of Chiral Molecules" Chapter 26 in Computational Medicinal Chemistry for Drug Discovery, Bultinck, P. et al. eds., Marcel Dekker, Inc.: New York, NY, pp. 699-725.

Stühmer (1992). "Electrophysiological Recording from Xenopus Oocytes," Methods in Enzymology 207: 319-339.

Tang et al. (2009). "Endothelin-1 Inhibits Background Two-Pore Domain Channel TASK-1 in Primary Human Pulmonary Artery Smooth Muscle Cells," Am J Respir Cell Mol Biol 41:476-483.

Trapp et al. (Aug. 27, 2008). "A Role for TASK-1 (KCNK3) Channels in the Chemosensory Control of Breathing," The Journal of Neuroscience 28(35):8844-8850.

U.S. Appl. No. 16/319,106, filed Jan. 18, 2019, for Delbeck et al. A U.S. Patent Application is not submitted herewith pursuant to the waiver of 37 C.F.R. § 1.98(a)(2)(iii) issued by the Office dated Sep. 21, 2004.

(56) References Cited

OTHER PUBLICATIONS

Verse et al. (1999). "EMG Activity of the Genioglossus Muscle as One Parameter for Diagnosing for Obstructive Apnea," Somnologie 3:14-20 (Summary in English).

Vrints et al. (2013). "Cardiovascular Mechanisms and Consequences of Obstructive Sleep Aponea," Acta Clinica Belgica 68(3):169-178.

Whiteaker et al. (2001). "Validation of FLIPR Membrane Potential Dye for High Throughput Screening of Potassium Channel Modulators," Journal of Biomolecular Screening 6(5): 305-312.

Wirth et al. (2013). "Sensitization of Upper Airway Mechanoreceptors as a New Pharmacologic Principle to Treat Obstructive Sleep Apnea: Investigations with AVE0118 in Anesthetized Pigs," Sleep 36(5): 699-708.

\* cited by examiner

SUBSTITUTED PERHYDROPYRROLO[3,4-C]PYRROLE DERIVATIVES AND THE USE OF SAME

CROSS REFERENCE TO RELATED APPLICATIONS

This application is the national stage of International Application No. PCT/EP2016/079544, filed internationally on Dec. 2, 2016, which claims the benefit of European Application No. 15199268.2, filed Dec. 10, 2015.

The present application relates to novel (2-phenylimidazo[1,2-a]pyridin-3-yl)methyl-substituted perhydropyrrolo[3,4-c]pyrrole derivatives, to methods for the preparation thereof, to the use thereof alone or in combinations for treatment and/or prevention of diseases, and to the use thereof for production of medicaments for treatment and/or prevention of diseases, especially for treatment and/or prevention of respiratory disorders including sleep-related respiratory disorders such as obstructive sleep apneas and central sleep apneas and snoring.

Potassium channels are virtually ubiquitous membrane proteins which are involved in a large number of different physiological processes. This also includes the regulation of the membrane potential and the electric excitability of neurons and muscle cells. Potassium channels are divided into three major groups which differ in the number of transmembrane domains (2, 4 or 6). The group of potassium channels where two pore-forming domains are flanked by four transmembrane domains is referred to as K2P channels. Functionally, the K2P channels mediate, substantially time- and voltage-independently, $K^+$ background currents, and their contribution to the maintenance of the resting membrane potential is crucial. The family of the K2P channels includes 15 members which are divided into six subfamilies, based on similarities in sequence, structure and function: TWIK, TREK, TASK, TALK, THIK and TRESK.

Of particular interest are TASK-1 (KCNK3 or K2P3.1) and TASK-3 (KCNK9 or K2P9.1) of the TASK (TWIK-related acid-sensitive $K^+$ channel) subfamily. Functionally, these channels are characterized in that, during maintenance of voltage-independent kinetics, they have "leak" or "background" currents flowing through them, and they respond to numerous physiological and pathological influences by increasing or decreasing their activity. Characteristic of TASK channels is the sensitive reaction to a change in extracellular pH: the channels are inhibited at acidic pH and activated at alkaline pH.

TASK-1 is expressed mainly in the central nervous system and in the cardiovascular system. Relevant expression of TASK-1 was demonstrated in the brain, in spinal ganglia, in motoneurons of the *Nervus hypoglossus* and *Nervus trigeminus*, in the heart, *Glomus caroticum*, the pulmonary artery, aorta, lung, pancreas, placenta, uterus, kidney, adrenal gland, small intestine and stomach, and also on T lymphocytes. TASK-3 is expressed mainly in the central nervous system. Relevant expression of TASK-3 was demonstrated in the brain, in motoneurons of the *Nervus hypoglossus* and *Nervus trigeminus* and in neuroepithelial cells of the *Glomus caroticum* and the lung, and also on T lymphocytes. A lower expression is found in the heart, stomach, testicular tissue and adrenal gland.

TASK-1 and TASK-3 channels play a role in respiratory regulation. Both channels are expressed in the respiratory neurons of the respiratory center in the brain stem, inter alia in neurons which generate the respiratory rhythm (ventral respiratory group with pre-Botzinger complex), and in the noradrenergic *Locus caeruleus*, and also in serotonergic neurons of the raphe nuclei. Owing to the pH dependency, here the TASK channels have the function of a sensor which translates changes in extracellular pH into corresponding cellular signals [Bayliss et al., *Pflugers Arch.* 467, 917-929 (2015)]. TASK-1 and TASK-3 are also expressed in the *Glomus caroticum*, a peripheral chemoreceptor which measures pH, $O_2$ and $CO_2$ content of the blood and transmits signals to the respiratory center in the brain stem to regulate respiration. It was shown that TASK-1 knock-out mice have a reduced ventilatory response (increase of respiratory rate and tidal volume) to hypoxia and normoxic hypercapnia [Trapp et al., *J. Neurosci.* 28, 8844-8850 (2008)]. Furthermore, TASK-1 and TASK-3 channels were demonstrated in motoneurons of the *Nervus hypoglossus*, the XIIth cranial nerve, which has an important role in keeping the upper airways open [Berg et al., *J. Neurosci.* 24, 6693-6702 (2004)].

In a sleep apnea model in the anesthetized pig, intranasal administration of a potassium channel blocker which blocks the TASK-1 channel in the nanomolar range led to inhibition of collapsibility of the pharyngeal respiratory musculature and sensitization of the negative pressure reflex of the upper airways. It is assumed that intranasal administration of the potassium channel blocker depolarizes mechanoreceptors in the upper airways and, via activation of the negative pressure reflex, leads to increased activity of the musculature of the upper airways, thus stabilizing the upper airways and preventing collapse. By virtue of this stabilization of the upper airways, the TASK channel blockade may be of great importance for obstructive sleep apnea and also for snoring [Wirth et al., *Sleep* 36, 699-708 (2013); Kiper et al., *Pflugers Arch.* 467, 1081-1090 (2015)].

Obstructive sleep apnea (OSA) is a sleep-related respiratory disorder which is characterized by repeat episodes of obstruction of the upper airways. When breathing in, the patency of the upper airways is ensured by the interaction of two opposite forces. The dilative effects of the musculature of the upper airways counteract the negative intraluminal pressure, which constricts the lumen. The active contraction of the diaphragm and the other auxiliary respiratory muscles generates a negative pressure in the airways, thus constituting the driving force for breathing. The stability of the upper airways is substantially determined by the coordination and contraction property of the dilating muscles of the upper airways.

The *Musculus genioglossus* plays a decisive role in the pathogenesis of obstructive sleep apnea. The activity of the *Musculus genioglossus* increases with decreasing pressure in the pharynx in the sense of a dilative compensation mechanism. Innervated by the *Nervus hypoglossus*, it drives the tongue forward and downward, thus widening the pharyngeal airway [Verse et al., *Somnologie* 3, 14-20 (1999)]. Tensioning of the dilating muscles of the upper airways is modulated inter alia via mechanoreceptors/stretch receptors in the nasal cavity/pharynx [Bouillette et al., *J. Appl. Physiol. Respir. Environ. Exerc. Physiol.* 46, 772-779 (1979)]. In sleeping patients suffering from serious sleep apnea, under local anesthesia of the upper airway an additional reduction of the activity of the *Musculus genioglossus* can be observed [Berry et al., *Am. J. Respir. Crit. Care Med.* 156, 127-132 (1997)]. Patients suffering from obstructive sleep apnea have high mortality and morbidity as a result of cardiovascular disorders such as hypertension, myocardial infarction and stroke [Vrints et al., *Acta Clin. Belg.* 68, 169-178 (2013)].

In the case of central sleep apnea, owing to impaired brain function and impaired respiratory regulation there are episodic inhibitions of the respiratory drive. Central respiratory disorders result in mechanical respiratory arrests, i.e. during these episodes there is no breathing activity; temporarily, all respiratory muscles including the diaphragm are at rest. In the case of central sleep apnea, there is no obstruction of the upper airways.

In the case of primary snoring, there is likewise no obstruction of the upper airways. However, owing to the constriction of the upper airways, the flow rate of the air that is inhaled and exhaled increases. This, combined with the relaxed musculature, causes the soft tissues of the oral cavity and the pharynx to flutter in the stream of air. This gentle vibration then generates the typical snoring noises.

Obstructive snoring (upper airway resistance syndrome, heavy snoring, hypopnea syndrome) is caused by repeat partial obstruction of the upper airways during sleep. This results in an increased airway resistance and thus in an increase in work of breathing with considerable fluctuations in intrathoracic pressure. During inspiration, the negative intrathoracic pressure may reach values similar to those that are encountered as a result of complete airway obstruction during obstructive sleep apnea. The pathophysiological consequences for heart, circulation and sleep quality correspond to those of obstructive sleep apnea. As in obstructive sleep apnea, the pathogenesis is assumed to be an impaired reflex mechanism of the pharynx-dilating muscles during inspiration when sleeping. Frequently, obstructive snoring is the preliminary stage of obstructive sleep apnea [Hollandt et al., *HNO* 48, 628-634 (2000)].

In addition, TASK channels also appear to play a role in the apoptosis of neurons. In the animal model of myelin oligodendrocyte glycoprotein (MOG)-induced autoimmune encephalomyelitis, an animal model of multiple sclerosis, TASK-1 knock-out mice showed reduced neuronal degeneration. By preventing neuronal apoptosis, inhibition of TASK channels appears to act neuroprotectively, and may thus be of interest for the treatment of neurodegenerative disorders [Bittner et al., *Brain* 132, 2501-2516 (2009)].

Furthermore, it has been described that T lymphocytes express TASK-1 and TASK-3 channels and that inhibition of these channels leads to reduced cytokine production and proliferation after stimulation of T lymphocytes. The selective inhibition of TASK channels on T lymphocytes improved the course of the disease in an animal model of multiple sclerosis. The blockade of TASK channels may therefore also be of importance for treatment of autoimmune disorders [Meuth et al., *J. Biol. Chem.* 283, 14559-14579 (2008)].

TASK-1 and TASK-3 are also expressed in the heart [Rinné et al., *J. Mol. Cell. Cardiol.* 81, 71-80 (2015)]. Since TASK-1 is expressed particularly strongly in the nervous stimuli conduction system and in the atrium, this channel may have a role in disrupting stimuli conduction or triggering supraventricular arrhythmias. In the heart, TASK-1 appears to contribute to a background current which for its part contributes to maintenance of the resting potential, to action potential duration and to repolarization [Kim et al., *Am. J. Physiol.* 277, H1669-1678 (1999)]. Using human heart muscle cells, it was shown that blockade of the TASK-1 ion current results in a longer action potential [Limberg et al., *Cell. Physiol. Biochem.* 28, 613-624 (2011)]. Furthermore, for TASK-1 knock-out mice a prolonged QT time was demonstrated [Decher et al., *Cell. Physiol. Biochem.* 28, 77-86 (2011)]. Inhibition of TASK channels may therefore be of importance for the treatment of cardiac arrhythmias, in particular atrial fibrillation.

In certain vessels, TASK channels also appear to play a role in the regulation of the vascular tone. A relevant expression of TASK-1 was noticed in smooth muscles of pulmonary and mesenteric arteries. In studies on smooth muscle cells of human pulmonary arteries, it was shown that TASK-1 plays a role in the regulation of the pulmonary vascular tone. TASK-1 may be involved in hypoxic and acidosis-induced pulmonary vasoconstriction [Tang et al., *Am. J. Respir. Cell. Mol. Biol.* 41, 476-483 (2009)].

In glomerulosa cells of the adrenal cortex, TASK-1 plays a role in potassium conductivity [Czirjak et al., *Mol. Endocrinol.* 14, 863-874 (2000)].

Possibly, TASK channels also play an important role in apoptosis and tumorigenesis. In breast cancer, colon cancer and lung cancer biopsies and also in metastasizing prostate cancer and in melanoma cells, TASK-3 has been found to be strongly overexpressed [Mu et al., *Cancer Cell* 3, 297-302 (2003); Kim et al., *APMIS* 112, 588-594 (2004); Pocsai et al., *Cell. Mol. Life Sci.* 63, 2364-2376 (2006)]. A point mutation at the TASK-3 channel, which switches off the channel function, simultaneously cancels the tumor-forming action (proliferation, tumor growth, apoptosis resistance) [Mu et al., *Cancer Cell* 3, 297-302 (2003)]. Overexpression of TASK-3 and TASK-1 in a murine fibroblast cell line (C8 cells) inhibits intracellular apoptosis routes [Liu et al., *Brain Res.* 1031, 164-173 (2005)]. Accordingly, the blockade of TASK channels may also be relevant for the treatment of various neoplastic disorders.

Therefore, it is an object of the present invention to provide novel substances which act as potent and selective blockers of TASK-1 and TASK-3 channels and, as such, are suitable in particular for the treatment and/or prevention of respiratory disorders including sleep-related respiratory disorders such as obstructive and central sleep apnea and snoring, and also other disorders.

US 2002/0022624-A1 describes various azaindole derivatives including imidazo[1,2-a]pyridines as substance P antagonists for the treatment of CNS disorders. WO 2004/035578-A1 discloses 3-(aminomethyl)imidazo[1,2-a]pyridine derivatives as inhibitors of NO synthase which can be employed for the treatment of various disorders. WO 2009/143156-A2 claims 2-phenylimidazo[1,2-a]pyridine derivatives which, as modulators of $GABA_A$ receptors, are likewise suitable for treating CNS disorders. WO 2011/113606-A1 and WO 2012/143796-A2 disclose bicyclic imidazole derivatives suitable for the treatment of bacterial infections and inflammatory disorders. EP 2 671 582-A1 discloses bicyclic imidazole derivatives and options for their therapeutic use as inhibitors of T type calcium channels. WO 2012/130322-A1 describes 2,6-diaryl-3-(piperazinomethyl) imidazo[1,2-a]pyridine derivatives which, by virtue of their HIF-1 inhibiting activity, are suitable in particular for the treatment of inflammatory and hyperproliferative disorders. WO 2014/187922-A1 discloses various 2-phenyl-3-(piperazinomethyl)imidazo[1,2-a]pyridine derivatives as inhibitors of glucose transporters (GLUT) which can be employed for treating inflammatory, proliferative, metabolic, neurological and/or autoimmune disorders. WO 2015/144605-A1 describes acylated bicyclic amine compounds as inhibitors of autotaxin and of lysophosphatidic acid production which are suitable for the treatment of various disorders.

The present invention provides compounds of the general formula (I)

(I)

in which
R¹ represents halogen, cyano or $(C_1-C_4)$-alkyl,
and
R² represents $(C_4-C_6)$-cycloalkyl in which a ring $CH_2$ group may be replaced by —O—
or
R² represents a phenyl group of the formula (a) or a pyridyl group of the formula (b)

(a)

(b)

in which * marks the bond to the adjacent carbonyl group
and
R³ represents hydrogen, fluorine, chlorine, bromine, cyano, $(C_1-C_3)$-alkyl or $(C_1-C_3)$-alkoxy,
where $(C_1-C_3)$-alkyl and $(C_1-C_3)$-alkoxy may be up to trisubstituted by fluorine,
R⁴ represents hydrogen, fluorine, chlorine, bromine or methyl,
R⁵ represents hydrogen, fluorine, chlorine, bromine or methyl
and
R⁶ represents hydrogen or $(C_1-C_3)$-alkoxy which may be up to trisubstituted by fluorine,
or
R² represents an —OR⁷ or —NR⁸R⁹ group in which
R⁷ and R⁸ in each case represent $(C_1-C_4)$-alkyl, $(C_4-C_6)$-cycloalkyl, phenyl, benzyl, 1-phenylethyl or 2-phenylethyl,
where $(C_1-C_4)$-alkyl may be up to trisubstituted by fluorine,
and
where phenyl and the phenyl groups in benzyl, 1-phenylethyl and 2-phenylethyl may be up to disubstituted by identical or different radicals selected from the group consisting of fluorine, chlorine, methyl, ethyl, trifluoromethyl, methoxy and ethoxy,
and
R⁹ is hydrogen or methyl,
or
R⁸ and R⁹ are attached to one another and, together with the nitrogen atom to which they are bonded, form a tetrahydroquinoline ring of the formula (c) or a tetrahydroisoquinoline ring of the formula (d), (c)

(d)

in which ** marks the bond to the carbonyl group,
and the salts, solvates and solvates of the salts thereof.

Inventive compounds are the compounds of the formula (I) and the salts, solvates and solvates of the salts thereof, the compounds of the formulae (I-A), (I-B) and (I-C) below that are encompassed by formula (I) and the salts, solvates and solvates of the salts thereof, and the compounds cited hereinafter as working examples that are encompassed by formula (I) and the salts, solvates and solvates of the salts thereof, if the compounds cited hereinafter that are encompassed by formula (I) are not already salts, solvates and solvates of the salts.

Preferred salts in the context of the present invention are physiologically acceptable salts of the compounds according to the invention. Also encompassed are salts which are not themselves suitable for pharmaceutical applications but can be used, for example, for the isolation, purification or storage of the compounds of the invention.

Physiologically acceptable salts of the compounds of the invention include acid addition salts of mineral acids, carboxylic acids and sulfonic acids, for example salts of hydrochloric acid, hydrobromic acid, sulfuric acid, phosphoric acid, methanesulfonic acid, ethanesulfonic acid, benzenesulfonic acid, toluenesulfonic acid, naphthalenedisulfonic acid, formic acid, acetic acid, trifluoroacetic acid, propionic acid, succinic acid, fumaric acid, maleic acid, lactic acid, tartaric acid, malic acid, citric acid, gluconic acid, benzoic acid and embonic acid.

Solvates in the context of the invention are described as those forms of the compounds according to the invention which form a complex in the solid or liquid state by coordination with solvent molecules. Hydrates are a specific form of the solvates in which the coordination is with water. Solvates preferred in the context of the present invention are hydrates.

The compounds according to the invention may, depending on their structure, exist in different stereoisomeric forms, i.e. in the form of configurational isomers or else, if appropriate, as conformational isomers (enantiomers and/or diastereomers, including those in the case of atropisomers). The present invention therefore encompasses the enantiomers and diastereomers, and the respective mixtures thereof.

The stereoisomerically homogeneous constituents can be isolated from such mixtures of enantiomers and/or diastereomers in a known manner; chromatography processes are preferably used for this purpose, especially HPLC chromatography on an achiral or chiral phase.

If the compounds of the invention can occur in tautomeric forms, the present invention encompasses all the tautomeric forms.

The present invention also encompasses all suitable isotopic variants of the compounds according to the invention. An isotopic variant of a compound according to the invention is understood here to mean a compound in which at least one atom within the compound according to the invention has been exchanged for another atom of the same atomic number, but with a different atomic mass from the atomic mass which usually or predominantly occurs in nature. Examples of isotopes which can be incorporated into a compound according to the invention are those of hydrogen, carbon, nitrogen, oxygen, phosphorus, sulfur, fluorine, chlorine, bromine and iodine, such as $^2$H (deuterium), $^3$H (tritium), $^{13}$C, $^{14}$C, $^{15}$N, $^{17}$O, $^{18}$O, $^{32}$P, $^{33}$P, $^{33}$S, $^{34}$S, $^{35}$S, $^{36}$S, $^{18}$F, $^{36}$Cl, $^{82}$Br, $^{123}$B, $^{124}$, $^{129}$I and $^{131}$I. Particular isotopic variants of a compound according to the invention, especially those in which one or more radioactive isotopes have been incorporated, may be beneficial, for example, for the examination of the mechanism of action or of the active ingredient distribution in the body; due to the comparatively easy preparability and detectability, especially compounds labeled with $^3$H or $^{14}$C isotopes are suitable for this purpose. In addition, the incorporation of isotopes, for example of deuterium, can lead to particular therapeutic benefits as a consequence of greater metabolic stability of the compound, for example an extension of the half-life in the body or a reduction in the active dose required; such modifications of the compounds of the invention may therefore possibly also constitute a preferred embodiment of the present invention. Isotopic variants of the compounds of the invention can be prepared by commonly used processes known to those skilled in the art, for example by the methods described further down and the procedures described in the working examples, by using corresponding isotopic modifications of the respective reagents and/or starting compounds.

The present invention additionally also encompasses prodrugs of the compounds according to the invention. The term "prodrugs" refers here to compounds which may themselves be biologically active or inactive, but are converted while present in the body, for example by a metabolic or hydrolytic route, to compounds of the invention.

In the context of the present invention, unless specified otherwise, the substituents and radicals are defined as follows:

In the context of the invention, $(C_1-C_4)$-alkyl is a straight-chain or branched alkyl radical having 1 to 4 carbon atoms. Examples include: methyl, ethyl, n-propyl, isopropyl, n-butyl, isobutyl, sec-butyl and tert-butyl.

In the context of the invention, $(C_1-C_3)$-alkyl is a straight-chain or branched alkyl radical having 1 to 3 carbon atoms. Examples include: methyl, ethyl, n-propyl and isopropyl.

$(C_1-C_3)$-Alkoxy in the context of the invention is a straight-chain or branched alkoxy radical having 1 to 3 carbon atoms. Examples include: methoxy, ethoxy, n-propoxy and isopropoxy.

$(C_4-C_6)$-Cycloalkyl in the context of the invention is a monocyclic saturated cycloalkyl group having 4 to 6 carbon atoms. Examples include: cyclobutyl, cyclopentyl and cyclohexyl.

Halogen in the context of the invention includes fluorine, chlorine, bromine and iodine. Preference is given to fluorine, chlorine or bromine.

In the context of the present invention, all radicals which occur more than once are defined independently of one another. When radicals in the compounds of the invention are substituted, the radicals may be mono- or polysubstituted, unless specified otherwise. Substitution by one substituent or by two identical or different substituents is preferred. Particular preference is given to substitution by one substituent.

Preference is given in the context of the present invention to compounds of the formula (I) in which
$R^1$ represents chlorine, bromine or isopropyl,
and
$R^2$ represents cyclobutyl, cyclopentyl or cyclohexyl
or
$R^2$ represents a phenyl group of the formula (a) or a pyridyl group of the formula (b)

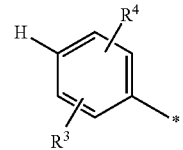

(a)

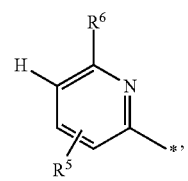

(b)

in which * marks the bond to the adjacent carbonyl group
and
$R^3$ represents fluorine, chlorine, methyl, trifluoromethyl, methoxy or trifluoromethoxy,
$R^4$ represents hydrogen or fluorine,
$R^5$ represents hydrogen, fluorine, chlorine or methyl
and
$R^6$ represents methoxy, difluoromethoxy, trifluoromethoxy or isopropoxy,
or
$R^2$ represents an —$OR^7$ or —$NR^8R^9$ group in which
$R^7$ represents isopropyl, isobutyl, tert-butyl, cyclopentyl, phenyl or benzyl,
where phenyl and the phenyl group in benzyl may be up to disubstituted by identical or different radicals selected from the group consisting of fluorine, chlorine, methyl, trifluoromethyl, methoxy and ethoxy,
$R^8$ represents phenyl, benzyl or 1-phenylethyl,
where phenyl and the phenyl groups in benzyl and 1-phenylethyl may be up to disubstituted by identical or different radicals selected from the group consisting of fluorine, chlorine, methyl, trifluoromethyl, methoxy and ethoxy,
and
$R^9$ is hydrogen or methyl,
or
$R^8$ and $R^9$ are attached to one another and, together with the nitrogen atom to which they are bonded, form a tetrahydroquinoline ring of the formula (c),

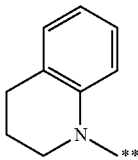

in which ** marks the bond to the carbonyl group,
and the salts, solvates and solvates of the salts thereof.

A particular embodiment of the present invention relates to compounds of the formula (I) in which
$R^1$ represents chlorine or bromine,
and the salts, solvates and solvates of the salts thereof.

A further particular embodiment of the present invention relates to compounds of the formula (I) in which
$R^2$ represents cyclobutyl or cyclopentyl,
and the salts, solvates and solvates of the salts thereof.

A further particular embodiment of the present invention relates to compounds of the formula (I) in which
$R^2$ represents a phenyl group of the formula (a)

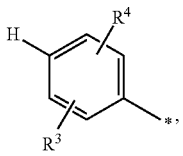

in which * marks the bond to the adjacent carbonyl group,
$R^3$ represents fluorine, chlorine, methyl, trifluoromethyl or methoxy
and
$R^4$ represents hydrogen or fluorine,
and the salts, solvates and solvates of the salts thereof.

A further particular embodiment of the present invention relates to compounds of the formula (I) in which
$R^2$ represents a pyridyl group of the formula (b)

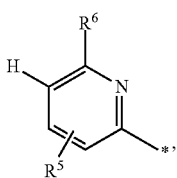

in which * marks the bond to the adjacent carbonyl group,
$R^5$ represents hydrogen
and
$R^6$ represents $(C_1-C_3)$-alkoxy which may be up to trisubstituted by fluorine,
and the salts, solvates and solvates of the salts thereof.

A further particular embodiment of the present invention relates to compounds of the formula (I) in which
$R^2$ represents a pyridyl group of the formula (b)

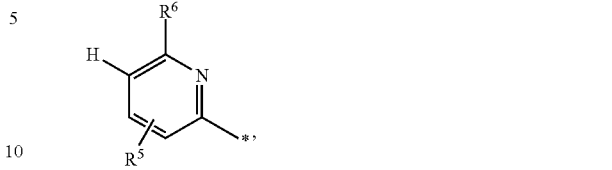

in which * marks the bond to the adjacent carbonyl group,
$R^5$ represents hydrogen, fluorine or methyl
and
$R^6$ represents methoxy,
and the salts, solvates and solvates of the salts thereof.

A further particular embodiment of the present invention relates to compounds of the formula (I) in which
$R^2$ represents an $—OR^7$ group in which
$R^7$ represents phenyl or benzyl,
where phenyl and the phenyl group in benzyl may be up to disubstituted by identical or different radicals selected from the group consisting of fluorine, chlorine, methyl, trifluoromethyl, methoxy and ethoxy,
and the salts, solvates and solvates of the salts thereof.

A further particular embodiment of the present invention relates to compounds of the formula (I) in which
$R^2$ represents an $—NR^8R^9$ group in which
$R^8$ represents phenyl or 1-phenylethyl,
where phenyl and the phenyl group in 1-phenylethyl may be up to disubstituted by identical or different radicals selected from the group consisting of fluorine, chlorine, methyl, trifluoromethyl, methoxy and ethoxy,
and
$R^9$ is hydrogen,
or
$R^8$ and $R^9$ are attached to one another and, together with the nitrogen atom to which they are bonded, form a tetrahydroquinoline ring of the formula (c),

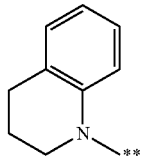

in which ** marks the bond to the carbonyl group,
and the salts, solvates and solvates of the salts thereof.

In the context of the present invention, particular preference is given to compounds of the formula (I) in which
$R^1$ represents chlorine, bromine or isopropyl,
and
$R^2$ represents cyclobutyl or cyclopentyl,
or
$R^2$ represents a phenyl group of the formula (a) or a pyridyl group of the formula (b)

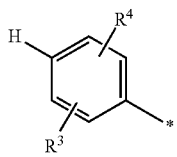

-continued (b)

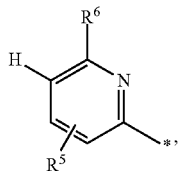

in which * marks the bond to the adjacent carbonyl group
and
$R^3$ represents fluorine, chlorine, methyl, trifluoromethyl or methoxy,
$R^4$ represents hydrogen or fluorine,
$R^5$ represents hydrogen, fluorine or methyl
and
$R^6$ represents methoxy,
or
$R^2$ represents an —$OR^7$ or —$NR^8R^9$ group in which
  $R^7$ represents isopropyl, cyclopentyl, phenyl or benzyl,
    where phenyl and the phenyl group in benzyl may be up to disubstituted by identical or different radicals selected from the group consisting of fluorine, chlorine, methyl, trifluoromethyl, methoxy and ethoxy,
  $R^8$ represents phenyl or 1-phenylethyl,
    where phenyl and the phenyl group in 1-phenylethyl may be up to disubstituted by identical or different radicals selected from the group consisting of fluorine, chlorine, methyl, trifluoromethyl, methoxy and ethoxy,
  and
  $R^9$ is hydrogen,
  or
  $R^8$ and $R^9$ are attached to one another and, together with the nitrogen atom to which they are bonded, form a tetrahydroquinoline ring of the formula (c), (c)

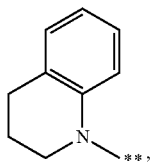

in which ** marks the bond to the carbonyl group,
and the salts, solvates and solvates of the salts thereof.
Compounds of the formula (I) which are especially preferred in the context of the present invention are those in which
$R^1$ represents chlorine or isopropyl,
and
$R^2$ represents a pyridyl group of the formula (b)

(b)

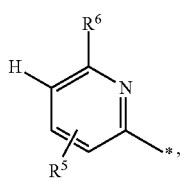

in which * marks the bond to the adjacent carbonyl group,
$R^5$ represents hydrogen, fluorine or methyl
and
$R^6$ represents methoxy,
and the salts, solvates and solvates of the salts thereof.

The individual radical definitions specified in the respective combinations or preferred combinations of radicals are, independently of the respective combinations of the radicals specified, also replaced as desired by radical definitions of other combinations.

Very particular preference is given to combinations of two or more of the abovementioned preferred ranges.

The invention furthermore provides a method for preparing the compounds of the formula (I) according to the invention, characterized in that a compound of the formula (II)

(II)

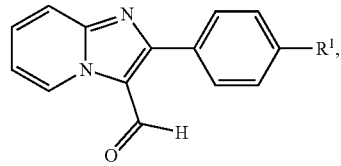

in which $R^1$ has the definition specified above,
is reacted in the presence of a suitable reducing agent either
[A] with a compound of the formula (III)

(III)

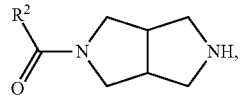

in which $R^2$ has the definition specified above,
to give a compound of the formula (I)
or
[B] with a protected perhydropyrrolo[3,4-c]pyrrole of the formula (IV)

(IV)

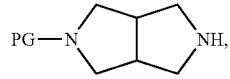

in which PG represents a suitable amino protecting group such as, for example, tert-butoxycarbonyl, benzyloxycarbonyl or (9H-fluoren-9-ylmethoxy)carbonyl,
at first to give a compound of the formula (V)

(V)

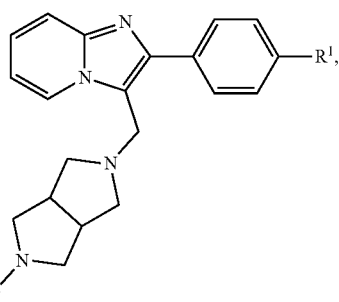

in which PG and $R^1$ have the definitions specified above, then the protecting group PG is cleaved and the resulting compound of the formula (VI)

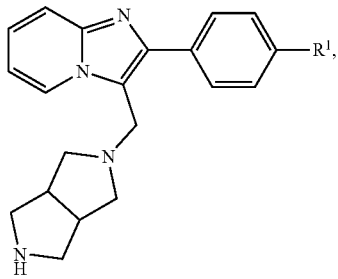
(VI)

in which R$^1$ has the definition specified above,
is then reacted, depending on the specific definition of the R$^2$ radical,
[B-1] with a carboxylic acid of the formula (VII)

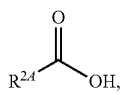
(VII)

in which
R$^{2A}$ represents (C$_4$-C$_6$)-cycloalkyl in which a ring CH$_2$ group may be replaced by —O—, or is a phenyl group of the formula (a) or a pyridyl group of the formula (b), as described above,
with activation of the carboxylic acid function in (VII), or is reacted with the corresponding acid chloride of the formula (VIII)

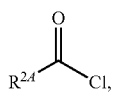
(VIII)

in which R$^{2A}$ has the definition specified above,
to give a compound of the formula (I-A)

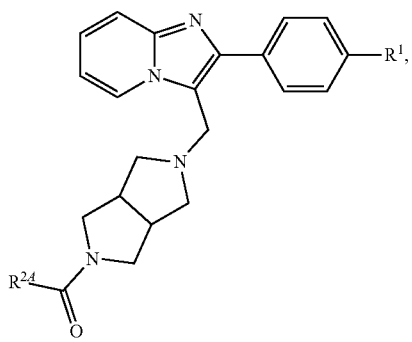
(I-A)

in which R$^1$ and R$^{2A}$ have the definitions specified above,
or is reacted
[B-2] with a chloroformate or carbamoyl chloride of the formula (IX)

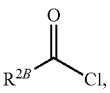
(IX)

in which
R$^{2B}$ represents the —OR$^7$ or —NR$^8$R$^{9A}$ group in which R$^7$ and R$^8$ have the definitions specified above
and
R$^{9A}$ has the definition of R$^9$ specified above, but is not hydrogen,
to give a compound of the formula (I-B)

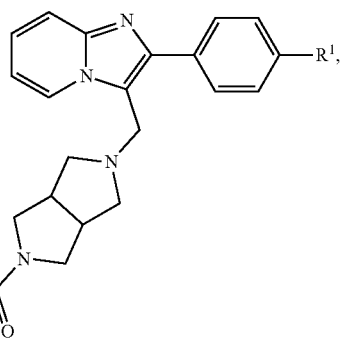
(I-B)

in which R$^1$ and R$^{2B}$ have the definitions specified above,
or is reacted
[B-3] with an isocyanate of the formula (X)

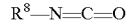
R$^8$—N═C═O (X), in which R$^8$ has the definition specified above,
to give a compound of the formula (I-C)

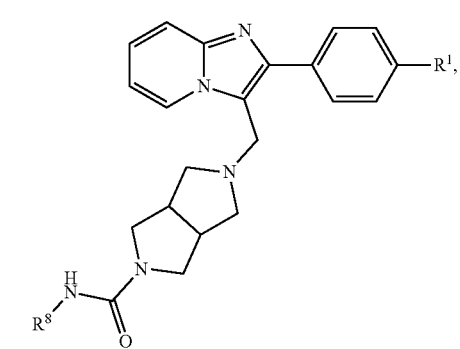
(I-C)

in which R$^1$ and R$^8$ have the definitions specified above,
and the resulting compounds of the formulae (I), (I-A), (I-B) or (I-C) are optionally converted with the appropriate (i) solvents and/or (ii) acids into their solvates, salts and/or solvates of the salts.

Suitable reducing agents for the method steps [A] (II)+(III)→(I) and [B] (II)+(IV)→(V) [reductive aminations] for such purposes are customary alkali metal borohydrides such as sodium borohydride, sodium cyanoborohydride or sodium triacetoxyborohydride; preference is given to using sodium triacetoxyborohydride. The addition of an acid, such as acetic acid in particular, and/or of a dehydrating agent, for example molecular sieve or trimethyl orthoformate or triethyl orthoformate, may be advantageous in these reactions.

Suitable solvents for these reactions are especially alcohols such as methanol, ethanol, n-propanol or isopropanol, ethers such as diisopropyl ether, methyl tert-butyl ether, tetrahydrofuran, 1,4-dioxane or 1,2-dimethoxyethane, polar aprotic solvents such as acetonitrile or N,N-dimethylformamide (DMF) or mixtures of such solvents; preference is given to using tetrahydrofuran. The reactions are generally effected within a temperature range of 0° C. to +50° C.

The protecting group PG used in compound (IV) may be a standard amino protecting group, for example tert-butoxycarbonyl (Boc), benzyloxycarbonyl (Z) or (9H-fluoren-9-ylmethoxy)carbonyl (Fmoc); preference is given to using tert-butoxycarbonyl (Boc). The detachment of the protecting group in method step [B] (V)→(VI) is effected by known methods. Thus, the tert-butoxycarbonyl group is typically cleaved by treatment with a strong acid such as hydrogen chloride, hydrogen bromide or trifluoroacetic acid, in an inert solvent such as diethyl ether, 1,4-dioxane, dichloromethane or acetic acid. In the case of benzyloxycarbonyl as protecting group, this is preferably removed by hydrogenolysis in the presence of a suitable palladium catalyst such as palladium on activated carbon. The (9H-fluoren-9-ylmethoxy)carbonyl group is generally cleaved with the aid of a secondary amine base such as diethylamine or piperidine [see e.g. T. W. Greene and P. G. M. Wuts, *Protective Groups in Organic Synthesis*, Wiley, New York, 1999; P. J. Kocienski, *Protecting Groups*, 3$^{rd}$ edition, Thieme, 2005].

Particular compounds of the formula (V), for example those in which PG is tert-butoxycarbonyl or benzyloxycarbonyl, likewise have significant inhibitory activity with respect to TASK-1 and TASK-3, and in this respect are also encompassed by the scope of definition of the present invention, i.e. the compounds of the formula (I).

The process step [B-1] (VI)+(VII)→(I-A) [amide formation] is conducted by known methods with the aid of a condensing or activating agent. Suitable agents of this kind are, for example, carbodiimides such as N,N'-diethyl-, N,N'-dipropyl-, N,N'-diisopropyl-, N,N'-dicyclohexylcarbodiimide (DCC) or N-(3-dimethylaminopropyl)-N'-ethylcarbodiimide hydrochloride (EDC), phosgene derivatives such as N,N'-carbonyldiimidazole (CDI) or isobutyl chloroformate, 1,2-oxazolium compounds such as 2-ethyl-5-phenyl-1,2-oxazolium 3-sulfate or 2-tert-butyl-5-methylisoxazolium perchlorate, acylamino compounds such as 2-ethoxy-1-ethoxycarbonyl-1,2-dihydroquinoline, α-chlorenamines such as 1-chloro-N,N,2-trimethylprop-1-en-1-amine, 1,3,5-triazine derivatives such as 4-(4,6-dimethoxy-1,3,5-triazin-2-yl)-4-methylmorpholinium chloride, phosphorus compounds such as n-propanephosphonic anhydride (PPA), diethyl cyanophosphonate, diphenylphosphoryl azide (DPPA), bis(2-oxo-3-oxazolidinyl)phosphoryl chloride, benzotriazol-1-yloxytris(dimethylamino)phosphonium hexafluorophosphate or benzotriazol-1-yloxytris(pyrrolidino)phosphonium hexafluorophosphate (PyBOP), or uronium compounds such as O-(benzotriazol-1-yl)-N,N,N',N'-tetramethyluronium tetrafluoroborate (TBTU), O-(1H-6-chlorobenzotriazol-1-yl)-1,1,3,3-tetramethyluronium tetrafluoroborate (TCTU), O-(benzotriazol-1-yl)-N,N,N'N'-tetramethyluronium hexafluorophosphate (HBTU), O-(7-azabenzotriazol-1-yl)-N,N,N',N'-tetramethyluronium hexafluorophosphate (HATU) or 2-(2-oxo-1-(2H)-pyridyl)-1,1,3,3-tetramethyluronium tetrafluoroborate (TPTU), optionally in combination with further auxiliaries such as 1-hydroxybenzotriazole (HOBt) or N-hydroxysuccinimide (HOSu), and also as base an alkali metal carbonate, for example sodium carbonate or potassium carbonate, or a tertiary amine base such as triethylamine, N,N-diisopropylethylamine, N-methylmorpholine (NMM), N-methylpiperidine (NMP), pyridine or 4-N,N-dimethylaminopyridine (DMAP). The condensing agent or activating agent used with preference is O-(7-azabenzotriazol-1-yl)-N,N,N'N'-tetramethyluronium hexafluorophosphate (HATU) in combination with N,N-diisopropylethylamine as base.

The alternative process via the carbonyl chloride (VIII) [(VI)+(VIII)→(I-A)] is generally effected in the presence of a base such as sodium carbonate, potassium carbonate, triethylamine, N,N-diisopropylethylamine, N-methylmorpholine (NMM), N-methylpiperidine (NMP), pyridine, 2,6-dimethylpyridine, 4-N,N-dimethylaminopyridine (DMAP), 1,5-diazabicyclo[4.3.0]non-5-ene (DBN) or 1,8-diazabicyclo[5.4.0]undec-7-ene (DBU); preference is given to using triethylamine or N,N-diisopropylethylamine.

Suitable inert solvents for these amide-forming reactions are, for example, ethers such as diethyl ether, diisopropyl ether, methyl tert-butyl ether, tetrahydrofuran, 1,4-dioxane, 1,2-dimethoxyethane or bis(2-methoxyethyl) ether, hydrocarbons such as benzene, toluene, xylene, pentane, hexane or cyclohexane, halohydrocarbons such as dichloromethane, trichloromethane, carbon tetrachloride, 1,2-dichloroethane, trichloroethylene or chlorobenzene, or polar aprotic solvents such as acetone, methyl ethyl ketone, ethyl acetate, acetonitrile, butyronitrile, pyridine, dimethyl sulfoxide (DMSO), N,N-dimethylformamide (DMF), N,N'-dimethylpropyleneurea (DMPU) or N-methylpyrrolidinone (NMP); it is also possible to use mixtures of such solvents. Preference is given to using dichloromethane, 1,2-dichloroethane, tetrahydrofuran, N,N-dimethylformamide or mixtures of these solvents. The reactions are generally conducted within a temperature range of from −20° C. to +60° C., preferably at from 0° C. to +40° C.

The process [B-2] (VI)+(IX)→(I-B) [formation of urethanes or substituted ureas] is conducted under similar reaction conditions with regard to solvent, addition of base and temperature as described above for the amide formation [B-1] (VI)+(VIII)→(I-A).

The reaction [B-3] (VI)+(X)→(I-C) is likewise effected in one of the above-listed inert solvents or solvent mixtures at a temperature in the range from 0° C. to +60° C.; the addition of a base in this reaction can optionally be dispensed with.

The amine compound (VI) can also be used in the process steps [B-1] (VI)+(VII) or (VIII)→(I-A), [B-2] (VI)+(IX)→(I-B) and [B-3] (VI)+(X)→(I-C) in the form of a salt, for example as hydrochloride or trifluoroacetate. In such a case, the conversion is effected in the presence of an appropriately increased amount of the respective auxiliary base used.

The processes described above can be conducted at atmospheric, elevated or reduced pressure (for example in the range from 0.5 to 5 bar); in general, the reactions are each carried out at atmospheric pressure.

For their part, the compounds of the formula (II) can be prepared by processes known from the literature by condensing 2-aminopyridine (XI)

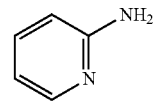

(XI)

in the presence of a base with an acetophenone derivative of the formula (XII)

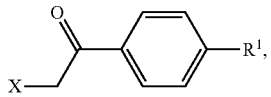 (XII)

in which R¹ has the definition specified above
and
X represents a suitable leaving group, for example chlorine, bromine or iodine,
to give a 2-phenylimidazo[1,2-a]pyridine of the formula (XIII)

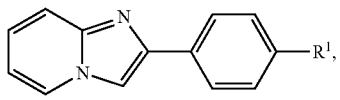 (XIII)

in which R¹ has the definition specified above,
and then formylating this with a mixture of N,N-dimethylformamide and phosphorus oxychloride to give (II).

The condensation reaction (XI)+(XII)→(XIII) is usually carried out in an alcoholic solvent such as methanol, ethanol, n-propanol, isopropanol or n-butanol, in an ether such as diethyl ether, diisopropyl ether, methyl tert-butyl ether, tetrahydrofuran, 1,4-dioxane, 1,2-dimethoxyethane or bis(2-methoxyethyl) ether, or in a dipolar aprotic solvent such as N,N-dimethylformamide (DMF), N,N'-dimethylpropyleneurea (DMPU) or N-methylpyrrolidinone (NMP), at a temperature in the range from +20° C. to +120° C.; preferably, the solvent used is ethanol.

Bases suitable for this reaction are in particular alkali metal bicarbonates or carbonates such as sodium bicarbonate or potassium bicarbonate or lithium carbonate, sodium carbonate, potassium carbonate or cesium carbonate, or else alumina; preference is given to using sodium bicarbonate. Optionally—if the reaction temperature is increased correspondingly—the reaction can also be carried out without addition of a base.

The regioselective formylation (XIII)→(II) is effected under the standard conditions of a Vilsmaier-Haack reaction by treatment of (XIII) with a preformed mixture of N,N-dimethylformamide and phosphorus oxychloride which is used in a large excess and simultaneously also serves as solvent. The reaction is generally carried out within a temperature range of from 0° C. to +100° C.

The compounds of the formulae (III), (IV), (VII), (VIII), (IX), (X), (XI) and (XII) are either commercially available or described as such in the literature, or they can be prepared in a simple manner from other commercially available compounds by methods familiar to the person skilled in the art and known from the literature. Numerous detailed procedures and further literature references can also be found in the experimental section, in the section on the preparation of the starting compounds and intermediates.

The preparation of the compounds of the invention can be illustrated by way of example by the following reaction schemes:

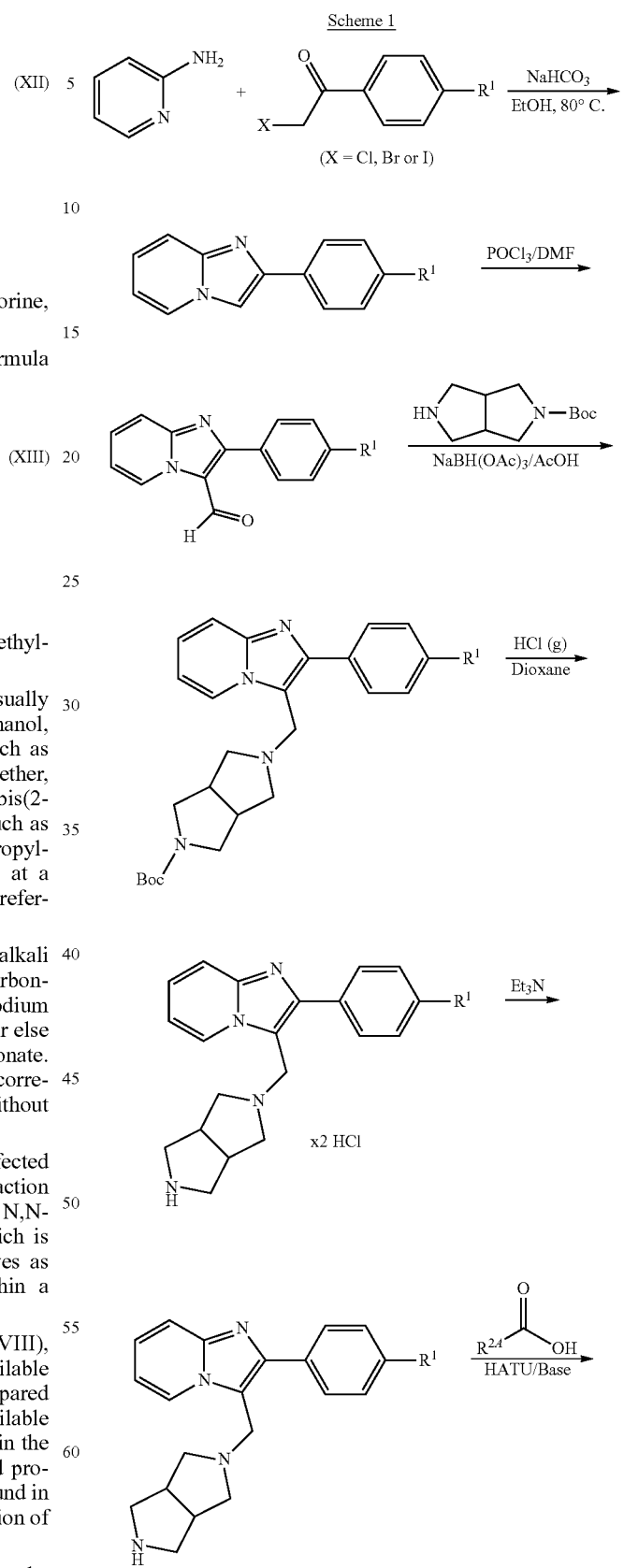

Scheme 1

-continued

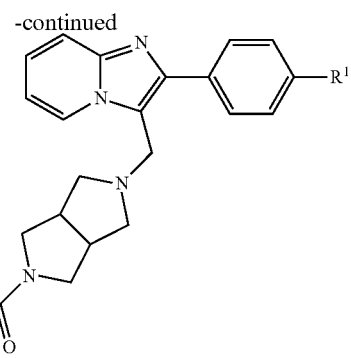

[$R^{24}$ = $C_4$-$C_6$-cycloalkyl in which a ring $CH_2$ group may be replaced by —O—, or is a phenyl group of the formula (a) or a pyridyl group of the formula (b) (as described above as part of the scope of the definition of $R^2$)].

tive sleep apnea (in adults and children), primary snoring, obstructive snoring (upper airway resistance syndrome, heavy snoring, hypopnea syndrome), central sleep apnea, mixed sleep apnea, Cheyne-Stokes respiration, primary sleep apnea of infancy, apparent life-threatening event, central sleep apnea as a result of the use of medicaments or the use of other substances, obesity hypoventilation syndrome, disrupted central respiratory drive, sudden infant death, primary alveolar hypoventilation syndrome, postoperative hypoxia and apnea, muscular respiratory disorders, respiratory disorders following long-term ventilation, respiratory disorders during adaptation in high mountains, acute and chronic pulmonary diseases with hypoxia and hypercapnia, sleep-related non-obstructive alveolar hypoventilation and the congenital central alveolar hypoventilation syndrome.

The compounds of the invention can additionally be used for treatment and/or prevention of neurodegenerative disor-

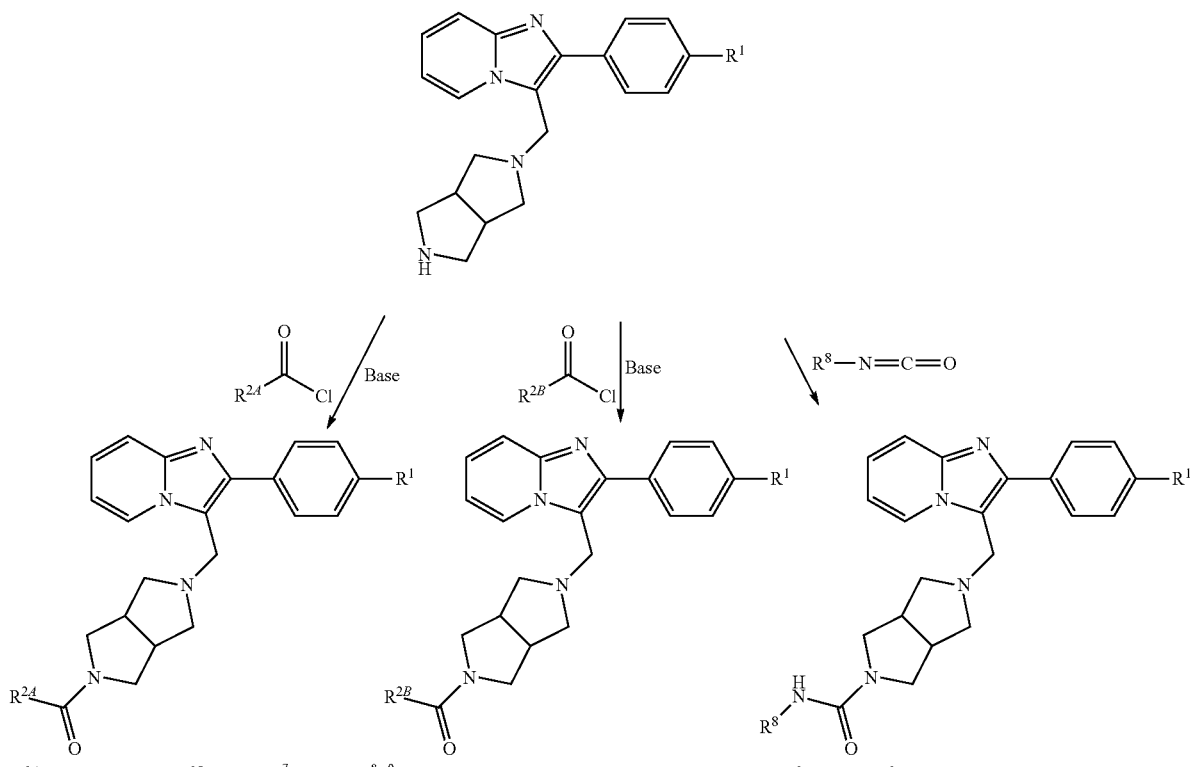

Scheme 2

[$R^{2A}$: see under scheme 1; $R^{2B}$ = —$OR^7$ or —$NR^8R^9$ (as described above as part of the scope of the definition of $R^2$, but where $R^9$ here is not hydrogen)].

The compounds of the invention have valuable pharmacological properties and can be used for prevention and treatment of diseases in humans and animals.

The compounds of the invention are potent and selective blockers of TASK-1 and TASK-3 channels and are therefore suitable for the treatment and/or prevention of disorders and pathological processes, in particular those caused by activation of TASK-1 and/or TASK-3 or by activated TASK-1 and/or TASK-3, and of disorders secondary to damage caused by TASK-1 and/or TASK-3.

For the purposes of the present invention, this includes in particular disorders from the group of the respiratory disorders and sleep-related respiratory disorders, such as obstrucders such as dementia, dementia with Lewy bodies, Alzheimer's disease, Parkinson's disease, Huntington's disease, Pick's disease, Wilson's disease, progressive supranuclear paresis, corticobasal degeneration, tauopathy, frontotemporal dementia and parkinsonism linked to chromosome 17, multisystem atrophy, spinocerebellar ataxias, spinobulbar muscular atrophy of the Kennedy type, Friedreich's ataxia, dentatorubral-pallidoluysian atrophy, amyotrophic lateral sclerosis, primary lateral sclerosis, spinal muscular atrophy, Creutzfeldt-Jakob disease and variants of Creutzfeldt-Jakob disease, infantile neuroaxonal dystrophy, neurodegeneration with brain iron accumulation, frontotemporal lobar degeneration with ubiquitin proteasome system and familial encephalopathy with neuroserpin inclusions.

In addition, the compounds of the invention can be used for treatment and/or prevention of neuroinflammatory and neuroimmunological disorders of the central nervous system (CNS), for example multiple sclerosis (Encephalomyelitis disseminata), transverse myelitis, Neuromyelitis optica, acute disseminated encephalomyelitis, optic neuritis, meningitis, encephalitis, demyelinating diseases and also inflammatory vascular changes in the central nervous system.

Moreover, the compounds of the invention are suitable for the treatment and/or prevention of neoplastic disorders such as, for example, skin cancer, breast cancer, lung cancer, colon cancer and prostate cancer.

The compounds of the invention are also suitable for treatment and/or prevention of cardiac arrhythmias, for example atrial and ventricular arrhythmias, conduction defects such as first- to third-degree atrio-ventricular blocks, supraventricular tachyarrhythmia, atrial fibrillation, atrial flutter, ventricular fibrillation, ventricular flutter, ventricular tachyarrhythmia, Torsade de pointes tachycardia, atrial and ventricular extrasystoles, AV-junctional extrasystoles, sick sinus syndrome, syncopes and AV nodal re-entrant tachycardia.

Further cardiovascular disorders where the compounds of the invention can be employed for treatment and/or prevention are, for example, heart failure, coronary heart disease, stable and unstable angina pectoris, high blood pressure (hypertension), pulmonary-arterial hypertension (PAH) and other forms of pulmonary hypertension (PH), renal hypertension, peripheral and cardial vascular disorders, Wolff-Parkinson-White syndrome, acute coronary syndrome (ACS), autoimmune cardiac disorders (pericarditis, endocarditis, valvolitis, aortitis, cardiomyopathies), boxer cardiomyopathy, aneurysms, shock such as cardiogenic shock, septic shock and anaphylactic shock, furthermore thromboembolic disorders and ischemias such as myocardial ischemia, myocardial infarction, stroke, cardiac hypertrophy, transient and ischemic attacks, preeclampsia, inflammatory cardiovascular disorders, spasms of the coronary arteries and peripheral arteries, edema formation such as, for example, pulmonary edema, cerebral edema, renal edema or edema caused by heart failure, peripheral circulatory disturbances, reperfusion damage, arterial and venous thromboses, microalbuminuria, myocardial insufficiency, endothelial dysfunction, micro- and macrovascular damage (vasculitis), and also to prevent restenoses, for example after thrombolysis therapies, percutaneous transluminal angioplasties (PTA), percutaneous transluminal coronary angioplasties (PTCA), heart transplants and bypass operations.

In the context of the present invention, the term "heart failure" encompasses both acute and chronic forms of heart failure, and also specific or related disease types thereof, such as acute decompensated heart failure, right heart failure, left heart failure, global failure, ischaemic cardiomyopathy, dilatative cardiomyopathy, hypertrophic cardiomyopathy, idiopathic cardiomyopathy, congenital heart defects, heart valve defects, heart failure associated with heart valve defects, mitral valve stenosis, mitral valve insufficiency, aortic valve stenosis, aortic valve insufficiency, tricuspid valve stenosis, tricuspid valve insufficiency, pulmonary valve stenosis, pulmonary valve insufficiency, combined heart valve defects, myocardial inflammation (myocarditis), chronic myocarditis, acute myocarditis, viral myocarditis, diabetic heart failure, alcoholic cardiomyopathy, cardiac storage disorders and diastolic and systolic heart failure.

The compounds of the invention can additionally be used for treatment and/or prevention of asthmatic disorders of varying severity with intermittent or persistent characteristics (refractive asthma, bronchial asthma, allergic asthma, intrinsic asthma, extrinsic asthma, medicament- or dust-induced asthma), of various forms of bronchitis (chronic bronchitis, infectious bronchitis, eosinophilic bronchitis), of bronchiectasis, pneumonia, farmer's lung and related disorders, coughs and colds (chronic inflammatory cough, iatrogenic cough), inflammation of the nasal mucosa (including medicament-related rhinitis, vasomotoric rhinitis and seasonal allergic rhinitis, for example hay fever) and of polyps.

The compounds of the invention are also suitable for treatment and/or prevention of renal disorders, in particular renal insufficiency and kidney failure. In the context of the present invention, the terms "renal insufficiency" and "kidney failure" encompass both acute and chronic manifestations thereof and also underlying or related renal disorders such as renal hypoperfusion, intradialytic hypotension, obstructive uropathy, glomerulopathies, glomerulonephritis, acute glomerulonephritis, glomerulosclerosis, tubulointerstitial diseases, nephropathic disorders such as primary and congenital kidney disease, nephritis, immunological kidney disorders such as kidney transplant rejection and immuno-complex-induced kidney disorders, nephropathy induced by toxic substances, nephropathy induced by contrast agents, diabetic and non-diabetic nephropathy, pyelonephritis, renal cysts, nephrosclerosis, hypertensive nephrosclerosis and nephrotic syndrome which can be characterized diagnostically, for example by abnormally reduced creatinine and/or water excretion, abnormally elevated blood concentrations of urea, nitrogen, potassium and/or creatinine, altered activity of renal enzymes, for example glutamyl synthetase, altered urine osmolarity or urine volume, elevated microalbuminuria, macroalbuminuria, lesions on glomerulae and arterioles, tubular dilatation, hyperphosphatemia and/or need for dialysis. The present invention also encompasses the use of the compounds of the invention for treatment and/or prevention of sequelae of renal insufficiency, for example hypertension, pulmonary edema, heart failure, uremia, anemia, electrolyte disturbances (for example hyperkalemia, hyponatremia) and disturbances in bone and carbohydrate metabolism.

In addition, the compounds of the invention are suitable for treatment and/or prevention of disorders of the urogenital system, for example benign prostate syndrome (BPS), benign prostate hyperplasia (BPH), benign prostate enlargement (BPE), bladder outlet obstruction (BOO), lower urinary tract syndromes (LUTS), neurogenic overactive bladder (OAB), incontinence, for example mixed urinary incontinence, urge urinary incontinence, stress urinary incontinence or overflow urinary incontinence (MUI, UUI, SUI, OUI), pelvic pain, and also erectile dysfunction and female sexual dysfunction.

The compounds of the invention are further suitable for treatment and/or prevention of inflammatory disorders and autoimmune disorders such as, for example, rheumatoid disorders, inflammatory eye disorders, chronic obstructive pulmonary disease (COPD), acute respiratory distress syndrome (ARDS), acute lung injury (ALI), alpha-1-antitrypsin deficiency (AATD), pulmonary emphysema (e.g. pulmonary emphysema induced by cigarette smoke), cystic fibrosis (CF), sepsis (SIRS), multiple organ failure (MODS, MOF), inflammatory disorders of the kidney, chronic intestinal inflammations (IBD, Crohn's disease, ulcerative colitis), pancreatitis, peritonitis, cystitis, urethritis, prostatitis, epidimytitis, oophoritis, salpingitis and vulvovaginitis, and also for the treatment and/or prevention of fibrotic disorders of internal organs such as, for example, the lung, the heart, the kidney, the bone marrow and especially the liver, of dermatological fibroses and of fibrotic disorders of the eye. In the context of the present invention, the term "fibrotic disorders" includes in particular disorders such as hepatic fibrosis, cirrhosis of the liver, pulmonary fibrosis, endomyocardial fibrosis, nephropathy, glomerulonephritis, interstitial renal fibrosis, fibrotic damage resulting from diabetes, bone marrow fibrosis, peritoneal fibrosis and similar fibrotic disorders, scleroderma, morphea, keloids, hypertrophic scarring, nevi, diabetic retinopathy, proliferative vitroretinopathy and disorders of the connective tissue (for example sarcoidosis). The compounds of the invention can likewise be used for promotion of wound healing, for controlling postoperative scarring, for example following glaucoma operations and cosmetically for aging or keratinized skin.

In addition, the compounds of the invention can be used for treatment and/or prevention of arteriosclerosis, impaired lipid metabolism and dyslipidemias (hypolipoproteinemia, hypertriglyceridemia, hyperlipidemia, combined hyperlipidemias, hypercholesterolemia, abetalipoproteinemia, sitosterolemia), xanthomatosis, Tangier disease, adiposity, obesity, metabolic disorders (metabolic syndrome, hyperglycemia, insulin-dependent diabetes, non-insulin-dependent diabetes, gestation diabetes, hyperinsulinemia, insulin resistance, glucose intolerance and diabetic sequelae, such as retinopathy, nephropathy and neuropathy), of anemias such as hemolytic anemias, in particular hemoglobinopathies such as sickle cell anemia and thalassemias, megaloblastic anemias, iron deficiency anemias, anemias owing to acute blood loss, displacement anemias and aplastic anemias, of disorders of the gastrointestinal tract and the abdomen (glossitis, gingivitis, periodontitis, esophagitis, eosinophilic gastroenteritis, mastocytosis, Crohn's disease, colitis, proctitis, anus pruritis, diarrhea, celiac disease, hepatitis, hepatic fibrosis, cirrhosis of the liver, pancreatitis and cholecystitis), of disorders of the central nervous system (stroke, epilepsy, depression), immune disorders, thyroid disorders (hyperthyreosis), skin disorders (psoriasis, acne, eczema, neurodermatitis, various forms of dermatitis, keratitis, bullosis, vasculitis, cellulitis, panniculitis, lupus erythematosus, erythema, lymphomas, skin cancer, Sweet syndrome, Weber-Christian syndrome, scar formation, wart formation, chilblains), of inflammatory eye diseases (saccoidosis, blepharitis, conjunctivitis, iritis, uveitis, chorioiditis, ophthalmitis), of viral diseases (caused by influenza, adeno and corona viruses, for example HPV, HCMV, HIV, SARS), of disorders of the skeletal bone and the joints and also the skeletal muscle, of inflammatory arterial lesions (various forms of arteritis, for example endarteritis, mesarteritis, periarteritis, panarteritis, arteritis rheumatica, arteritis deformans, arteritis temporalis, arteritis cranialis, arteritis gigantocellularis and arteritis granulomatosa, and also Horton syndrome, Churg-Strauss syndrome and Takayasu arteritis), of Muckle-Well syndrome, of Kikuchi disease, of polychondritis, dermatosclerosis and also other disorders having an inflammatory or immunological component, for example cataract, cachexia, osteoporosis, gout, incontinence, leprosy, Sezary syndrome and paraneoplastic syndrome, in the event of rejection reactions after organ transplants and for wound healing and angiogenesis particularly in the case of chronic wounds.

By virtue of their property profile, the compounds of the invention are preferably suitable for treatment and/or prevention of respiratory disorders, in particular of sleep-related respiratory disorders such as obstructive and central sleep apneas and also primary and obstructive snoring, for treatment and/or prevention of cardiac arrhythmias and also for treatment and/or prevention of neurodegenerative, neuroinflammatory and neuroimmunological disorders.

The aforementioned well-characterized diseases in humans can also occur with comparable etiology in other mammals and can likewise be treated therein with the compounds of the present invention.

In the context of the present invention, the term "treatment" or "treating" includes inhibition, retardation, checking, alleviating, attenuating, restricting, reducing, suppressing, repelling or healing of a disease, a condition, a disorder, an injury or a health problem, or the development, the course or the progression of such states and/or the symptoms of such states. The term "therapy" is understood here to be synonymous with the term "treatment".

The terms "prevention", "prophylaxis" and "preclusion" are used synonymously in the context of the present invention and refer to the avoidance or reduction of the risk of contracting, experiencing, suffering from or having a disease, a condition, a disorder, an injury or a health problem, or a development or advancement of such states and/or the symptoms of such states.

The treatment or prevention of a disease, a condition, a disorder, an injury or a health problem may be partial or complete.

The present invention thus further provides for the use of the compounds of the invention for treatment and/or prevention of disorders, especially of the aforementioned disorders.

The present invention further provides for the use of the compounds of the invention for production of a medicament for treatment and/or prevention of disorders, especially of the aforementioned disorders.

The present invention further provides a medicament comprising at least one of the compounds of the invention for treatment and/or prevention of disorders, especially of the aforementioned disorders.

The present invention further provides for the use of the compounds of the invention in a method for treatment and/or prevention of disorders, especially of the aforementioned disorders.

The present invention further provides a process for treatment and/or prevention of disorders, especially of the aforementioned disorders, using an effective amount of at least one of the compounds of the invention.

The compounds of the invention can be used alone or, if required, in combination with one or more other pharmacologically active substances, provided that this combination does not lead to undesirable and unacceptable side effects. The present invention therefore further provides medicaments comprising at least one of the compounds of the invention and one or more further drugs, especially for treatment and/or prevention of the aforementioned disorders. Preferred examples of combination active ingredients suitable for this purpose include:

respiratory stimulants such as, by way of example and with preference, theophylline, doxapram, nikethamide or caffeine;

psychostimulants, by way of example and with preference modafinil or armodafinil;

amphetamines and amphetamine derivatives, by way of example and with preference amphetamine, metamphetamine or methylphenidate;

serotonin reuptake inhibitors, by way of example and with preference fluoxetine, paroxetine, citalopram, escitalopram, sertraline, fluvoxamine or trazodone;

serotonin precursors, by way of example and with preference L-tryptophan;
selective serotonin noradrenaline reuptake inhibitors, by way of example and with preference venlafaxine or duloxetine;
noradrenergic and specifically serotonergic antidepressants, by way of example and with preference mirtazapine;
selective noradrenaline reuptake inhibitors, by way of example and with preference reboxetine;
tricyclic antidepressants, by way of example and with preference amitriptyline, protriptyline, doxepine, trimipramine, imipramine, clomipramine or desipramine;
alpha2-adrenergic agonists, by way of example and with preference clonidine;
GABA agonists, by way of example and with preference baclofen;
alpha sympathomimetics, by way of example and with preference xylometazoline, oxymetazoline, phenylephrine, naphazoline, tetryzoline or tramazoline;
glucocorticoids, by way of example and with preference fluticasone, budesonide, beclometasone, mometasone, tixocortol or triamcinolone;
cannabinoid receptor agonists;
carboanhydrase inhibitors, by way of example and with preference acetazolamide, methazolamide or diclofenamide;
opioid and benzodiazepine receptor antagonists, by way of example and with preference flumazenil, naloxone or naltrexone;
cholinesterase inhibitors, by way of example and with preference neostigmine, pyridostigmine, physostigmine, donepezil, galantamine or rivastigmine;
N-methyl-D-aspartate and glutamate antagonists, by way of example and with preference amantadine, memantine or sabeluzole;
nicotine receptor agonists;
leukotriene receptor antagonists, by way of example and with preference montelukast or tripelukast;
dopamine receptor antagonists, by way of example and with preference dromperidone, metoclopramide or benzamide, butyrophenone or phenothiazine derivatives;
appetite suppressants, by way of example and with preference sibutramine, topiramate, phentermine, lipase inhibitors or cannabinoid receptor antagonists;
proton pump inhibitors, by way of example and with preference pantoprazole, omeprazole, esomeprazole, lansoprazole or rabeprazole;
organic nitrates and NO donors, for example sodium nitroprusside, nitroglycerin, isosorbide mononitrate, isosorbide dinitrate, molsidomine or SIN-1, and inhaled NO;
compounds which inhibit the degradation of cyclic guanosine monophosphate (cGMP) and/or cyclic adenosine monophosphate (cAMP), for example inhibitors of phosphodiesterases (PDE) 1, 2, 3, 4 and/or 5, especially PDE 5 inhibitors such as sildenafil, vardenafil, tadalafil, udenafil, dasantafil, avanafil, mirodenafil or lodenafil;
NO- and hem-independent activators of soluble guanylate cyclase (sGC), such as in particular the compounds described in WO 01/19355, WO 01/19776, WO 01/19778, WO 01/19780, WO 02/070462 and WO 02/070510;
NO-independent but hem-dependent stimulators of soluble guanylate cyclase (sGC), such as in particular riociguat, vericiguat and the compounds described in WO 00/06568, WO 00/06569, WO 02/42301, WO 03/095451, WO 2011/147809, WO 2012/004258, WO 2012/028647 and WO 2012/059549;
prostacyclin analogues and IP receptor agonists, by way of example and with preference iloprost, beraprost, treprostinil, epoprostenol or selexipag;
endothelin receptor antagonists, by way of example and with preference bosentan, darusentan, ambrisentan or sitaxsentan;
compounds which inhibit human neutrophile elastase (HNE), by way of example and with preference sivelestat or DX-890 (reltran);
compounds which inhibit the degradation and alteration of the extracellular matrix, by way of example and with preference inhibitors of the matrix metalloproteases (MMPs), especially inhibitors of stromelysin, collagenases, gelatinases and aggrecanases (in this context particularly of MMP-1, MMP-3, MMP-8, MMP-9, MMP-10, MMP-11 and MMP-13) and of metalloelastase (MMP-12);
compounds which block the binding of serotonin to its receptors, by way of example and with preference antagonists of the 5-HT$_{2B}$ receptor such as PRX-08066;
antagonists of growth factors, cytokines and chemokines, by way of example and with preference antagonists of TGF-β, CTGF, IL-1, IL-4, IL-5, IL-6, IL-8, IL-13 and integrins;
Rho kinase-inhibiting compounds, by way of example and with preference fasudil, Y-27632, SLx-2119, BF-66851, BF-66852, BF-66853, KI-23095 or BA-1049;
compounds which influence the energy metabolism of the heart, by way of example and with preference etomoxir, dichloroacetate, ranolazine or trimetazidine;
compounds which inhibit the signal transduction cascade, by way of example and with preference from the group of the kinase inhibitors, in particular from the group of the tyrosine kinase and/or serine/threonine kinase inhibitors, by way of example and with preference nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;
anti-obstructive agents as used, for example, for treatment of chronic obstructive pulmonary disease (COPD) or bronchial asthma, by way of example and with preference from the group of the inhalatively or systemically administered agonists of the beta-adrenergic receptor (beta-mimetics) and the inhalatively administered anti-muscarinergic substances;
antiinflammatory, immunomodulating, immunosuppressive and/or cytotoxic agents, by way of example and with preference from the group of the systemically or inhalatively administered corticosteroids and also dimethyl fumarate, fingolimod, glatiramer acetate, 3-interferons, natalizumab, teriflunomide, mitoxantrone, immunoglobulins, acetylcysteine, montelukast, tripelukast, azathioprine, cyclophosphamide, hydroxycarbamide, azithromycin, interferon-γ, pirfenidone or etanercept;
antifibrotic agents, by way of example and with preference lysophosphatidic acid receptor 1 (LPA-1) antagonists, CTGF inhibitors, IL-4 antagonists, IL-13 antagonists, TGF-β antagonists or pirfenidone;

antithrombotic agents, by way of example and with preference from the group of platelet aggregation inhibitors, the anticoagulants and the profibrinolytic substances;

hypotensive active ingredients, by way of example and with preference from the group of the calcium antagonists, angiotensin AII antagonists, ACE inhibitors, vasopeptidase inhibitors, endothelin antagonists, renin inhibitors, alpha receptor blockers, beta receptor blockers, mineralocorticoid receptor antagonists and also the diuretics; and/or active ingredients that alter lipid metabolism, by way of example and with preference from the group of the thyroid receptor agonists, cholesterol synthesis inhibitors, by way of example and preferably, HMG-CoA reductase inhibitors or squalene synthesis inhibitors, the ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

In a preferred embodiment of the invention, the compounds of the invention are administered in combination with a beta-adrenergic receptor agonist, by way of example and with preference albuterol, isoproterenol, metaproterenol, terbutalin, fenoterol, formoterol, reproterol, salbutamol or salmeterol.

In a preferred embodiment of the invention, the compounds of the invention are administered in combination with an antimuscarinergic substance, by way of example and with preference ipratropium bromide, tiotropium bromide or oxitropium bromide.

In a preferred embodiment of the invention, the compounds of the invention are administered in combination with a corticosteroid, by way of example and with preference prednisone, prednisolone, methylprednisolone, triamcinolone, dexamethasone, betamethasone, beclomethasone, flunisolide, budesonide or fluticasone.

Antithrombotic agents are preferably understood to mean compounds from the group of the platelet aggregation inhibitors, the anticoagulants and the profibrinolytic substances.

In a preferred embodiment of the invention, the compounds of the invention are administered in combination with a platelet aggregation inhibitor, by way of example and with preference aspirin, clopidogrel, ticlopidine or dipyridamole.

In a preferred embodiment of the invention, the compounds of the invention are administered in combination with a thrombin inhibitor, by way of example and with preference ximelagatran, melagatran, dabigatran, bivalirudin or clexane.

In a preferred embodiment of the invention, the compounds of the invention are administered in combination with a GPIIb/IIIa antagonist, by way of example and with preference tirofiban or abciximab.

In a preferred embodiment of the invention, the compounds of the invention are administered in combination with a factor Xa inhibitor, by way of example and with preference rivaroxaban, apixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds of the invention are administered in combination with heparin or with a low molecular weight (LMW) heparin derivative.

In a preferred embodiment of the invention, the compounds of the invention are administered in combination with a vitamin K antagonist, by way of example and with preference coumarin.

Hypotensive agents are preferably understood to mean compounds from the group of the calcium antagonists, angiotensin AII antagonists, ACE inhibitors, endothelin antagonists, renin inhibitors, alpha receptor blockers, beta receptor blockers, mineralocorticoid receptor antagonists, and the diuretics.

In a preferred embodiment of the invention, the compounds of the invention are administered in combination with a calcium antagonist, by way of example and with preference nifedipine, amlodipine, verapamil or diltiazem.

In a preferred embodiment of the invention, the compounds of the invention are administered in combination with an alpha-1 receptor blocker, by way of example and with preference prazosin.

In a preferred embodiment of the invention, the compounds of the invention are administered in combination with a beta receptor blocker, by way of example and with preference propranolol, atenolol, timolol, pindolol, alprenolol, oxprenolol, penbutolol, bupranolol, metipranolol, nadolol, mepindolol, carazalol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the inventive compounds are administered in combination with an angiotensin AII antagonist, preferred examples being losartan, candesartan, valsartan, telmisartan or embusartan.

In a preferred embodiment of the invention, the compounds of the invention are administered in combination with an ACE inhibitor, by way of example and with preference enalapril, captopril, lisinopril, ramipril, delapril, fosinopril, quinopril, perindopril or trandopril.

In a preferred embodiment of the invention, the compounds of the invention are administered in combination with an endothelin antagonist, by way of example and with preference bosentan, darusentan, ambrisentan or sitaxsentan.

In a preferred embodiment of the invention, the compounds of the invention are administered in combination with a renin inhibitor, by way of example and with preference aliskiren, SPP-600 or SPP-800.

In a preferred embodiment of the invention, the compounds of the invention are administered in combination with a mineralocorticoid receptor antagonist, by way of example and with preference spironolactone, eplerenone or finerenone.

In a preferred embodiment of the invention, the compounds of the invention are administered in combination with a diuretic, by way of example and with preference furosemide, bumetanide, torsemide, bendroflumethiazide, chlorothiazide, hydrochlorothiazide, hydroflumethiazide, methyclothiazide, polythiazide, trichlormethiazide, chlorthalidone, indapamide, metolazone, quinethazone, acetazolamide, dichlorphenamide, methazolamide, glycerol, isosorbide, mannitol, amiloride or triamterene.

Lipid metabolism modifiers are preferably understood to mean compounds from the group of the CETP inhibitors, thyroid receptor agonists, cholesterol synthesis inhibitors such as HMG-CoA reductase inhibitors or squalene synthesis inhibitors, the ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and the lipoprotein(a) antagonists.

In a preferred embodiment of the invention, the compounds of the invention are administered in combination with a CETP inhibitor, by way of example and with preference torcetrapib (CP-529 414), JJT-705 or CETP vaccine (Avant).

In a preferred embodiment of the invention, the compounds of the invention are administered in combination with a thyroid receptor agonist, by way of example and with preference D-thyroxine, 3,5,3'-triiodothyronine (T3), CGS 23425 or axitirome (CGS 26214).

In a preferred embodiment of the invention, the compounds of the invention are administered in combination with an HMG-CoA reductase inhibitor from the class of statins, by way of example and with preference lovastatin, simvastatin, pravastatin, fluvastatin, atorvastatin, rosuvastatin or pitavastatin.

In a preferred embodiment of the invention, the compounds of the invention are administered in combination with a squalene synthesis inhibitor, by way of example and with preference BMS-188494 or TAK-475.

In a preferred embodiment of the invention, the compounds of the invention are administered in combination with an ACAT inhibitor, by way of example and with preference avasimibe, melinamide, pactimibe, eflucimibe or SMP-797.

In a preferred embodiment of the invention, the compounds of the invention are administered in combination with an MTP inhibitor, by way of example and with preference implitapide, BMS-201038, R-103757 or JTT-130.

In a preferred embodiment of the invention, the compounds of the invention are administered in combination with a PPAR-gamma agonist, by way of example and with preference pioglitazone or rosiglitazone.

In a preferred embodiment of the invention, the compounds of the invention are administered in combination with a PPAR-delta agonist, by way of example and with preference GW 501516 or BAY 68-5042.

In a preferred embodiment of the invention, the compounds of the invention are administered in combination with a cholesterol absorption inhibitor, by way of example and with preference ezetimibe, tiqueside or pamaqueside.

In a preferred embodiment of the invention, the compounds of the invention are administered in combination with a lipase inhibitor, by way of example and with preference orlistat.

In a preferred embodiment of the invention, the compounds of the invention are administered in combination with a polymeric bile acid adsorber, by way of example and with preference cholestyramine, colestipol, colesolvam, CholestaGel or colestimide.

In a preferred embodiment of the invention, the compounds of the invention are administered in combination with a bile acid reabsorption inhibitor, by way of example and with preference ASBT (=IBAT) inhibitors, for example AZD-7806, S-8921, AK-105, BARI-1741, SC-435 or SC-635.

In a preferred embodiment of the invention, the compounds of the invention are administered in combination with a lipoprotein(a) antagonist, by way of example and with preference gemcabene calcium (CI-1027) or nicotinic acid.

Particular preference is given to combinations of the compounds of the invention with one or more further active ingredients selected from the group consisting of respiratory stimulants, psychostimulants, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

If required, the substances of the invention can also be employed in conjunction with the use of one or more medical technical devices or auxiliaries, provided that this does not lead to unwanted and unacceptable side-effects. Medical devices and auxiliaries suitable for such a combined application are, by way of example and with preference:

devices for positive airway pressure ventilation, by way of example and with preference CPAP (continuous positive airway pressure) devices, BiPAP (bilevel positive airway pressure) devices and IPPV (intermittent positive pressure ventilation) devices;

neurostimulators of the *Nervus hypoglossus*;

intraoral auxiliaries, by way of example and with preference protrusion braces;

nasal disposable valves;

nasal stents.

The present invention further provides medicaments which comprise at least one compound of the invention, typically together with one or more inert, non-toxic, pharmaceutically suitable excipients, and for the use thereof for the aforementioned purposes.

The compounds according to the invention can act systemically and/or locally. For this purpose, they can be administered in a suitable manner, for example by the oral, parenteral, pulmonal, intrapulmonal (inhalative), nasal, intranasal, pharyngeal, lingual, sublingual, buccal, rectal, dermal, transdermal, conjunctival or otic route, or as an implant or stent.

The compounds according to the invention can be administered in administration forms suitable for these administration routes.

Suitable administration forms for oral administration are those which work according to the prior art and release the compounds of the invention rapidly and/or in a modified manner and which contain the compounds of the invention in crystalline and/or amorphized and/or dissolved form, for example tablets (uncoated or coated tablets, for example with gastric juice-resistant or retarded-dissolution or insoluble coatings which control the release of the compound of the invention), tablets or films/oblates which disintegrate rapidly in the oral cavity, films/lyophilizates, capsules (for example hard or soft gelatin capsules), sugar-coated tablets, granules, pellets, powders, emulsions, suspensions, aerosols or solutions.

Parenteral administration can bypass an absorption step (e.g. take place intravenously, intraarterially, intracardially, intraspinally or intralumbally) or include an absorption (e.g. take place inhalatively, intramuscularly, subcutaneously, intracutaneously, percutaneously or intraperitoneally). Administration forms suitable for parenteral administration include inter alia preparations for injection and infusion in the form of solutions, suspensions, emulsions, lyophilizates or sterile powders.

For the other administration routes, suitable examples are inhalable medicament forms (including powder inhalers, nebulizers, metered aerosols), nasal drops, solutions or sprays, throat sprays, tablets, films/oblates or capsules for lingual, sublingual or buccal administration, suppositories, ear or eye preparations, vaginal capsules, aqueous suspensions (lotions, shaking mixtures), lipophilic suspensions, ointments, creams, transdermal therapeutic systems (e.g. patches), milk, pastes, foams, sprinkling powders, implants or stents.

Preference is given to oral, intravenous, intranasal and pharyngeal administration.

In one embodiment, administration is by the intranasal route. In one embodiment, intranasal administration is effected with the aid of nose drops or a nasal spray. In one embodiment, intranasal administration is effected with the aid of a nasal spray.

The compounds according to the invention can be converted to the administration forms mentioned. This can be accomplished in a manner known per se by mixing with inert, non-toxic, pharmaceutically suitable excipients. These excipients include inter alia carriers (for example microcrystalline cellulose, lactose, mannitol), solvents (e.g. liquid polyethylene glycols), emulsifiers and dispersing or wetting agents (for example sodium dodecylsulfate, polyoxysorbitan oleate), binders (for example polyvinylpyrrolidone), synthetic and natural polymers (for example albumin), stabilizers (e.g. antioxidants, for example ascorbic acid), colorants (e.g. inorganic pigments, for example iron oxides) and flavor and/or odor correctors.

In general, it has been found to be advantageous in the case of parenteral administration to administer amounts of about 0.001 to 1 mg/kg, preferably about 0.01 to 0.5 mg/kg body weight to achieve effective results. In the case of oral administration the dosage is about 0.01 to 100 mg/kg, preferably about 0.01 to 20 mg/kg and most preferably 0.1 to 10 mg/kg body weight.

In one embodiment, the dosage in the case of intranasal administration is about 0.1 μg to 500 μg per day. In a further embodiment, the dosage in the case of intranasal administration is about 1 μg to 250 μg per day. In a further embodiment, the dosage in the case of intranasal administration is about 1 μg to 120 μg per day. In a further embodiment, the dose of about 0.1 μg to 500 μg per day, or of about 1 μg to 250 μg per day, or of about 1 μg to 120 μg per day, is administered once daily by the intranasal route before sleeping. In one embodiment, the dose of about 0.1 μg to 500 μg per day, or of about 1 μg to 250 μg per day, or of about 1 μg to 120 μg per day, is administered once daily with half to each nostril. In one embodiment, the dose of about 0.1 μg to 500 μg per day, or of about 1 μg to 250 μg per day, or of about 1 μg to 120 μg per day, is administered once daily with half to each nostril before sleeping.

It may nevertheless be necessary in some cases to deviate from the stated amounts, and specifically as a function of body weight, route of administration, individual response to the active ingredient, nature of the preparation and time at which or interval over which administration takes place. Thus in some cases it may be sufficient to manage with less than the aforementioned minimum amount, while in other cases the upper limit mentioned must be exceeded. In the case of administration of greater amounts, it may be advisable to divide them into several individual doses over the day.

The working examples which follow illustrate the invention. The invention is not restricted to the examples.

A. EXAMPLES

Abbreviations and Acronyms abs. absolute
Ac acetyl
aq. aqueous, aqueous solution
Boc tert-butoxycarbonyl
br. broad (in NMR signal)
Ex. Example
Bu butyl
c concentration
ca. circa, about
cat. catalytic
CI chemical ionization (in MS)
d doublet (in NMR)
d day(s)
DCI direct chemical ionization (in MS)
dd doublet of doublets (in NMR)
DMF N,N-dimethylformamide
DMSO dimethyl sulfoxide
dq doublet of quartets (in NMR)
dt doublet of triplets (in NMR)
d. Th. of theory (in chemical yield)
EI electron impact ionization (in MS)
eq. equivalent(s)
ESI electrospray ionization (in MS)
Et ethyl
h hour(s)
HATU O-(7-azabenzotriazol-1-yl)-N,N,N',N'-tetramethyluronium hexafluorophosphate
HOBt 1-hydroxy-1H-benzotriazole hydrate
HPLC high-pressure, high-performance liquid chromatography
iPr isopropyl
conc. concentrated (in the case of a solution)
LC liquid chromatography
LC-MS liquid chromatography-coupled mass spectrometry
lit. literature (reference)
m multiplet (in NMR)
Me methyl
min minute(s)
MS mass spectrometry
NMR nuclear magnetic resonance spectrometry
Ph phenyl
Pr propyl
q quartet (in NMR)
quant. quantitative (in chemical yield)
RP reverse phase (in HPLC)
RT room temperature
$R_t$ retention time (in HPLC, LC-MS)
s singlet (in NMR)
t triplet (in NMR)
tBu tert-butyl
TFA trifluoroacetic acid
THF tetrahydrofuran
UV ultraviolet spectrometry
v/v volume to volume ratio (of a solution)
tog. together LC-MS and HPLC Methods:

Method 1 (LC-MS):

Instrument: Waters Acquity SQD UPLC System; column: Waters Acquity UPLC HSS T3 1.8 μm, 50 mm×1 mm; mobile phase A: 1 l of water+0.25 ml of 99% strength formic acid, mobile phase B: 1 l of acetonitrile+0.25 ml of 99% strength formic acid; gradient: 0.0 min 90% A→1.2 min 5% A→2.0 min 5% A; temperature: 50° C.; flow rate: 0.40 ml/min; UV detection: 208-400 nm.

Method 2 (LC-MS):

MS instrument: Thermo Scientific FT-MS; instrument UHPLC: Thermo Scientific UltiMate 3000; column: Waters HSS T3 C18 1.8 μm, 75 mm×2.1 mm; mobile phase A: 1 l of water+0.01% formic acid, mobile phase B: 1 l of acetonitrile+0.01% formic acid; gradient: 0.0 min 10% B→2.5 min 95% B→3.5 min 95% B; temperature: 50° C.; flow rate: 0.90 ml/min; UV detection: 210-300 nm.

Method 3 (LC-MS):

MS instrument: Waters Micromass QM; HPLC instrument: Agilent 1100 series; column: Agilent ZORBAX Extend-C18 3.5 μm, 50 mm×3.0 mm; mobile phase A: 1l of water+0.01 mol of ammonium carbonate, mobile phase B: 1l of acetonitrile; gradient: 0.0 min 98% A→0.2 min 98% A→3.0 min 5% A→4.5 min 5% A; temperature: 40° C.; flow rate: 1.75 ml/min; UV detection: 210 nm.

Method 4 (LC-MS):

MS instrument: Waters Micromass Quattro Micro; HPLC instrument: Waters UPLC Acquity; column: Waters BEH C18 1.7 μm, 50 mm×2.1 mm; mobile phase A: 1l of water+0.01 mol of ammonium formate, mobile phase B: 1l of acetonitrile; gradient: 0.0 min 95% A→0.1 min 95% A→2.0 min 15% A→2.5 min 15% A→2.51 min 10% A→3.0 min 10% A; temperature: 40° C.; flow rate: 0.5 ml/min; UV detection: 210 nm.

Method 5 (LC-MS):

Instrument: Agilent MS Quad 6150 with HPLC Agilent 1290; column: Waters Acquity UPLC HSS T3 1.8 μm, 50 mm×2.1 mm; mobile phase A: 1l of water+0.25 ml of 99% strength formic acid, mobile phase B: 1l of acetonitrile+0.25 ml of 99% strength formic acid; gradient: 0.0 min 90% A→0.3 min 90% A→1.7 min 5% A→3.0 min 5% A; flow rate 1.20 ml/min; temperature: 50° C.; UV detection: 205-305 nm.

Method 6 (LC-MS):

MS instrument: Waters SQD; HPLC instrument: Waters UPLC; column: Zorbax SB-Aq (Agilent), 50 mm×2.1 mm, 1.8 μm; mobile phase A: water+0.025% formic acid, mobile phase B: acetonitrile+0.025% formic acid; gradient: 0.0 min 98% A→0.9 min 25% A→1.0 min 5% A→1.4 min 5% A→1.41 min 98% A→1.5 min 98% A; oven: 40° C.; flow rate: 0.60 ml/min; UV detection: DAD, 210 nm.

Method 7 (Preparative HPLC):

Instrument: Abimed Gilson 305; column: Reprosil C18 10 μm, 250 mm×30 mm; mobile phase A: water, mobile phase B: acetonitrile; gradient: 0-3 min 10% B, 3-27 min 10% B→95% B, 27-34.5 min 95% B, 34.5-35.5 min 95% B→10% B, 35.5-36.5 min 10% B; flow rate: 50 ml/min; room temperature; UV detection: 210 nm.

Further Details:

The descriptions of the coupling patterns of $^1$H NMR signals which follow are guided by the visual appearance of the signals in question and do not necessarily correspond to a strict, physically correct interpretation. In general, the stated chemical shift refers to the center of the signal in question; in the case of broad multiplets, an interval is generally given.

Melting points and melting point ranges, if stated, are uncorrected.

In cases where the reaction products were obtained by trituration, stirring or recrystallization, it was frequently possible to isolate further amounts of product from the respective mother liquor by chromatography. However, a description of this chromatography is dispensed with hereinbelow unless a large part of the total yield could only be isolated in this step.

All reactants or reagents whose preparation is not described explicitly hereinafter were purchased commercially from generally accessible sources. For all other reactants or reagents whose preparation is likewise not described hereinafter and which were not commercially obtainable or were obtained from sources which are not generally accessible, a reference is given to the published literature in which their preparation is described.

Starting Compounds and Intermediates

Example 1A 2-(4-Chlorophenyl)imidazo [1,2-a]pyridine

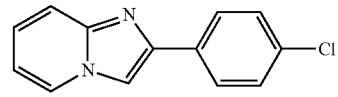 [SMILES: Clc1ccc(-c2cn3ccccc3n2)cc1]

To a solution of 20 g (85.65 mmol) of 2-bromo-1-(4-chlorophenyl)ethanone and 8.87 g (94.22 mmol) of pyridin-2-amine in 200 ml of ethanol were added 10.95 g (130 mmol) of sodium bicarbonate, and the mixture was stirred at 80° C. for 5 hours. The mixture was then cooled, first to room temperature and then to 0° C. (ice bath). The resulting precipitate was filtered off and washed repeatedly with an ethanol/water mixture (2:1). The solid was then dried under vacuum at 40° C. overnight. 19.8 g of the target product were obtained, which was used in subsequent reactions without further purification.

$^1$H-NMR (400 MHz, DMSO-d$_6$, δ/ppm): 6.87-6.94 (m, 1H), 7.23-7.29 (m, 1H), 7.50 (d, 2H), 7.58 (d, 1H), 7.99 (d, 2H), 8.43 (s, 1H), 8.53 (d, 1H).

LC-MS (Method 1): R$_t$=0.58 min; m/z=229/231 (M+H)$^+$.

Analogously to Example 1A, the following compounds were prepared from the reactants specified in each case:

| Example | Name/Structure/Starting materials | Analytical data |
|---|---|---|
| 2A | 2-(4-bromophenyl)imidazo[1,2-a]pyridine<br><br>from 2-bromo-1-(4-bromophenyl)ethanone and pyridin-2-amine | $^1$H-NMR (400 MHz, DMSO-d$_6$, δ/ppm): 6.88-6.94 (m, 1H), 7.23-7.29 (m, 1H), 7.58 (d, 1H), 7.63 (d, 2H), 7.92 (d, 2H), 8.44 (s, 1H), 8.53 (d, 1H).<br>LC-MS (Method 1):<br>R$_t$ = 0.63 min; m/z = 273/275 (M + H)$^+$. |

| Example | Name/Structure/Starting materials | Analytical data |
|---|---|---|
| 3A | 2-(4-fluorophenyl)imidazo[1,2-a]pyridine<br>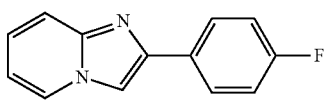<br>from 2-bromo-1-(4-fluorophenyl)ethanone and pyridin-2-amine | $^1$H-NMR (400 MHz, DMSO-$d_6$, δ/ppm): 6.90 (t, 1H), 7.20-7.32 (m, 3H), 7.57 (d, 1H), 8.00 (dd, 2H), 8.38 (s, 1H), 8.52 (d, 1H).<br>LC-MS (Method 1):<br>$R_t$ = 0.49 min; m/z = 213 (M + H)$^+$. |
| 4A | 2-(4-isopropylphenyl)imidazo[1,2-a]pyridine<br>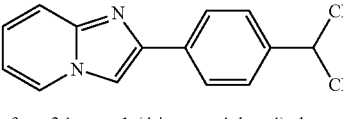<br>from 2-bromo-1-(4-isopropylphenyl)ethanone and pyridin-2-amine | $^1$H-NMR (400 MHz, DMSO-$d_6$, δ/ppm): 1.23 (d, 6H), 2.85-2.96 (m, 1H), 6.88 (t, 1H), 7.19-7.26 (m, 1H), 7.31 (d, 2H), 7.56 (d, 1H), 7.88 (d, 2H), 8.34 (s, 1H), 8.51 (d, 1H).<br>LC-MS (Method 1):<br>$R_t$ = 0.68 min; m/z = 237 (M + H)$^+$. |
| 5A | 2-(4-methylphenyl)imidazo[1,2-a]pyridine<br>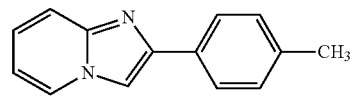<br>from 2-bromo-1-(4-methylphenyl)ethanone and pyridin-2-amine | $^1$H-NMR (400 MHz, DMSO-$d_6$, δ/ppm): 2.33 (s, 3H), 6.88 (t, 1H), 7.18-7.29 (m, 3H), 7.55 (d, 1H), 7.85 (d, 2H), 8.34 (s, 1H), 8.50 (d, 1H).<br>LC-MS (Method 1):<br>$R_t$ = 0.49 min; m/z = 209 (M + H)$^+$. |
| 6A | 4-(imidazo[1,2-a]pyridin-2-yl)benzonitrile<br>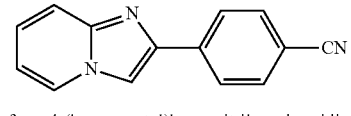<br>from 4-(bromoacetyl)benzonitrile and pyridin-2-amine | $^1$H-NMR (400 MHz, DMSO-$d_6$, δ/ppm): 6.94 (t, 1H), 7.30 (dd, 1H), 7.61 (d, 1H), 7.90 (d, 2H), 8.15 (d, 2H), 8.56 (d, 1H), 8.59 (s, 1H).<br>LC-MS (Method 1):<br>$R_t$ = 0.51 min; m/z = 220 (M + H)$^+$. |

Example 7A 2-(4-tert-Butylphenyl)imidazo [1,2-a]pyridine

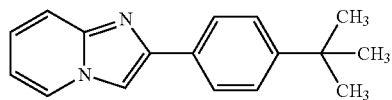

A mixture of 1 g (5.67 mmol) of 1-(4-tert-butylphenyl)ethanone, 1.23 g (13.05 mmol) of pyridin-2-amine and 1.728 g (6.81 mmol) of iodine was stirred at a temperature of 120° C. for 2 hours. 15 ml of water and 8.51 ml of 1 N aqueous sodium hydroxide solution were then added, and the mixture was stirred at 100° C. for a further hour. After cooling to room temperature, about 100 ml of water and about 100 ml of ethyl acetate were added. After separation of the phases, the organic phase was washed twice with water, dried over magnesium sulfate, filtered and concentrated to dryness under reduced pressure. The resulting residue was applied to silica gel and purified by column chromatography on silica gel (Biotage 100 g KP-sil; flow rate: 100 ml/min; mobile phase gradient: 1.3 min cyclohexane/ethyl acetate 92:8→over 13 min to cyclohexane/ethyl acetate 34:66→2.6 min cyclohexane/ethyl acetate 34:66). This gave 970 mg (3.87 mmol, 68% of theory) of the target compound.

$^1$H-NMR (400 MHz, DMSO-$d_6$, δ/ppm): 1.32 (s, 9H), 6.88 (t, 1H), 7.19-7.26 (m, 1H), 7.46 (d, 2H), 7.57 (d, 1H), 7.88 (d, 2H), 8.34 (s, 1H), 8.51 (d, 1H).

LC-MS (Method 1): $R_t$=0.72 min; m/z=251 (M+H)$^+$.

Example 8A 2-(4-Chlorophenyl)imidazo[1,2-a]pyridine-3-carbaldehyde

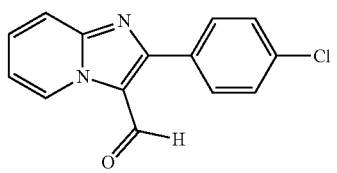 [SMILES: O=Cc1c(-c2ccc(Cl)cc2)nc2ccccn12]

300 ml of DMF were cooled to 0° C. 44 ml (470.08 mmol) of phosphorus oxychloride were then slowly added dropwise. The reaction solution was then slowly warmed to room temperature and stirred at this temperature for an hour. 43 g (188.03 mmol) of 2-(4-chlorophenyl)imidazo[1,2-a]pyridine were then added in portions. During the addition, the reaction solution warmed to 35° C. After the addition had ended, the reaction mixture was heated to 80° C. and stirred at this temperature for 2 hours. After cooling to room temperature, the solution was slowly added to 3 liters of ice-water. The resulting solid was filtered off with suction, washed repeatedly with water and dried in a high-vacuum drying cabinet at 40° C. overnight. This gave 39.6 g (154.27 mmol, 82% of theory) of the target product.

$^1$H-NMR (400 MHz, DMSO-d$_6$, δ/ppm): 7.37 (t, 1H), 7.63 (d, 2H), 7.78 (t, 1H), 7.90-7.99 (m, 3H), 9.58 (d, 1H), 10.02 (s, 1H).

LC-MS (Method 1): R$_t$=0.97 min; m/z=257/259 (M+H)$^+$.

Analogously to Example 8A, the following compounds were prepared from the starting material specified in each case:

| Example | Name/Structure/Starting material | Analytical data |
|---|---|---|
| 9A | 2-(4-bromophenyl)imidazo[1,2-a]pyridine-3-carbaldehyde<br><br>from 2-(4-bromophenyl)imidazo[1,2-a]pyridine | $^1$H-NMR (400 MHz, DMSO-d$_6$, δ/ppm): 7.35 (t, 1H), 7.72-7.80 (m, 3H), 7.85-7.95 (m, 3H), 9.58 (d, 1H), 10.02 (s, 1H).<br>LC-MS (Method 2): R$_t$ = 1.76 min; m/z = 301/303 (M + H)$^+$. |
| 10A | 2-(4-fluorophenyl)imidazo[1,2-a]pyridine-3-carbaldehyde<br><br>from 2-(4-fluorophenyl)imidazo[1,2-a]pyridine | $^1$H-NMR (400 MHz, DMSO-d$_6$, δ/ppm): 7.32-7.45 (m, 3H), 7.77 (t, 1H), 7.92 (d, 1H), 7.99 (dd, 2H), 9.58 (d, 1H), 10.01 (s, 1H).<br>LC-MS (Method 1): R$_t$ = 0.79 min; m/z = 241 (M + H)$^+$. |
| 11A | 2-(4-isopropylphenyl)imidazo[1,2-a]pyridine-3-carbaldehyde<br><br>from 2-(4-isopropylphenyl)imidazo[1,2-a]pyridine | $^1$H-NMR (400 MHz, DMSO-d$_6$, δ/ppm): 1.27 (d, 6H), 2.93-3.05 (m, 1H), 7.33 (t, 1H), 7.44 (d, 2H), 7.74 (t, 1H), 7.85 (d, 2H), 7.91 (d, 1H), 9.58 (d, 1H), 10.03 (s, 1H).<br>LC-MS (Method 1): R$_t$ = 1.03 min; m/z = 265 (M + H)$^+$. |
| 12A | 2-(4-methylphenyl)imidazo[1,2-a]pyridine-3-carbaldehyde<br><br>from 2-(4-methylphenyl)imidazo[1,2-a]pyridine | $^1$H-NMR (400 MHz, DMSO-d$_6$, δ/ppm): 2.41 (s, 3H), 7.34-7.43 (m, 3H), 7.77-7.86 (m, 3H), 7.94 (d, 1H), 9.60 (d, 1H), 10.02 (s, 1H).<br>LC-MS (Method 1): R$_t$ = 0.89 min; m/z = 237 (M + H)$^+$. |
| 13A | 4-(3-formylimidazo[1,2-a]pyridin-2-yl)benzonitrile<br><br>from 4-(imidazo[1,2-a]pyridin-2-yl)benzonitrile | $^1$H-NMR (400 MHz, DMSO-d$_6$, δ/ppm): 7.38 (t, 1H), 7.79 (t, 1H), 7.96 (d, 1H), 8.03 (d, 2H), 8.14 (d, 2H), 9.59 (d, 1H), 10.05 (s, 1H).<br>LC-MS (Method 1): R$_t$ = 0.77 min; m/z = 248 (M + H)$^+$. |

-continued

| Example | Name/Structure/Starting material | Analytical data |
|---|---|---|
| 14A | 2-(4-tert-butylphenyl)imidazo[1,2-a]pyridine-3-carbaldehyde<br><br>[structure: imidazo[1,2-a]pyridine with 2-(4-tert-butylphenyl) and 3-CHO]<br><br>from 2-(4-tert-butylphenyl)imidazo[1,2-a]pyridine | $^1$H-NMR (400 MHz, DMSO-d$_6$, δ/ppm): 1.35 (s, 9H), 7.35 (t, 1H), 7.59 (d, 2H), 7.73-7.80 (m, 1H), 7.87 (d, 2H), 7.89-7.97 (m, 1H), 9.59 (d, 1H), 10.04 (s, 1H).<br>LC-MS (Method 2): R$_t$ = 2.13 min; m/z = 279 (M + H)$^+$. |

Example 15A 2-(4-Chlorophenyl)-3-(hexahydropyrrolo[3,4-c]pyrrol-2(1H)-ylmethyl)imidazo[1,2-a]pyridine dihydrochloride

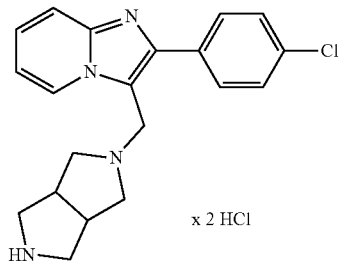 [SMILES: Clc1ccc(-c2nc3ccccn3c2CN2CC3CNCC3C2)cc1]

x 2 HCl 3.1 g (6.84 mmol) of tert-butyl 5-{[2-(4-chlorophenyl)imidazo[1,2-a]pyridin-3-yl]methyl}hexahydropyrrolo[3,4-c]pyrrole-2(1H)-carboxylate were dissolved in 100 ml of dioxane, and 17.11 ml of a 4M solution of hydrogen chloride in dioxane were added with stirring. The mixture was stirred at room temperature for 5 hours. The solids obtained were then filtered off with suction, washed repeatedly with diethyl ether and dried under high vacuum. 3.17 g of the target product was obtained, which was used in subsequent reactions without further purification.

LC-MS (Method 1): R$_t$=0.35 min; m/z=353/355 (M+H)$^+$.

Analogously to Example 15A, the following compounds were prepared from the starting material specified in each case:

| Example | Name/Structure/Starting material | Analytical data |
|---|---|---|
| 16A | 2-(4-Bromophenyl)-3-(hexahydropyrrolo[3,4-c]pyrrol-2(1H)-ylmethyl)imidazo[1,2-a]pyridine dihydrochloride<br><br>[structure: imidazo[1,2-a]pyridine with 2-(4-bromophenyl) and 3-(hexahydropyrrolo[3,4-c]pyrrol-2-ylmethyl)] x2 HCl<br><br>from tert-butyl 5-{[2-(4-bromophenyl)imidazo[1,2-a]pyridin-3-yl]methyl}hexahydropyrrolo[3,4-c]pyrrole-2(1H)-carboxylate | LC-MS (Method 1): R$_t$ = 0.41 min; m/z = 397/399 (M + H)$^+$. |

| Example | Name/Structure/Starting material | Analytical data |
|---|---|---|
| 17A | 3-(Hexahydropyrrolo[3,4-c]pyrrol-2(1H)-ylmethyl)-2-(4-isopropylphenyl)imidazo[1,2-a]pyridine dihydrochloride 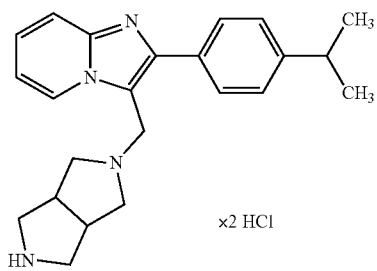 x2 HCl from tert-butyl 5-{[2-(4-isopropylphenyl)imidazo[1,2-a]pyridin-3-yl]methyl}hexahydropyrrolo[3,4-c]pyrrole-2(1H)-carboxylate | LC-MS (Method 4): $R_t$ = 1.43 min; m/z = 361 (M + H)$^+$. |

Example 18A 2-(4-Bromophenyl)-3-(hexahydropyrrolo[3,4-c]pyrrol-2(1H)-ylmethyl)imidazo[1,2-a]pyridine

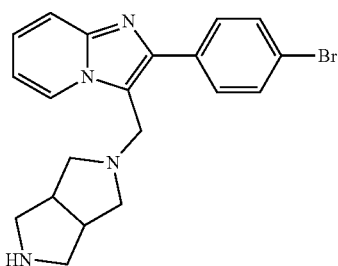 [SMILES: Brc1ccc(-c2nc3ccccn3c2CN2CC3CNCC3C2)cc1]

16.1 g (34.24 mmol) of 2-(4-bromophenyl)-3-(hexahydropyrrolo[3,4-c]pyrrol-2(1H)-ylmethyl)imidazo[1,2-a]pyridine dihydrochloride were dissolved in 200 ml of THF, 24 ml (171 mmol) of triethylamine were added and the mixture was stirred at room temperature for 2 hours. Water and ethyl acetate were then added to the reaction solution and the organic phase was separated. The aqueous phase was extracted twice with ethyl acetate. The combined organic phases were dried over magnesium sulfate, filtered and concentrated to dryness under reduced pressure on a rotary evaporator. This gave 9.72 g (24.46 mmol, 71% of theory) of the target product, which was used in the subsequent reactions without further purification.

LC-MS (Method 1): $R_t$=0.46 min; m/z=397/399 (M+H)$^+$.

WORKING EXAMPLES

Example 1 tert-butyl 5-{[2-(4-chlorophenyl)imidazo [1,2-a]pyridin-3-yl]methyl}hexahydropyrrolo[3,4-c]pyrrole-2(1H)-carboxylate

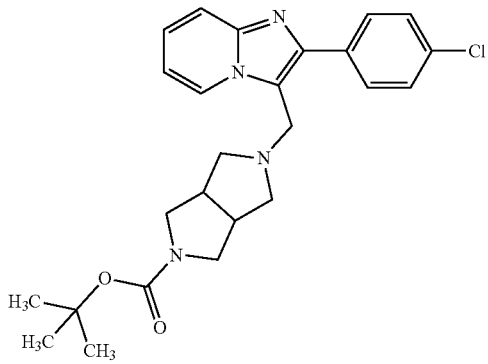 [SMILES: CC(C)(C)OC(=O)N1CC2CN(Cc3c(-c4ccc(Cl)cc4)nc4ccccn34)CC2C1]

Under argon and at room temperature, 1.81 g (7.07 mmol) of 2-(4-chlorophenyl)imidazo[1,2-a]pyridine-3-carbaldehyde were dissolved in 30 ml of THF, and 3 g (14.13 mmol) of tert-butyl hexahydropyrrolo[3,4-c]pyrrole-2(1H)-carboxylate and 0.81 ml (14.13 mmol) of acetic acid were added. 4.49 g (21.20 mmol) of sodium triacetoxyborohydride were then added in portions. The reaction solution was then further stirred at room temperature overnight. After the reaction had ended, water was slowly and carefully added dropwise (evolution of gas), and ethyl acetate was then added. The organic phase was separated off and the aqueous phase was extracted twice with ethyl acetate. The combined organic phases were dried over magnesium sulfate, filtered and concentrated to dryness under reduced pressure on a rotary evaporator. The resulting residue was applied to silica gel and purified by column chromatography on silica gel (Biotage; mobile phase: cyclohexane/ethyl acetate 1:1). This gave 3.2 g (6.58 mmol, 93% of theory) of the title compound. 100 mg thereof were further purified by preparative HPLC (method 7) (Yield: 81 mg).

$^1$H-NMR (400 MHz, DMSO-d$_6$, δ/ppm): 1.35 (s, 9H), 2.43 (d, 2H), 2.47-2.59 (m, 2H, partially obscured by DMSO signal), 2.71 (br. s, 2H), 3.02 (d, 2H), 3.42 (dd, 2H), 4.06 (s, 2H), 6.94 (t, 1H), 7.30 (t, 1H), 7.51 (d, 2H), 7.59 (d, 1H), 7.92 (d, 2H), 8.57 (d, 1H).

LC-MS (Method 1): R$_t$=0.76 min; m/z=453/455 (M+H)$^+$.

Analogously to Example 1, the following compounds were prepared from the starting materials specified in each case:

| Example | Name/Structure/Starting materials | Analytical data |
|---|---|---|
| 2 | tert-butyl 5-{[2-(4-bromophenyl)imidazo[1,2-a]pyridin-3-yl]methyl}hexahydropyrrolo[3,4-c]pyrrole-2(1H)-carboxylate<br>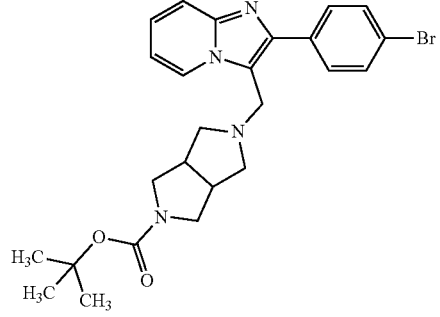<br>from 2-(4-bromophenyl)imidazo[1,2-a]pyridine-3-carbaldehyde and tert-butyl hexahydropyrrolo[3,4-c]pyrrole-2(1H)-carboxylate | $^1$H-NMR (400 MHz, DMSO-d$_6$, δ/ppm): 1.35 (s, 9H), 2.43 (d, 2H), 2.47-2.59 (m, 2H, obscured by DMSO signal), 2.71 (br. s, 2H), 3.02 (d, 2H), 3.42 (dd, 2H), 4.06 (s, 2H), 6.94 (t, 1H), 7.30 (t, 1H), 7.59 (d, 1H), 7.65 (d, 2H), 7.86 (d, 2H), 8.57 (d, 1H).<br>LC-MS (Method 1): R$_t$ = 0.80 min; m/z = 497/499 (M + H)$^+$. |
| 3 | tert-butyl 5-{[2-(4-isopropylphenyl)imidazo[1,2-a]pyridin-3-yl]methyl}hexahydropyrrolo[3,4-c]pyrrole-2(1H)-carboxylate<br>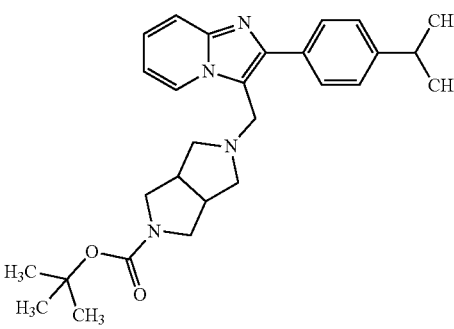<br>from 2-(4-isopropylphenyl)imidazo[1,2-a]pyridine-3-carbaldehyde and tert-butyl hexahydropyrrolo[3,4-c]pyrrole-2(1H)-carboxylate | $^1$H-NMR (400 MHz, DMSO-d$_6$, δ/ppm): 1.24 (d, 6H), 1.36 (s, 9H), 2.43 (d, 2H), 2.47-2.60 (m, 2H, partially obscured by DMSO signal), 2.72 (br. s, 2H), 2.87-2.98 (m, 1H), 3.03 (d, 2H), 3.42 (dd, 2H), 4.06 (s, 2H), 6.91 (t, 1H), 7.27 (t, 1H), 7.35 (d, 2H), 7.58 (d, 1H), 7.79 (d, 2H), 8.55 (d, 1H).<br>LC-MS (Method 2): R$_t$ = 1.56 min; m/z = 461 (M + H)$^+$. |

Example 4

[5-{[2-(4-Chlorophenyl)imidazo[1,2-a]pyridin-3-yl]methyl}hexahydropyrrolo[3,4-c]pyrrol-2(1H)-yl](6-methoxypyridin-2-yl)methanone

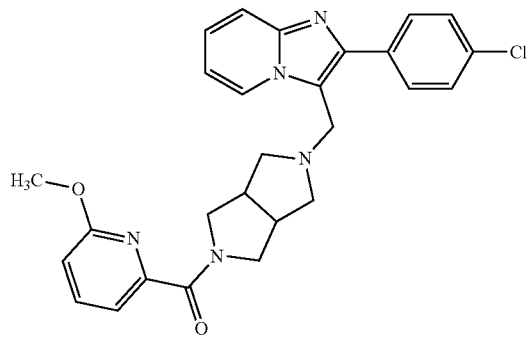 [SMILES: COc1cccc(C(=O)N2CC3CN(Cc4c(-c5ccc(Cl)cc5)nc5ccccn45)CC3C2)n1]

Synthesis Method 1

65 mg (0.42 mmol) of 6-methoxypyridine-2-carboxylic acid were dissolved in 2 ml of DMF, 174 mg (0.46 mmol) of 2-(7-aza-1H-benzotriazol-1-yl)-1,1,3,3-tetramethyluronium hexafluorophosphate (HATU) were added and the mixture was stirred at room temperature for 30 min. 150 mg (0.35 mmol) of 2-(4-chlorophenyl)-3-(hexahydropyrrolo[3,4-c]pyrrol-2(1H)-ylmethyl)imidazo[1,2-a]pyridine dihydrochloride and 0.18 ml (1.06 mmol) of N,N-diisopropylethylamine were then added, and the mixture was stirred further at room temperature overnight. Thereafter, the reaction mixture was separated directly into its components via preparative HPLC (Method 7). 106 mg (0.22 mmol, 62% of theory) of the title compound were obtained.

LC-MS (Method 1): $R_t$=0.70 min; m/z=488/490 (M+H)$^+$.

$^1$H-NMR (400 MHz, DMSO-d$_6$): δ [ppm]=2.41-2.52 (m, 2H, partially obscured by DMSO signal), 2.55-2.64 (m, 2H), 2.79 (br. s, 2H), 3.44-3.60 (m, 2H), 3.66-3.84 (m, 2H), 3.76 (s, 3H), 4.00-4.13 (m, 2H), 6.84-6.92 (m, 2H), 7.24 (d, 1H), 7.28 (t, 1H), 7.49 (d, 2H), 7.58 (d, 1H), 7.78 (t, 1H), 7.89 (d, 2H), 8.57 (d, 1H).

Example 5

[5-{[2-(4-Bromophenyl)imidazo[1,2-a]pyridin-3-yl]methyl}hexahydropyrrolo[3,4-c]pyrrol-2(1H)-yl](cyclopentyl)methanone

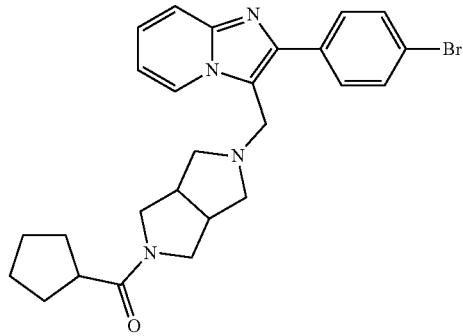 [SMILES: O=C(C1CCCC1)N1CC2CN(Cc3c(-c4ccc(Br)cc4)nc4ccccn34)CC2C1]

Synthesis Method 2

41 mg (0.36 mmol) of cyclopentanecarboxylic acid were dissolved in 1.5 ml of DMF, 172 mg (0.45 mmol) of 2-(7-aza-1H-benzotriazol-1-yl)-1,1,3,3-tetramethyluronium hexafluorophosphate (HATU) were added and the mixture was stirred at room temperature for 30 min. 120 mg (0.30 mmol) of 2-(4-bromophenyl)-3-(hexahydropyrrolo[3,4-c]pyrrol-2(1H)-ylmethyl)imidazo [1,2-a]pyridine and 0.11 ml (0.60 mmol) of N,N-diisopropylethylamine were then added, and the mixture was stirred further at room temperature overnight. Thereafter, the reaction mixture was separated directly into its components via preparative HPLC (Method 7). 87 mg (0.18 mmol, 58% of theory) of the title compound were obtained.

LC-MS (Method 1): $R_t$=0.71 min; m/z=493/495 (M+H)+.

$^1$H-NMR (400 MHz, DMSO-d$_6$): δ [ppm]=2.41-2.52 (m, 2H, partially obscured by DMSO signal), 2.55-2.64 (m, 2H), 2.79 (br. s, 2H), 3.44-3.60 (m, 2H), 3.66-3.84 (m, 2H), 3.76 (s, 3H), 4.00-4.13 (m, 2H), 6.84-6.92 (m, 2H), 7.24 (d, 1H), 7.28 (t, 1H), 7.49 (d, 2H), 7.58 (d, 1H), 7.78 (t, 1H), 7.89 (d, 2H), 8.57 (d, 1H).

The following compounds were also prepared according to Synthesis methods 1 and 2 described above, using the starting materials specified in each case:

| Example | Name / Structure / Starting materials | Analytical data |
|---|---|---|
| 6 | [5-{[2-(4-Bromophenyl)imidazo[1,2-a]pyridin-3-yl]methyl}hexahydropyrrolo[3,4-c]pyrrol-2(1H)-yl](2-fluorophenyl)methanone<br><br>from 2-(4-bromophenyl)-3-(hexahydropyrrolo[3,4-c]pyrrol-2(1H)-ylmethyl)imidazo[1,2-a]pyridine dihydrochloride and 2-fluorobenzoic acid (according to Synthesis method 1) | $^1$H-NMR (400 MHz, DMSO-d$_6$): δ [ppm] = 2.32-2.39 (m, 1H), 2.45 (t, 1H), 2.52-2.62 (m, 2H, partially obscured by DMSO signal), 2.68-2.87 (m, 2H), 2.93-3.01 (m, 1H), 3.35-3.44 (m, 2H), 3.65-3.74 (m, 1H), 4.02-4.12 (m, 2H), 6.95 (t, 1H), 7.18-7.34 (m, 4H), 7.42-7.51 (m, 1H), 7.60 (d, 1H), 7.65 (d, 2H), 7.83 (d, 2H), 8.58 (d, 1H). LC-MS (Method 1): $R_t$ = 0.75 min; m/z = 519/521 (M + H)$^+$. |

-continued

| Example | Name / Structure / Starting materials | Analytical data |
|---|---|---|
| 7 | [5-{[2-(4-Bromophenyl)imidazo[1,2-a]pyridin-3-yl]methyl}hexahydropyrrolo[3,4-c]pyrrol-2(1H)-yl](2-chloro-5-fluorophenyl)methanone<br />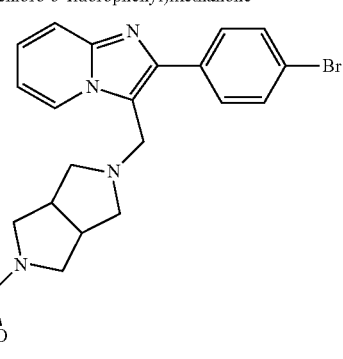<br />from 2-(4-bromophenyl)-3-(hexahydropyrrolo[3,4-c]pyrrol-2(1H)-ylmethyl)imidazo[1,2-a]pyridine dihydrochloride and 2-chloro-5-fluorobenzoic acid (according to Synthesis method 1) | $^1$H-NMR (400 MHz, DMSO-d$_6$): δ [ppm] = 2.31-2.39 (m, 1H), 2.45 (t, 1H), 2.59 (d, 2H), 2.69-2.78 (m, 1H), 2.78-2.90 (m, 2H), 3.27-3.42 (m, 2H, partially obscured by H$_2$O signal), 3.65-3.74 (m, 1H), 4.08 (q, 2H), 6.94 (t, 1H), 7.11-7.23 (m, 1H), 7.24-7.34 (m, 2H), 7.50-7.56 (m, 1H), 7.60 (d, 1H), 7.65 (d, 2H), 7.84 (d, 2H), 8.58 (d, 1H).<br />LC-MS (Method 1):<br />R$_t$ = 0.80 min; m/z = 553/555/556/558 (M + H)$^+$. |
| 8 | [5-{[2-(4-Bromophenyl)imidazo[1,2-a]pyridin-3-yl]methyl}hexahydropyrrolo[3,4-c]pyrrol-2(1H)-yl](cyclohexyl)methanone<br />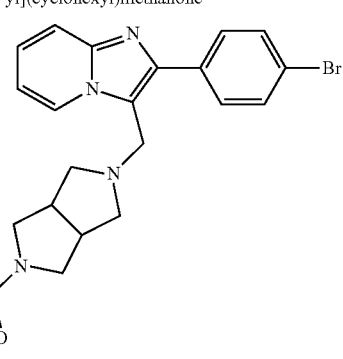<br />from 2-(4-bromophenyl)-3-(hexahydropyrrolo[3,4-c]pyrrol-2(1H)-ylmethyl)imidazo[1,2-a]pyridine dihydrochloride and cyclohexanecarboxylic acid (according to Synthesis method 1) | $^1$H-NMR (400 MHz, DMSO-d$_6$): δ [ppm] = 1.04-1.34 (m, 5H), 1.48-1.73 (m, 5H), 2.24-2.35 (m, 1H), 2.42-2.58 (m, 4H, partially obscured by DMSO signal), 2.63-2.75 (m, 1H), 2.75-2.86 (m, 1H), 3.13-3.21 (m, 1H), 3.21-3.27 (m, 1H), 3.40-3.49 (m, 1H), 3.58-3.67 (m, 1H), 4.06 (s, 2H), 6.91 (t, 1H), 7.29 (t, 1H), 7.59 (d, 1H), 7.64 (d, 2H), 7.84 (d, 2H), 8.55 (d, 1H).<br />LC-MS (Method 1):<br />R$_t$ = 0.78 min; m/z = 507/509 (M + H)$^+$. |
| 9 | [5-{[2-(4-Bromophenyl)imidazo[1,2-a]pyridin-3-yl]methyl}hexahydropyrrolo[3,4-c]pyrrol-2(1H)-yl](cyclobutyl)methanone<br />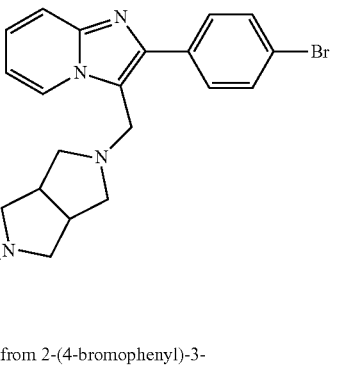<br />from 2-(4-bromophenyl)-3-(hexahydropyrrolo[3,4-c]pyrrol-2(1H)-ylmethyl)imidazo[1,2-a]pyridine dihydrochloride and cyclobutanecarboxylic acid (according to Synthesis method 1) | $^1$H-NMR (400 MHz, DMSO-d$_6$): δ [ppm] = 1.61-1.74 (m, 1H), 1.76-1.90 (m, 1H), 1.92-2.15 (m, 4H), 2.36-2.43 (m, 1H), 2.44-2.60 (m, 3H, partially obscured by DMSO signal), 2.63-2.82 (m, 2H), 3.04-3.17 (m, 2H), 3.23 (dd, 1H), 3.38-3.48 (m, 2H), 4.04 (q, 2H), 6.91 (t, 1H), 7.29 (t, 1H), 7.59 (d, 1H), 7.64 (d, 2H), 7.83 (d, 2H), 8.54 (d, 1H).<br />LC-MS (Method 1):<br />R$_t$ = 0.70 min; m/z = 479/481 (M + H)$^+$. |

| Example | Name / Structure / Starting materials | Analytical data |
|---|---|---|
| 10 | [5-{[2-(4-Bromophenyl)imidazo[1,2-a]pyridin-3-yl]methyl}hexahydropyrrolo[3,4-c]pyrrol-2(1H)-yl](3-methoxyphenyl)methanone<br>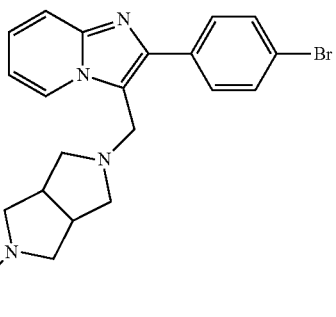<br>from 2-(4-bromophenyl)-3-(hexahydropyrrolo[3,4-c]pyrrol-2(1H)-ylmethyl)imidazo[1,2-a]pyridine dihydrochloride and 3-methoxybenzoic acid<br>(according to Synthesis method 1) | $^1$H-NMR (400 MHz, DMSO-d$_6$): δ [ppm] = 2.30-2.40 (m, 1H), 2.40-2.64 (m, 3H, partially obscured by DMSO signal), 2.69-2.83 (m, 2H), 3.07-3.17 (m, 1H), 3.40-3.60 (m, 2H), 3.63-3.74 (m, 1H), 3.71 (s, 3H), 3.99-4.12 (m, 2H), 6.83-7.00 (m, 4H), 7.24-7.34 (m, 2H), 7.59 (d, 1H), 7.65 (d, 2H), 7.85 (d, 2H), 8.58 (d, 1H).<br>LC-MS (Method 1):<br>R$_t$ = 0.75 min; m/z = 531/533 (M + H)$^+$. |
| 11 | [5-{[2-(4-Bromophenyl)imidazo[1,2-a]pyridin-3-yl]methyl}hexahydropyrrolo[3,4-c]pyrrol-2(1H)-yl](2-methoxyphenyl)methanone<br>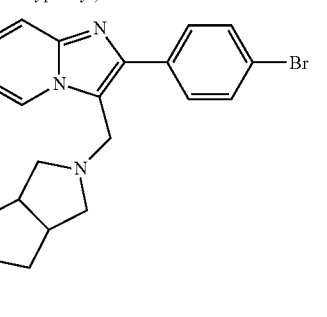<br>from 2-(4-bromophenyl)-3-(hexahydropyrrolo[3,4-c]pyrrol-2(1H)-ylmethyl)imidazo[1,2-a]pyridine and 2-methoxybenzoic acid<br>(according to Synthesis method 2) | $^1$H-NMR (400 MHz, DMSO-d$_6$): δ [ppm] = 2.25-2.34 (m, 1H), 2.45 (t, 1H), 2.48-2.57 (m, 1H, obscured by DMSO signal), 2.60 (t, 1H), 2.64-2.73 (m, 1H), 2.73-2.83 (m, 1H), 2.83-2.92 (m, 1H), 3.23-3.39 (m, 2H, partially obscured by H$_2$O signal), 3.59-3.75 (m, 1H), 3.69 (s, 3H), 4.07(s, 2H), 6.88-6.99 (m, 2H), 7.00-7.08 (m, 2H), 7.27-7.38 (m, 2H), 7.60 (d, 1H), 7.65 (d, 2H), 7.84 (d, 2H), 8.58 (d, 1H).<br>LC-MS (Method 1):<br>R$_t$ = 0.70 min; m/z = 531/533 (M + H)$^+$. |
| 12 | [5-{[2-(4-Bromophenyl)imidazo[1,2-a]pyridin-3-yl]methyl}hexahydropyrrolo[3,4-c]pyrrol-2(1H)-yl](5-fluoro-2-methoxyphenyl)methanone<br>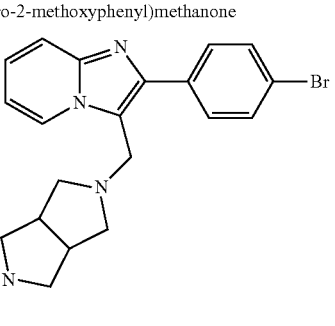<br>from 2-(4-bromophenyl)-3-(hexahydropyrrolo[3,4-c]pyrrol-2(1H)-ylmethyl)imidazo[1,2-a]pyridine and 5-fluoro-2-methoxybenzoic acid<br>(according to Synthesis method 2) | $^1$H-NMR (400 MHz, DMSO-d$_6$): δ [ppm] = 2.28-2.36 (m, 1H), 2.46 (t, 1H), 2.48-2.56 (m, 1H, obscured by DMSO signal), 2.59 (t, 1H), 2.65-2.74 (m, 1H), 2.74-2.84 (m, 1H), 2.85-2.94 (m, 1H), 3.26-3.39 (m, 2H, partially obscured by H$_2$O signal), 3.60-3.73 (m, 1H), 3.68 (s, 3H), 4.01-4.13 (m, 2H), 6.87-6.99 (m, 2H), 7.01-7.08 (m, 1H), 7.14-7.22 (m, 1H), 7.31 (t, 1H), 7.60 (d, 1H), 7.65 (d, 2H), 7.84 (d, 2H), 8.58 (d, 1H).<br>LC-MS (Method 1):<br>R$_t$ = 0.73 min; m/z = 549/551 (M + H)$^+$. |

| Example | Name / Structure / Starting materials | Analytical data |
|---|---|---|
| 13 | [5-{[2-(4-Bromophenyl)imidazo[1,2-a]pyridin-3-yl]methyl}hexahydropyrrolo[3,4-c]pyrrol-2(1H)-yl](2-methylphenyl)methanone<br>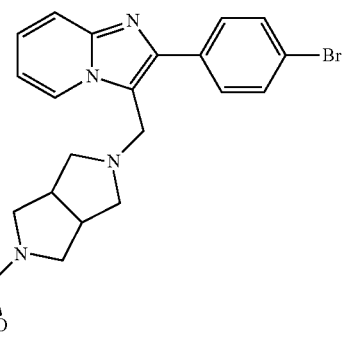<br>from 2-(4-bromophenyl)-3-(hexahydropyrrolo[3,4-c]pyrrol-2(1H)-ylmethyl)imidazo[1,2-a]pyridine and 2-methylbenzoic acid (according to Synthesis method 2) | $^1$H-NMR (400 MHz, DMSO-$d_6$): δ [ppm] = 2.07 (s, 3H), 2.24-2.31 (m, 1H), 2.44 (t, 1H), 2.48-2.57 (m, 1H, obscured by DMSO signal), 2.60 (t, 1H), 2.65-2.74 (m, 1H), 2.74-2.86 (m, 2H), 3.22-3.29 (m, 1H), 3.42 (dd, 1H), 3.60-3.69 (m, 1H), 4.01-4.13 (m, 2H), 6.95 (t, 1H), 7.02 (d, 1H), 7.11-7.35 (m, 4H), 7.60 (d, 1H), 7.65 (d, 2H), 7.83 (d, 2H), 8.56 (d, 1H).<br>LC-MS (Method 1):<br>$R_t$ = 0.73 min; m/z = 515/517 (M + H)$^+$. |
| 14 | [5-{[2-(4-Chlorophenyl)imidazo[1,2-a]pyridin-3-yl]methyl}hexahydropyrrolo[3,4-c]pyrrol-2(1H)-yl](2-fluorophenyl)methanone<br>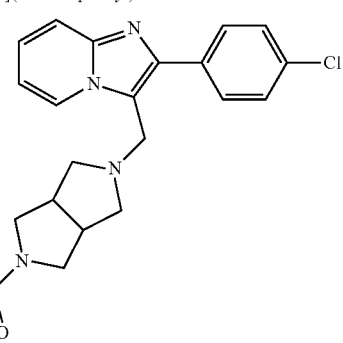<br>from 2-(4-chlorophenyl)-3-(hexahydropyrrolo[3,4-c]pyrrol-2(1H)-ylmethyl)imidazo[1,2-a]pyridine dihydrochloride and 2-fluorobenzoic acid (according to Synthesis method 1) | $^1$H-NMR (400 MHz, DMSO-$d_6$): δ [ppm] = 2.35 (dd, 1H), 2.45 (t, 1H), 2.53-2.62 (m, 2H, partially obscured by DMSO signal), 2.68-2.86 (m, 2H), 2.97 (dd, 1H), 3.35-3.45 (m, 2H), 3.64-3.74 (m, 1H), 4.02-4.13 (m, 2H), 6.95 (t, 1H), 7.18-7.34 (m, 4H), 7.42-7.49 (m, 1H), 7.52 (d, 2H), 7.60 (d, 1H), 7.89 (d, 2H), 8.56 (d, 1H).<br>LC-MS (Method 1):<br>$R_t$ = 0.70 min; m/z = 475/477 (M + H)$^+$. |

| Example | Name / Structure / Starting materials | Analytical data |
|---|---|---|
| 15 | (2-Chloro-5-fluorophenyl)[5-{[2-(4-chlorophenyl)imidazo[1,2-a]pyridin-3-yl]methyl}hexahydropyrrolo[3,4-c]pyrrol-2(1H)-yl]methanone<br />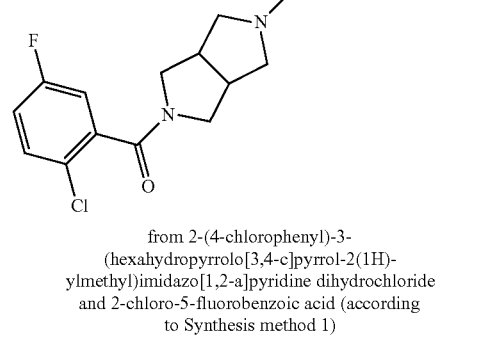<br />from 2-(4-chlorophenyl)-3-(hexahydropyrrolo[3,4-c]pyrrol-2(1H)-ylmethyl)imidazo[1,2-a]pyridine dihydrochloride and 2-chloro-5-fluorobenzoic acid (according to Synthesis method 1) | $^1$H-NMR (400 MHz, DMSO-$d_6$): δ [ppm] = 2.35 (dd, 1H), 2.45 (t, 1H), 2.59 (d, 2H), 2.68-2.78 (m, 1H), 2.78-2.81 (m, 2H), 3.26-3.42 (m, 2H, partially obscured by H$_2$O signal), 3.70 (dd, 1H), 4.08 (q, 2H), 6.94 (td, 1H), 7.11-7.21 (m, 1H), 7.24-7.33 (m, 2H), 7.47-7.56 (m, 3H), 7.60 (d, 1H), 7.90 (d, 2H), 8.58 (d, 1H).<br />LC-MS (Method 5):<br />R$_t$ - 1.00 min; m/z - 509/510/511/512 (M + H)$^+$. |
| 16 | [5-{[2-(4-Chlorophenyl)imidazo[1,2-a]pyridin-3-yl]methyl}hexahydropyrrolo[3,4-c]pyrrol-2(1H)-yl](cyclohexyl)methanone<br />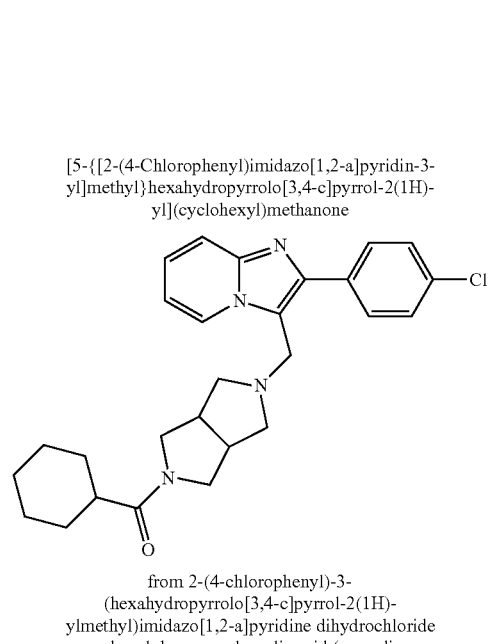<br />from 2-(4-chlorophenyl)-3-(hexahydropyrrolo[3,4-c]pyrrol-2(1H)-ylmethyl)imidazo[1,2-a]pyridine dihydrochloride and cyclohexanecarboxylic acid (according to Synthesis method 1) | $^1$H-NMR (400 MHz, DMSO-$d_6$): δ [ppm] = 1.06-1.34 (m, 5H), 1.47-1.71 (m, 5H), 2.24-2.35 (m, 1H), 2.43-2.58 (m, 4H, partially obscured by DMSO signal), 2.64-2.75 (m, 1H), 2.75-2.86 (m, 1H), 3.17 (dd, 1H), 3.24 (dd, 1H), 3.45 (dd, 1H), 3.63 (dd, 1H), 4.06 (s, 2H), 6.91 (td, 1H), 7.29 (t, 1H), 7.51 (d, 2H), 7.59 (d, 1H), 7.90 (d, 2H), 8.55 (d, 1H).<br />LC-MS (Method 1):<br />R$_t$ = 0.74 min; m/z = 463/465 (M + H)$^+$. |

| Example | Name / Structure / Starting materials | Analytical data |
|---|---|---|
| 17 | [5-{[2-(4-Chlorophenyl)imidazo[1,2-a]pyridin-3-yl]methyl}hexahydropyrrolo[3,4-c]pyrrol-2(1H)-yl](3-methoxyphenyl)methanone<br><br>from 2-(4-chlorophenyl)-3-(hexahydropyrrolo[3,4-c]pyrrol-2(1H)-ylmethyl)imidazo[1,2-a]pyridine dihydrochloride and 3-methoxybenzoic acid (according to Synthesis method 1) | $^1$H-NMR (400 MHz, DMSO-$d_6$): δ [ppm] = 2.31-2.41 (m, 1H), 2.41-2.53 (m, 1H, partially obscured by DMSO signal), 2.53-2.64 (m, 2H, partially obscured by DMSO signal), 2.69-2.84 (m, 2H), 3.05-3.17 (m, 1H), 3.41-3.60 (m, 2H), 3.63-3.74 (m, 1H), 3.71 (s, 3H), 3.97-4.12 (m, 2H), 6.84-7.00 (m, 4H), 7.24-7.34 (m, 2H), 7.52 (d, 2H), 7.59 (d, 1H), 7.91 (d, 2H), 8.58 (d, 1H).<br>LC-MS (Method 1):<br>$R_t$ = 0.71 min; m/z = 487/489 (M + H)$^+$. |
| 18 | [5-{[2-(4-Chlorophenyl)imidazo[1,2-a]pyridin-3-yl]methyl}hexahydropyrrolo[3,4-c]pyrrol-2(1H)-yl](2-methoxyphenyl)methanone<br><br>from 2-(4-chlorophenyl)-3-(hexahydropyrrolo[3,4-c]pyrrol-2(1H)-ylmethyl)imidazo[1,2-a]pyridine dihydrochloride and 2-methoxybenzoic acid (according to Synthesis method 1) | $^1$H-NMR (400 MHz, DMSO-$d_6$): δ [ppm] = 2.26-2.35 (m, 1H), 2.46 (t, 1H), 2.48-2.56 (m, 1H, partially obscured by DMSO signal), 2.60 (t, 1H), 2.64-2.73 (m, 1H), 2.73-2.83 (m, 1H), 2.83-2.92 (m, 1H), 3.24-3.38 (m, 2H, partially obscured by H$_2$O signal), 3.60-3.74 (m, 1H), 3.69 (s, 3H), 4.08 (s, 2H), 6.88-6.99 (m, 2H), 7.00-7.09 (m, 2H), 7.27-7.38 (m, 2H), 7.52 (d, 2H), 7.60 (d, 1H), 7.90 (d, 2H), 8.59 (d, 1H).<br>LC-MS (Method 1):<br>$R_t$ = 0.72 min; m/z = 487/489 (M + H)$^+$. |
| 19 | [5-{[2-(4-Chlorophenyl)imidazo[1,2-a]pyridin-3-yl]methyl}hexahydropyrrolo[3,4-c]pyrrol-2(1H)-yl](5-fluoro-2-methoxyphenyl)methanone<br><br>from 2-(4-chlorophenyl)-3-(hexahydropyrrolo[3,4-c]pyrrol-2(1H)-ylmethyl)imidazo[1,2-a]pyridine dihydrochloride and 2-methoxy-5-fluorobenzoic acid (according to Synthesis method 1) | $^1$H-NMR (400 MHz, DMSO-$d_6$): δ [ppm] = 2.28-2.37 (m, 1H), 2.46 (t, 1H), 2.48-2.57 (m, 1H, obscured by DMSO signal), 2.59 (t, 1H), 2.64-2.74 (m, 1H), 2.74-2.85 (m, 1H), 2.85-2.94 (m, 1H), 3.27-3.40 (m, 2H, partially obscured by H$_2$O signal), 3.59-3.73 (m, 1H), 3.68 (s, 3H), 4.02-4.12 (m, 2H), 6.87-6.99 (m, 2H), 7.01-7.08 (m, 1H), 7.14-7.22 (m, 1H), 7.27-7.34 (m, 1H), 7.52 (d, 2H), 7.60 (d, 1H), 7.90 (d, 2H), 8.59 (d, 1H).<br>LC-MS (Method 1):<br>$R_t$ = 0.75 min; m/z = 505/507 (M + H)$^+$. |

| Example | Name / Structure / Starting materials | Analytical data |
|---|---|---|
| 20 | [5-{[2-(4-Chlorophenyl)imidazo[1,2-a]pyridin-3-yl]methyl}hexahydropyrrolo[3,4-c]pyrrol-2(1H)-yl](2-methylphenyl)methanone<br>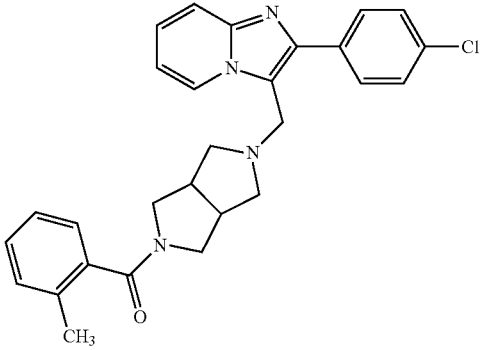<br>from 2-(4-chlorophenyl)-3-(hexahydropyrrolo[3,4-c]pyrrol-2(1H)-ylmethyl)imidazo[1,2-a]pyridine dihydrochloride and 2-methylbenzoic acid (according to Synthesis method 1) | $^1$H-NMR (400 MHz, DMSO-$d_6$): δ [ppm] = 2.07 (s, 3H), 2.28 (dd, 1H), 2.45 (t, 1H), 2.48-2.57 (m, 1H, partially obscured by DMSO signal), 2.60 (t, 1H), 2.64-2.74 (m, 1H), 2.75-2.86 (m, 2H), 3.26 (dd, 1H), 3.42 (dd, 1H), 3.64 (dd, 1H), 4.02-4.14 (m, 2H), 6.95 (t, 1H), 7.02 (d, 1H), 7.10-7.35 (m, 4H), 7.52 (d, 2H), 7.60 (d, 1H), 7.89 (d, 2H), 8.56 (d, 1H).<br>LC-MS (Method 1):<br>$R_t$ = 0.77 min; m/z = 471/473 (M + H)$^+$. |
| 21 | [5-{[2-(4-Chlorophenyl)imidazo[1,2-a]pyridin-3-yl]methyl}hexahydropyrrolo[3,4-c]pyrrol-2(1H)-yl](5-fluoro-2-methylphenyl)methanone<br>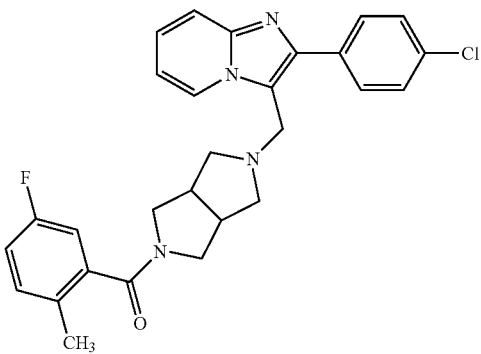<br>from 2-(4-chlorophenyl)-3-(hexahydropyrrolo[3,4-c]pyrrol-2(1H)-ylmethyl)imidazo[1,2-a]pyridine dihydrochloride and 5-fluoro-2-methylbenzoic acid (according to Synthesis method 1) | $^1$H-NMR (400 MHz, DMSO-$d_6$): δ [ppm] = 2.03 (S, 3H), 2.31 (dd, 1H), 2.45 (t, 1H), 2.55-2.63 (m, 2H), 2.65-2.76 (m, 1H), 2.81 (dd, 2H), 3.24-3.34 (m, 1H, partially obscured by H$_2$O signal), 3.41 (dd, 1H), 3.66 (dd, 1H), 4.08 (q, 2H), 6.88-6.98 (m, 2H), 7.09 (td, 1H), 7.23 (dd, 1H), 7.30 (t, 1H), 7.51 (d, 2H), 7.60 (d, 1H), 7.90 (d, 2H), 8.57 (d, 1H).<br>LC-MS (Method 1):<br>$R_t$ = 0.79 min; m/z = 489/491 (M + H)$^+$. |

| Example | Name / Structure / Starting materials | Analytical data |
|---|---|---|
| 22 | [5-{[2-(4-Chlorophenyl)imidazo[1,2-a]pyridin-3-yl]methyl}hexahydropyrrolo[3,4-c]pyrrol-2(1H)-yl][3-(trifluoromethoxy)phenyl]methanone<br>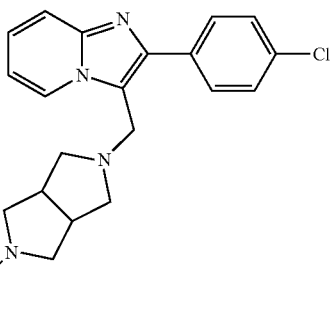<br>from 2-(4-chlorophenyl)-3-(hexahydropyrrolo[3,4-c]pyrrol-2(1H)-ylmethyl)imidazo[1,2-a]pyridine dihydrochloride and 3-(trifluoromethoxy)benzoic acid (according to Synthesis method 1) | $^1$H-NMR (400 MHz, DMSO-$d_6$): δ [ppm] = 2.31-2.65 (m, 4H, partially obscured by DMSO signal), 2.70-2.85 (m, 2H), 3.03-3.16 (m, 1H), 3.41-3.50 (m, 1H), 3.50-3.61 (m, 1H), 3.65-3.76 (m, 1H), 4.06 (q, 2H), 6.94 (td, 1H), 7.25-7.33 (m, 2H), 7.36-7.45 (m, 2H), 7.47-7.56 (m, 3H), 7.59 (d, 1H), 7.90 (d, 2H), 8.58 (d, 1H).<br>LC-MS (Method 1):<br>$R_t$ = 0.81 min; m/z = 541/543 (M + H)$^+$. |
| 23 | [5-{[2-(4-Chlorophenyl)imidazo[1,2-a]pyridin-3-yl]methyl}hexahydropyrrolo[3,4-c]pyrrol-2(1H)-yl][3-(trifluoromethyl)phenyl]methanone<br>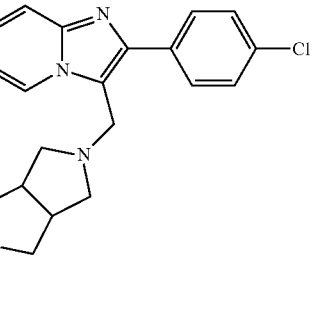<br>from 2-(4-chlorophenyl)-3-(hexahydropyrrolo[3,4-c]pyrrol-2(1H)-ylmethyl)imidazo[1,2-a]pyridine dihydrochloride and 3-(trifluoromethyl)benzoic acid (according to Synthesis method 1) | $^1$H-NMR (400 MHz, DMSO-$d_6$): δ [ppm] = 2.35-2.68 (m, 4H, partially obscured by DMSO signal), 2.70-2.86 (m, 2H), 3.03-3.16 (m, 1H), 3.45-3.54 (m, 1H), 3.54-3.63 (m, 1H), 3.67-3.78 (m, 1H), 4.06 (q, 2H), 6.94 (t, 1H), 7.30 (d, 1H), 7.36-7.45 (m, 2H), 7.51 (d, 2H), 7.56-7.70 (m, 4H), 7.79 (d, 1H), 7.90 (d, 2H), 8.58 (d, 1H).<br>LC-MS (Method 1):<br>$R_t$ = 0.79 min; m/z = 525/527 (M + H)$^+$. |
| 24 | [5-{[2-(4-Bromophenyl)imidazo[1,2-a]pyridin-3-yl]methyl}hexahydropyrrolo[3,4-c]pyrrol-2(1H)-yl](6-methoxypyridin-2-yl)methanone<br>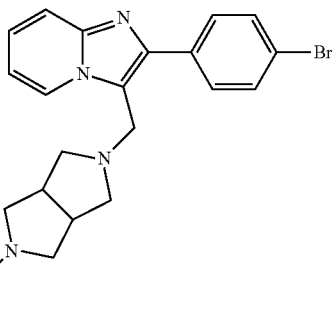<br>from 2-(4-bromophenyl)-3-(hexahydropyrrolo[3,4-c]pyrrol-2(1H)-ylmethyl)imidazo[1,2-a]pyridine and 6-methoxypyridine-2-carboxylic acid (according to Synthesis method 2) | $^1$H-NMR (400 MHz, DMSO-$d_6$): δ [ppm] = 2.42-2.64 (m, 4H, partially obscured by DMSO signal), 2.73-2.84 (m, 2H), 3.44-3.60 (m, 2H), 3.65-3.74 (m, 1H), 3.74-3.83 (m, 1H), 3.76 (s, 3H), 4.00-4.12 (m, 2H), 6.84-6.92 (m, 2H), 7.21-7.31 (m, 2H), 7.55-7.66 (m, 3H), 7.78 (t, 1H), 7.83 (d, 2H), 8.57 (d, 1H).<br>LC-MS (Method 2):<br>$R_t$ = 1.31 min; m/z = 532/534 (M + H)$^+$. |

| Example | Name / Structure / Starting materials | Analytical data |
|---|---|---|
| 25 | [5-{[2-(4-Isopropylphenyl)imidazo[1,2-a]pyridin-3-yl]methyl}hexahydropyrrolo[3,4-c]pyrrol-2(1H)-yl](6-methoxypyridin-2-yl)methanone<br><br>from 3-(hexahydropyrrolo[3,4-c]pyrrol-2(1H)-ylmethyl)-2-(4-isopropylphenyl)imidazo[1,2-a]pyridine dihydrochloride and 6-methoxypyridine acid (according to Synthesis method 1) | $^1$H-NMR (400 MHz, DMSO-$d_6$): δ [ppm] = 1.24 (d, 6H), 2.42-2.65 (m, 4H, partially obscured by DMSO signal), 2.74-2.85 (m, 2H), 2.87-2.98 (m, 1H), 3.48 (dd, 1H), 3.57 (dd, 1H), 3.67-3.75 (m, 1H), 3.75-3.85 (m, 1H), 3.77 (s, 3H), 4.02-4.13 (m, 2H), 6.85 (td, 1H), 6.89 (d, 1H), 7.20-7.34 (m, 4H), 7.56 (d, 1H), 7.73-7.81 (m, 3H), 8.55 (d, 1H).<br>LC-MS (Method 2):<br>R$_t$ = 1.38 min; m/z = 496 (M + H)$^+$. |
| 26 | (2-Fluorophenyl)[5-{[2-(4-isopropylphenyl)imidazo[1,2-a]pyridin-3-yl]methyl}hexahydropyrrolo[3,4-c]pyrrol-2(1H)-yl]methanone<br><br>from 3-(hexahydropyrrolo[3,4-c]pyrrol-2(1H)-ylmethyl)-2-(4-isopropylphenyl)imidazo[1,2-a]pyridine dihydrochloride and 2-fluorocarboxylic acid (according to Synthesis method 1) | $^1$H-NMR (400 MHz, DMSO-$d_6$): δ [ppm] = 1.25 (d, 6H), 2.34-2.41 (m, 1H), 2.42-2.63 (m, 3H, partially obscured by DMSO signal), 2.69-2.87 (m, 2H), 2.88-3.03 (m, 2H), 3.36-3.45 (m, 2H), 3.65-3.75 (m, 1H), 4.01-4.14 (m, 2H), 6.93 (t, 1H), 7.17-7.37 (m, 6H), 7.41-7.51 (m, 1H), 7.58 (d, 1H), 7.78 (d, 2H), 8.56 (d, 1H).<br>LC-MS (Method 2):<br>R$_t$ = 1.40 min; m/z = 483 (M + H)$^+$. |

| Example | Name / Structure / Starting materials | Analytical data |
|---|---|---|
| 27 | [5-{[2-(4-Isopropylphenyl)imidazo[1,2-a]pyridin-3-yl]methyl}hexahydropyrrolo[3,4-c]pyrrol-2(1H)-yl](3-methoxyphenyl)methanone<br>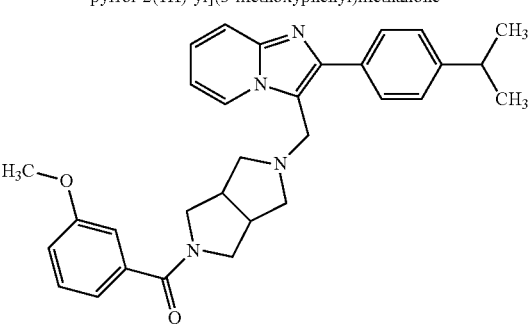<br>from 3-(hexahydropyrrolo[3,4-c]pyrrol-2(1H)-ylmethyl)-2-(4-isopropylphenyl)imidazo[1,2-a]pyridine dihydrochloride and 3-methoxybenzoic acid (according to Synthesis method 1) | $^1$H-NMR (400 MHz, DMSO-d$_6$): δ [ppm] = 1.25 (d, 6H), 2.31-2.42 (m, 1H), 2.42-2.56 (m, 1H, partially obscured by DMSO signal), 2.56-2.64 (m, 2H), 2.69-2.83 (m, 2H), 2.89-2.98 (m, 1H), 3.08-3.18 (m, 1H), 3.41-3.50 (m, 1H), 3.51-3.61 (m, 1H), 3.63-3.75 (m, 1H), 3.71 (s, 3H), 3.98-4.13 (m, 2H), 6.86-7.01 (m, 4H), 7.23-7.36 (m, 4H), 7.58 (d, 1H), 7.78 (d, 2H), 8.56 (d, 1H).<br>LC-MS (Method 2):<br>R$_t$ = 1.40 min; m/z = 495 (M + H)$^+$. |
| 28 | Cyclopentyl[5-{[2-(4-isopropylphenyl)imidazo[1,2-a]pyridin-3-yl]methyl}hexahydropyrrolo[3,4-c]pyrrol-2(1H)-yl]methanone<br>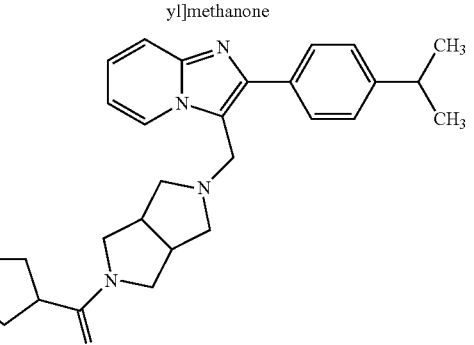<br>from 3-(hexahydropyrrolo[3,4-c]pyrrol-2(1H)-ylmethyl)-2-(4-isopropylphenyl)imidazo[1,2-a]pyridine dihydrochloride and cyclopentanecarboxylic acid (according to Synthesis method 1) | $^1$H-NMR (400 MHz, DMSO-d$_6$): δ [ppm] = 1.24 (d, 6H), 1.40-1.76 (m, 8H), 2.43-2.61 (m, 4H, partially obscured by DMSO signal), 2.65-2.86 (m, 3H), 2.88-2.99 (m, 1H), 3.17-3.30 (m, 2H), 3.46 (dd, 1H), 3.62 (dd, 1H), 4.06 (s, 2H), 6.88 (t, 1H), 7.27 (t, 1H), 7.32 (d, 2H), 7.57 (d, 1H), 7.79 (d, 2H), 8.53 (d, 1H).<br>LC-MS (Method 2):<br>R$_t$ = 1.36 min; m/z = 457 (M + H)$^+$. |

Example 29

5-{[2-(4-Bromophenyl)imidazo[1,2-a]pyridin-3-yl]methyl}-N-methyl-N-phenylhexahydropyrrolo[3,4-c]pyrrole-2(1H)-carboxamide

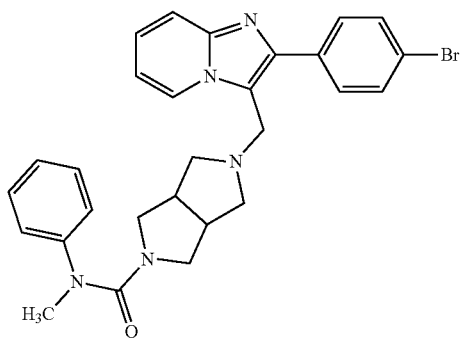 [SMILES: CN(C(=O)N1CC2CN(Cc3c(-c4ccc(Br)cc4)nc4ccccn34)CC2C1)c1ccccc1]

16.9 mg (0.10 mmol) of methyl(phenyl)carbamoyl chloride were initially charged in a well of a 96-well multititer plate and cooled to 0° C. Separately, 39.7 mg (0.10 mmol) of 2-(4-bromophenyl)-3-(hexahydropyrrolo[3,4-c]pyrrol-2(1H)-ylmethyl) imidazo[1,2-a]pyridin-2-yl]pyridine were dissolved in 0.8 ml of 1,2-dichloroethane, 0.052 ml (0.3 mmol) of N,N-diisopropylethylamine was added, and the mixture was cooled to 0° C. The two solutions were combined in the multititer plate and first subjected to agitation at 0° C. for 1 h. Subsequently, the mixture was allowed to warm up to RT and agitated at RT overnight. Thereafter, the solvent was removed completely by means of a centrifugal dryer. The residue was dissolved in 0.6 ml of DMF and filtered, and the filtrate was separated into its components by preparative LC-MS by one of the following methods:

MS instrument: Waters, HPLC instrument: Waters; column: Waters X-Bridge C18, 19 mm×50 mm, 5 µm; mobile phase A: water+0.05% ammonia, mobile phase B: acetonitrile, with gradient; flow rate: 40 ml/min; UV detection: DAD, 210-400 nm or MS instrument: Waters, HPLC instrument: Waters; column: Phenomenex Luna 5µ C18(2) 100 A, AXIA Tech., 50 mm×21.2 mm; mobile phase A: water+0.05% formic acid, mobile phase B: acetonitrile+0.05% formic acid, with gradient; flow rate: 40 ml/min; UV detection: DAD, 210-400 nm.

In this way, 18.9 mg (36% of theory, 100% purity) of the title compound were obtained.

LC-MS (Method 6, ESIpos): $R_t$=0.84 min; m/z=530 (M+H)$^+$.

In a parallel synthetic manner analogous to Example 29, the following compounds were prepared starting from 2-(4-bromophenyl)-3-(hexahydropyrrolo[3,4-c]pyrrol-2(1H)-yl-methyl)imidazo[1,2-a]pyridine and the appropriate carbamoyl chloride or chloroformate:

| Example | IUPAC name / structure (yield; purity) | LC-MS (Method 6) |
|---|---|---|
| 30 | 5-{[2-(4-Bromophenyl)imidazo[1,2-a]pyridin-3-yl]methyl}hexahydropyrrolo[3,4-c]pyrrol-2(1H)-yl](3,4-dihydroquinoline-2(1H)-yl)methanone<br>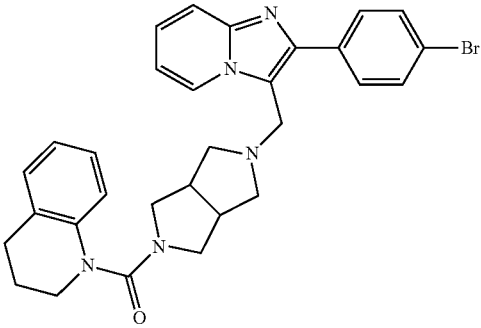<br>(52% of theory; purity 97%) | $R_t$ = 0.88 min; m/z = 556 (M + H)$^+$ |
| 31 | 5-{[2-(4-Bromophenyl)imidazo[1,2-a]pyridin-3-yl]methyl}hexahydropyrrolo[3,4-c]pyrrol-2(1H)-yl](3,4-dihydroisoquinoline-2(1H)-yl)methanone<br>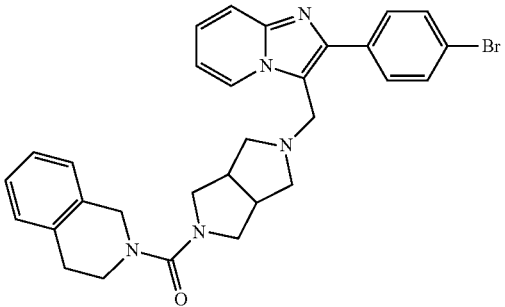<br>(18% of theory; purity 96%) | $R_t$ = 0.87 min; m/z = 556 (M + H)$^+$ |
| 32 | Isobutyl 5-{[2-(4-bromophenyl)imidazo[1,2-a]pyridin-3-yl]methyl}hexahydropyrrolo[3,4-c]pyrrole-2(1H)-carboxylate<br>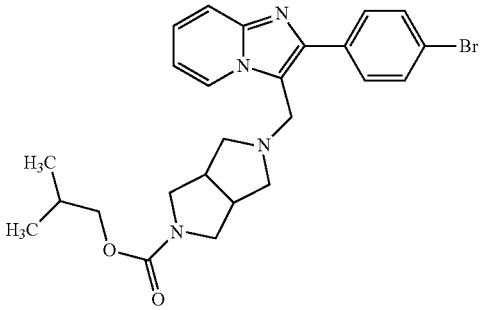<br>(11% of theory; purity 96%) | $R_t$ = 0.88 min; m/z = 497 (M + H)$^+$ |

| Example | IUPAC name / structure (yield; purity) | LC-MS (Method 6) |
| --- | --- | --- |
| 33 | Benzyl 5-{[2-(4-bromophenyl)imidazo[1,2-a]pyridin-3-yl]methyl}hexahydropyrrolo[3,4-c]pyrrole-2(1H)-carboxylate<br>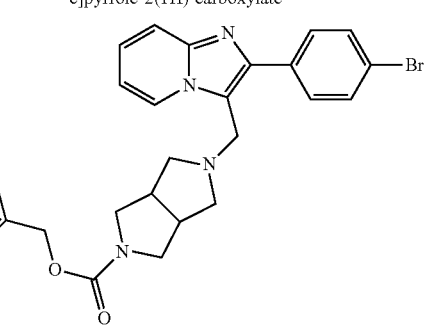<br>(39% of theory; purity 100%) | $R_t$ = 0.90 min; m/z = 531 (M + H)$^+$ |
| 34 | Cyclopentyl 5-{[2-(4-bromophenyl)imidazo[1,2-a]pyridin-3-yl]methyl}hexahydropyrrolo[3,4-c]pyrrole-2(1H)-carboxylate<br>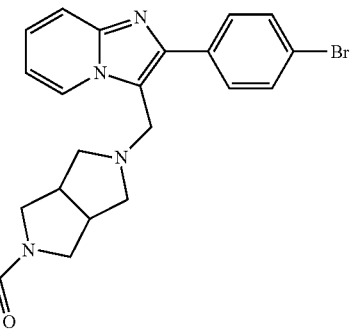<br>(46% of theory; purity 97%) | $R_t$ = 0.88 min; m/z = 509 (M + H)$^+$ |
| 35 | Isopropyl 5-{[2-(4-bromophenyl)imidazo[1,2-a]pyridin-3-yl]methyl}hexahydropyrrolo[3,4-c]pyrrole-2(1H)-carboxylate<br>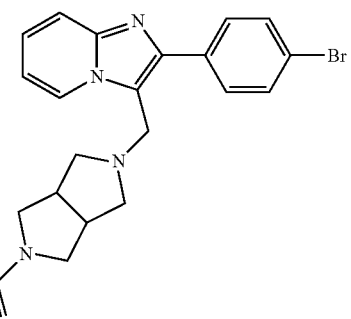<br>(24% of theory; purity 96%) | $R_t$ = 0.83 min; m/z = 483 (M + H)$^+$ |

| Example | IUPAC name / structure (yield; purity) | LC-MS (Method 6) |
|---|---|---|
| 36 | 3-(Trifluoromethyl)phenyl 5-{[2-(4-bromophenyl)imidazo[1,2-a]pyridin-3-yl]methyl}hexahydropyrrolo[3,4-c]pyrrole-2(1H)-carboxylate<br>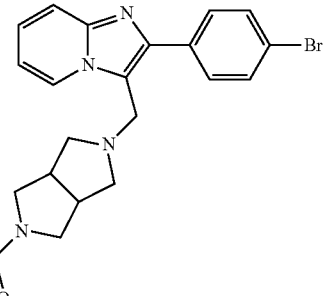<br>(10% of theory; purity 95%) | $R_t$ = 0.99 min; m/z = 585 (M + H)$^+$ |
| 37 | Fluoroethyl 5-{[2-(4-bromophenyl)imidazo[1,2-a]pyridin-3-yl]methyl}hexahydropyrrolo[3,4-c]pyrrole-2(1H)-carboxylate<br>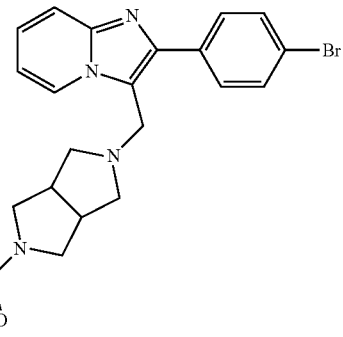<br>(10% of theory; purity 98%) | $R_t$ = 0.78 min; m/z = 487 (M + H)$^+$ |

Example 38

5-{[2-(4-Bromophenyl)imidazo[1,2-a]pyridin-3-yl]methyl}-N-(2,4-difluorophenyl)hexahydropyrrolo[3,4-c]pyrrole-2(1H)-carboxamide

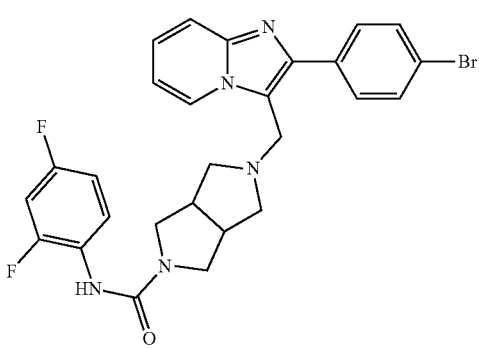 [SMILES: O=C(Nc1ccc(F)cc1F)N1CC2CN(Cc3c(-c4ccc(Br)cc4)nc4ccccn34)CC2C1]

To an initial charge of 15.5 mg (0.10 mmol) of 2,4-difluoro-1-isocyanatobenzene in a well of a 96-well multititer plate was added a solution of 39.7 mg (0.10 mmol) of 2-(4-bromophenyl)-3-(hexahydropyrrolo[3,4-c]pyrrol-2(1H)-ylmethyl)imidazo[1,2-a]pyridine in 0.8 ml of 1,2-dichloroethane. A few molecular sieves (4 Å) were added and the plate then sealed and agitated overnight at room temperature. Subsequently, the solvent was removed completely by means of a centrifugal dryer. The residue was dissolved in 0.6 ml of DMF and filtered, and the filtrate was separated into its components by preparative LC-MS by one of the following methods:

MS instrument: Waters, HPLC instrument: Waters; column: Waters X-Bridge C18, 19 mm×50 mm, 5 μm; mobile phase A: water+0.05% ammonia, mobile phase B: acetonitrile, with gradient; flow rate: 40 ml/min; UV detection: DAD, 210-400 nm or MS instrument: Waters, HPLC instrument: Waters; column: Phenomenex Luna 5μ C18(2) 100 A, AXIA Tech., 50 mm×21.2 mm; mobile phase A: water+0.05% formic acid, mobile phase B: acetonitrile+0.05% formic acid, with gradient; flow rate: 40 ml/min; UV detection: DAD, 210-400 nm.

In this way, 7.0 mg (12% of theory, 97% purity) of the title compound were obtained.

LC-MS (Method 6, ESIpos): $R_t$=0.80 min; m/z=552 (M+H)+.

In a parallel synthetic manner analogous to Example 38, the following compounds were prepared starting from 2-(4-bromophenyl)-3-(hexahydropyrrolo[3,4-c]pyrrol-2(1H)-yl-methyl)imidazo[1,2-a]pyridine and the appropriate isocyanate:

| Example | IUPAC name / structure (yield; purity) | LC-MS (Method 6) |
|---|---|---|
| 39 | 5-{[2-(4-Bromophenyl)imidazo[1,2-a]pyridin-3-yl]methyl}-N-(2,6-difluorobenzyl)hexahydropyrrolo[3,4-c]pyrrole-2(1H)-carboxamide<br>(17% of theory; purity 98%) | $R_t$ = 0.81 min; m/z = 566 (M + H)$^+$ |
| 40 | 5-{[2-(4-Bromophenyl)imidazo[1,2-a]pyridin-3-yl]methyl}-N-(2,6-dimethylphenyl)hexahydropyrrolo[3,4-c]pyrrole-2(1H)-carboxamide<br>(9% of theory; purity 92%) | $R_t$ = 0.81 min; m/z = 544 (M + H)$^+$ |
| 41 | 5-{[2-(4-Bromophenyl)imidazo[1,2-a]pyridin-3-yl]methyl}-N-[2-fluorophenyl]hexahydropyrrolo[3,4-c]pyrrole-2(1H)-carboxamide<br>(22% of theory; purity 99%) | $R_t$ = 0.80 min; m/z = 534 (M + H)$^+$ |

| Example | IUPAC name / structure (yield; purity) | LC-MS (Method 6) |
|---|---|---|
| 39 | 5-{[2-(4-Bromophenyl)imidazo[1,2-a]pyridin-3-yl]methyl}-N-(2,6-difluorobenzyl)hexahydropyrrolo[3,4-c]pyrrole-2(1H)-carboxamide 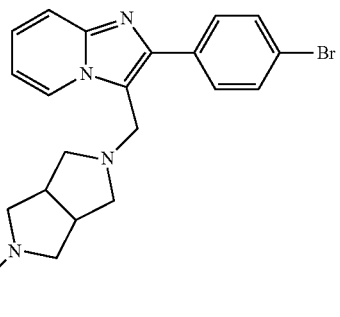 (17% of theory; purity 98%) | $R_t$ = 0.81 min; m/z = 566 (M + H)$^+$ |
| 42 | 5-{[2-(4-Bromophenyl)imidazo[1,2-a]pyridin-3-yl]methyl}-N-[2-ethoxyphenyl]hexahydropyrrolo[3,4-c]pyrrole-2(1H)-carboxamide 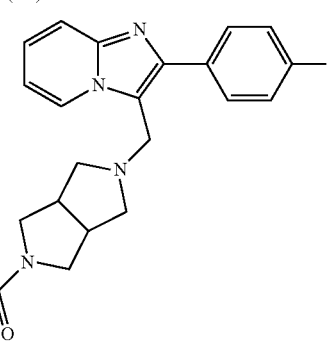 (29% of theory; purity 95%) | $R_t$ = 0.87 min; m/z = 558 (M + H)$^+$ |
| 43 | 5-{[2-(4-Bromophenyl)imidazo[1,2-a]pyridin-3-yl]methyl}-N-[4-chloro-3-(trifluoromethyl)phenyl]hexahydropyrrolo[3,4-c]pyrrole-2(1H)-carboxamide 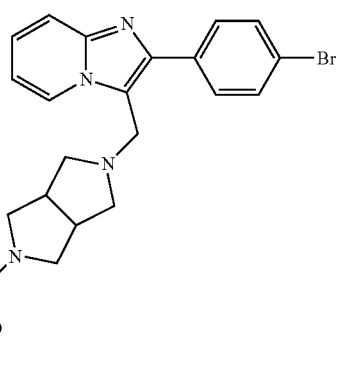 (14% of theory; purity 96%) | $R_t$ = 0.94 min; m/z = 618 (M + H)$^+$ |

| Example | IUPAC name / structure (yield; purity) | LC-MS (Method 6) |
|---|---|---|
| 39 | 5-{[2-(4-Bromophenyl)imidazo[1,2-a]pyridin-3-yl]methyl}-N-(2,6-difluorobenzyl)hexahydropyrrolo[3,4-c]pyrrole-2(1H)-carboxamide<br />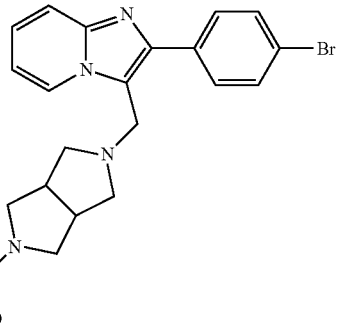<br />(17% of theory; purity 98%) | $R_t$ = 0.81 min; m/z = 566 (M + H)$^+$ |
| 44 | 5-{[2-(4-Bromophenyl)imidazo[1,2-a]pyridin-3-yl]methyl}-N-[2-chloro-5-(trifluoromethyl)phenyl]hexahydropyrrolo[3,4-c]pyrrole-2(1H)-carboxamide<br />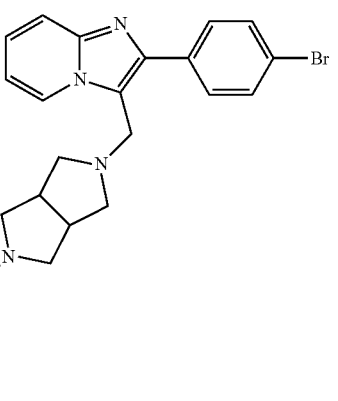<br />(26% of theory; purity 99%) | $R_t$ = 0.97 min; m/z = 618 (M + H)$^+$ |
| 45 | 5-{[2-(4-Bromophenyl)imidazo[1,2-a]pyridin-3-yl]methyl}-N-(cyclohexyl)hexahydropyrrolo[3,4-c]pyrrole-2(1H)-carboxamide<br />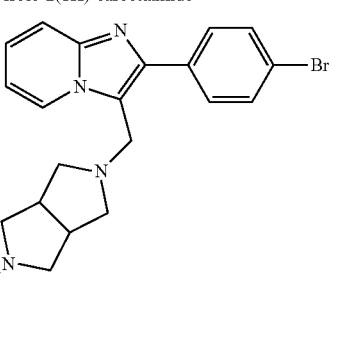<br />(29% of theory; purity 100%) | $R_t$ = 0.82 min; m/z = 522 (M + H)$^+$ |

-continued

| Example | IUPAC name / structure (yield; purity) | LC-MS (Method 6) |
|---|---|---|
| 39 | 5-{[2-(4-Bromophenyl)imidazo[1,2-a]pyridin-3-yl]methyl}-N-(2,6-difluorobenzyl)hexahydropyrrolo[3,4-c]pyrrole-2(1H)-carboxamide<br>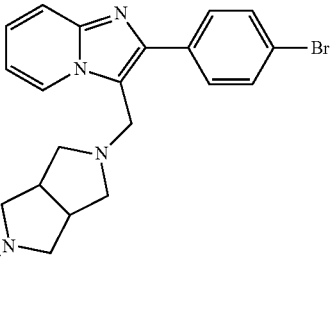<br>(17% of theory; purity 98%) | $R_t$ = 0.81 min; m/z = 566 (M + H)$^+$ |
| 46 | rac-5-{[2-(4-Bromophenyl)imidazo[1,2-a]pyridin-3-yl]methyl}-N-(1-phenylethyl)hexahydropyrrolo[3,4-c]pyrrole-2(1H)-carboxamide<br>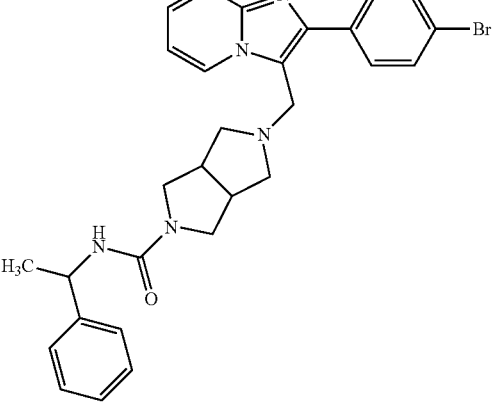<br>(33% of theory; purity 100%) | $R_t$ = 0.84 min; m/z = 544 (M + H)$^+$ |
| 47 | 5-{[2-(4-Bromophenyl)imidazo[1,2-a]pyridin-3-yl]methyl}-N-(4-fluorophenyl)hexahydropyrrolo[3,4-c]pyrrole-2(1H)-carboxamide<br>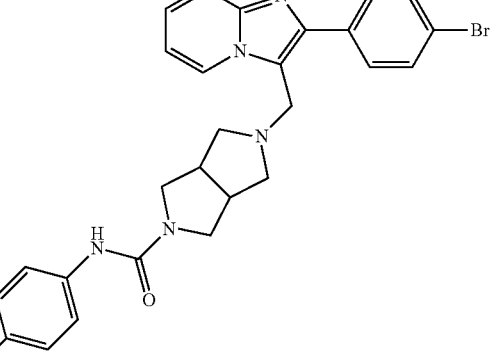<br>(7% of theory; purity 97%) | $R_t$ = 0.81 min; m/z = 534 (M + H)$^+$ |

| Example | Name / Structure / Starting materials | Analytical data |
|---|---|---|
| 48 | (3-Fluoro-6-methoxypyridin-2-yl)[5-{[2-(4-isopropylphenyl)imidazo[1,2-a]pyridin-3-yl]methyl}hexahydropyrrolo[3,4-c]pyrrol-2(1H)-yl]methanone<br>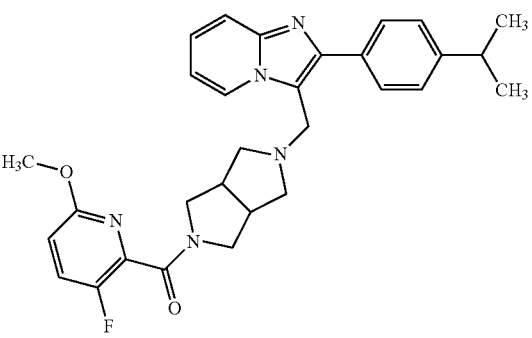<br>from 3-(hexahydropyrrolo[3,4-c]pyrrol-2(1H)-ylmethyl)-2-(4-isopropylphenyl)imidazo[1,2-a]pyridine dihydrochloride and 3-fluoro-6-methoxypyridine-2-carboxylic acid (according to Synthesis method 1) | $^1$H-NMR (400 MHz, DMSO-$d_6$): δ [ppm] = 1.24 (d, 6H), 2.34-2.64 (m, 4H, partially obscured by DMSO signal), 2.72-2.88 (m, 2H), 2.93 (dt, 1H), 3.15 (dd, 1H), 3.38 (dd, 1H), 3.50 (dd, 1H), 3.66-3.77 (m, 1H), 3.74 (s, 3H), 4.01-4.13 (m, 2H), 6.89 (td, 1H), 6.94 (dd, 1H), 7.26 (dd, 1H), 7.33 (d, 2H), 7.57 (d, 1H), 7.71-7.81 (m, 3H), 8.57 (d, 1H).<br>LC-MS (Method 2):<br>$R_t$ = 1.40 min; m/z = 514 (M + H)$^+$. |
| 49 | [5-{[2-(4-Chlorophenyl)imidazo[1,2-a]pyridin-3-yl]methyl}hexahydropyrrolo[3,4-c]pyrrol-2(1H)-yl](6-methoxy-3-methylpyridin-2-yl)methanone<br>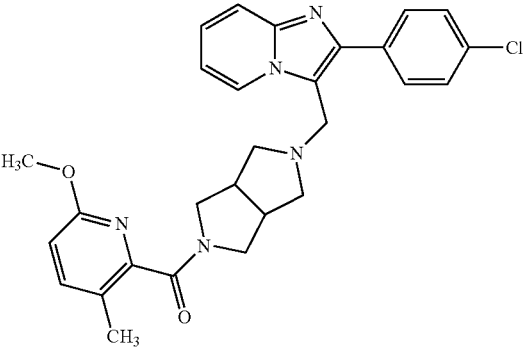<br>from 2-(4-chlorophenyl)-3-(hexahydropyrrolo[3,4-c]pyrrol-2(1H)-ylmethyl)imidazo[1,2-a]pyridine dihydrochloride and 6-methoxy-3-methylpyridine-2-carboxylic acid (according to Synthesis method 1) | $^1$H-NMR (400 MHz, DMSO-$d_6$): δ [ppm] = 1.59-1.81 (m, 4H), 2.17 (S, 3H), 2.39-2.46 (m, 2H), 2.46-2.56 (m, 1H, obscured by DMSO signal), 2.73 (br. d, 1H), 3.69 (br. s, 1H), 3.74 (s, 3H), 3.98-4.09 (m, 2H), 4.61 (br. s, 1H), 6.78 (d, 1H), 6.99 (t, 1H), 7.31 (t, 1H), 7.54 (d, 2H), 7.60 (dd, 2H), 7.92 (d, 2H), 8.60 (d, 1H).<br>LC-MS (Method 2):<br>$R_t$ = 1.52 min; m/z = 502/504 (M + H)$^+$. |

| Example | Name / Structure / Starting materials | Analytical data |
|---|---|---|
| 50 | [5-{[2-(4-Chlorophenyl)imidazo[1,2-a]pyridin-3-yl]methyl}hexahydropyrrolo[3,4-c]pyrrol-2(1H)-yl](3-fluoro-6-methoxypyridin-2-yl)methanone<br>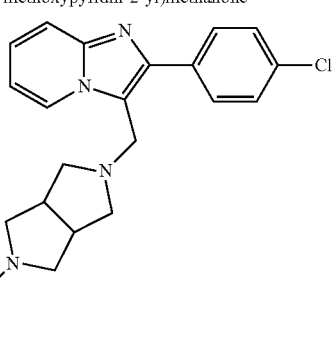<br>from 2-(4-chlorophenyl)-3-(hexahydropyrrolo[3,4-c]pyrrol-2(1H)-ylmethyl)imidazo[1,2-a]pyridine dihydrochloride and 3-fluoro-6-methoxypyridine-2-carboxylic acid (according to Synthesis method 1) | $^1$H-NMR (400 MHz, DMSO-$d_6$): δ [ppm] = 2.40-2.63 (m, 4H, partially obscured by DMSO signal), 2.71-2.88 (m, 2H), 3.15 (dd, 1H), 3.39 (dd, 1H), 3.49 (dd, 1H), 3.66-3.75 (m, 4H), 4.01-4.12 (m, 2H), 6.88-6.98 (m, 2H), 7.29 (dd, 1H), 7.51 (d, 2H), 7.59 (d, 1H), 7.76 (t, 1H), 7.90 (d, 2H), 8.60 (d, 1H).<br>LC-MS (Method 2):<br>$R_t$ = 1.37 min; m/z = 506/508 (M + H)$^+$. |
| 51 | (3-Chloro-6-methoxypyridin-2-yl)[5-{[2-(4-chlorophenyl)imidazo[1,2-a]pyridin-3-yl]methyl}hexahydropyrrolo[3,4-c]pyrrol-2(1H)-yl]methanone<br>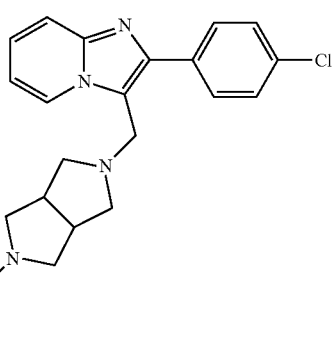<br>from 2-(4-chlorophenyl)-3-(hexahydropyrrolo[3,4-c]pyrrol-2(1H)-ylmethyl)imidazo[1,2-a]pyridine dihydrochloride and 3-chloro-6-methoxypyridine-2-carboxylic acid (according to Synthesis method 1) | $^1$H-NMR (400 MHz, DMSO-$d_6$): δ [ppm] = 2.35-2.43 (m, 1H), 2.44-2.64 (m, 3H, partially obscured by DMSO signal), 2.70-2.80 (m, 1H), 2.80-2.90 (m, 1H), 2.95 (dd, 1H), 3.28-3.42 (m, 2H, partially obscured by H$_2$O signal), 3.70 (dd, 1H), 3.74 (s, 3H), 4.08 (s, 2H), 6.87-6.98 (m, 2H), 7.30 (t, 1H), 7.51 (d, 2H), 7.59 (d, 1H), 7.85 (d, 1H), 7.90 (d, 2H), 8.60 (d, 1H).<br>LC-MS (Method 2):<br>$R_t$ = 1.44 min; m/z = 522/523/524 (M + H)$^+$. |

B. ASSESSMENT OF PHARMACOLOGICAL EFFICACY

The pharmacological activity of the compounds of the invention can be demonstrated by in vitro and in vivo studies as known to the person skilled in the art. The application examples which follow describe the biological action of the compounds of the invention, without restricting the invention to these examples.

B-1. In Vitro Electrophysiological Analysis of the Human TASK-1 and TASK-3 Channels Via Two-Electrode Voltage Clamp Technique in *Xenopus laevis* Oocytes

*Xenopus laevis* oocytes were selected as described elsewhere by way of illustration [Decher et al., *FEBS Lett.* 492, 84-89 (2001)]. Subsequently, the oocytes were injected with 0.5-5 ng of a cRNA solution coding for TASK-1 or TASK-3. For the electrophysiological analysis of the channel proteins expressed in the oocytes, the two-electrode voltage clamp technique [Stühmer, *Methods Enzymol.* 207, 319-339 (1992)] was used. The measurements were conducted as described [Decher et al., *FEBS Lett.* 492, 84-89 (2001)] at room temperature (21-22° C.) using a Turbo TEC 10CD amplifier (NPI), recorded at 2 kHz and filtered with 0.4 kHz. Substance administration was performed using a gravitation-driven perfusion system. Here, the oocyte is located in a measuring chamber and exposed to the solution stream of 10 ml/min. The level in the measuring chamber is monitored and regulated by sucking off the solution using a peristaltic pump.

Table 1A below shows the half-maximum inhibition, determined in this test, of human TASK-1 and TASK-3 channels (IC$_{50}$) by representative working examples of the invention:

TABLE 1A

| Example No. | TASK-1 IC$_{50}$ [nM] | TASK-3 IC$_{50}$ [nM] |
|---|---|---|
| 4 | 59.9 ± 16.2 | 256 ± 48.8 |
| 10 | 31.2 ± 1.7 | 970 ± 220 |
| 17 | 9.3 ± 2.5 | 21.8 ± 2.2 |
| 25 | 62.2 ± 7.9 | 44.1 ± 5.8 |

From the data in Table 1A it is evident that both TASK-1 and TASK-3 are blocked. Accordingly, the results in Table 1A confirm the mechanism of action of the compounds according to the invention as TASK-1/3 inhibitors.

For comparison, a further (2-phenylimidazo[1,2-a]pyridin-3-yl)methyl-substituted perhydropyrrolo[3,4-c]pyrrole derivative, which can be considered to be the structurally closest prior art [see the compounds described in WO 2014/187922-A1 as inhibitors of glucose transporters (GLUT)], was also assessed in this test with regard to inhibition of human TASK-1 and TASK-3 channels. The result obtained for this compound is shown in Table 1B below:

TABLE 1B

| Structure of the comparative compound | TASK-1 | | | TASK-3 | | |
|---|---|---|---|---|---|---|
| | % inhibition at | | IC$_{50}$ | % inhibition at | | IC$_{50}$ |
| | 1 µM | 10 µM | [µM] | 1 µM | 10 µM | [µM] |
| (Example 160 in WO 2014/187922) | 11.4 ± 1.5 | 37.2 ± 7.5 | >10 | 5.6 ± 1.3 | 8.9 ± 0.9 | inactive |

Thus, the comparative compound of the prior art shown in Table 1B has, according to this test, an inhibitory activity lower by around 1 to 3 orders of magnitude with regard to TASK-1 channels and no notable inhibition of TASK-3 channels.

B-2. Inhibition of Recombinant TASK-1 and TASK-3 In Vitro

The investigations on the inhibition of the recombinant TASK-1 and TASK-3 channels were conducted using stably transfected CHO cells. The compounds according to the invention were tested in this case by application of 40 mM potassium chloride in the presence of a voltage-sensitive dye according to the methods described in detail in the following references [Whiteaker et al., Validation of FLIPR membrane potential dye for high-throughput screening of potassium channel modulators, *J. Biomol. Screen.* 6 (5), 305-312 (2001); Molecular Devices FLIPR *Application Note*: Measuring membrane potential using the FLIPR® membrane potential assay kit on Fluorometric Imaging Plate Reader (FLIPR®) systems, http://www.moleculardevices.com/reagents-supplies/assay-kits/ion-channels/flipr-membrane-potential-assay-kits]. The activity of the test substances was determined as their ability to inhibit a depolarization induced in the recombinant cells by 40 mM potassium chloride. The concentration which can block half of this depolarization is referred to as IC$_{50}$.

Table 2A below lists the IC$_{50}$ values from this assay determined for the working examples of the invention (some as mean values from multiple independent individual determinations):

TABLE 2A

| Example No. | TASK-1 IC$_{50}$ [nM] | TASK-3 IC$_{50}$ [nM] |
|---|---|---|
| 1 | 2410 | 6100 |
| 2 | 1730 | 5400 |
| 3 | 2500 | 7400 |
| 4 | 947 | 2300 |
| 5 | 1130 | 1600 |
| 6 | 683 | 1300 |
| 7 | 787 | 4300 |
| 8 | 1360 | 810 |

TABLE 2A-continued

| Example No. | TASK-1 IC$_{50}$ [nM] | TASK-3 IC$_{50}$ [nM] |
|---|---|---|
| 9 | 749 | 660 |
| 10 | 206 | 485 |
| 11 | 1210 | 2500 |
| 12 | 1200 | 960 |
| 13 | 712 | 1300 |
| 14 | 1060 | 3400 |
| 15 | 1000 | 2900 |
| 16 | 1940 | 1100 |
| 17 | 721 | 1900 |
| 18 | 1680 | 4900 |
| 19 | 1250 | 1500 |
| 20 | 1020 | 2500 |
| 21 | 1250 | 230 |
| 22 | 1460 | 320 |
| 23 | 728 | 100 |
| 24 | 330 | 800 |
| 25 | 230 | 410 |
| 26 | 220 | 310 |
| 27 | 170 | 170 |

TABLE 2A-continued

| Example No. | TASK-1 IC$_{50}$ [nM] | TASK-3 IC$_{50}$ [nM] |
|---|---|---|
| 28 | 300 | 190 |
| 29 | 920 | 2100 |
| 30 | 480 | 1200 |
| 32 | 1100 | 1200 |
| 33 | 460 | 4400 |
| 34 | 500 | 3300 |
| 35 | 700 | 1700 |
| 36 | 180 | 450 |
| 37 | 600 | 1800 |
| 38 | 1500 | 1900 |
| 41 | 580 | 2900 |
| 42 | 740 | 3700 |
| 43 | 1700 | 2000 |
| 44 | 700 | 2000 |
| 45 | 2300 | 5800 |
| 46 | 460 | 2200 |
| 47 | 1000 | 240 |
| 48 | 78 | 79 |
| 49 | 94 | 4.6 |
| 50 | 1100 | 110 |
| 51 | 1400 | 80 |

From the data in Table 2A it is evident that both TASK-1 and TASK-3 are blocked. Accordingly, the results in Table 2A confirm the mechanism of action of the compounds according to the invention as TASK-1/3 inhibitors.

For comparison, a further (2-phenylimidazo[1,2-a]pyridin-3-yl)methyl-substituted perhydropyrrolo[3,4-c]pyrrole derivative, which can be considered to be the structurally closest prior art [see the compounds described in WO 2014/187922-A1 as inhibitors of glucose transporters (GLUT)], was also assessed in this test with regard to inhibition of recombinant TASK-1 and TASK-3 channels. The result obtained for this compound is shown in Table 2B below:

TABLE 2B

| Structure of the comparative compound | Example No. in WO 2014/187922 | TASK-1 IC$_{50}$ [nM] | TASK-3 IC$_{50}$ [nM] |
|---|---|---|---|
| [structure] | 160 | 15000 | 2400 |

Thus, the comparative compound of the prior art shown in Table 2B has, according to this test, a considerably weaker inhibitory activity, which can be considered to be non-specific, with regard to TASK-1.

B-3. Animal Model of Obstructive Sleep Apnea in the Pig

Using negative pressure, it is possible to induce collapse and thus obstruction of the upper respiratory tract in anesthetized, spontaneously breathing pigs [Wirth et al., Sleep 36, 699-708 (2013)].

German Landrace pigs are used for the model. The pigs are anesthetized and tracheotomized. One cannula each is inserted into the rostral and the caudal part of the trachea. Using a T connector, the rostral cannula is connected on the one hand to a device generating negative pressures and on the other hand to the caudal cannula. Using a T connector, the caudal cannula is connected to the rostral cannula and to a tube which allows spontaneous breathing circumventing the upper respiratory tract. By appropriate closing and opening of the tubes it is thus possible for the pig to change from normal nasal breathing to breathing via the caudal cannula during the time when the upper respiratory tract is isolated and connected to the device for generating negative pressures. The muscle activity of the *musculus genioglossus* is recorded by electromyogram (EMG).

At certain points in time, the collapsibility of the upper respiratory tract is tested by having the pig breathe via the caudal cannula and applying negative pressures of −50, −100 and −150 cm water head (cmH$_2$O) to the upper respiratory tract. This causes the upper respiratory tract to collapse, which manifests itself in an interruption of the airflow and a pressure drop in the tube system. This test is conducted prior to the administration of the test substance and at certain intervals after the administration of the test substance. An appropriately effective test substance can prevent this collapse of the respiratory tract in the inspiratory phase.

After changeover from nasal breathing to breathing via the caudal cannula, it is not possible to measure any EMG activity of the *musculus genioglossus* in the anesthetized pig. As a further test, the negative pressure at which EMG activity restarts is then determined. This threshold value is, if a test substance is effective, shifted to more positive values. The test is likewise conducted prior to the administration of the test substance and at certain intervals after the administration of the test substance. Administration of the test substance can be intranasal, intravenous, subcutaneous, intraperitoneal or intragastral.

C. WORKING EXAMPLES OF PHARMACEUTICAL COMPOSITIONS

The compounds of the invention can be converted to pharmaceutical preparations as follows:

Tablet:

Composition:

100 mg of the compound of the invention, 50 mg of lactose (monohydrate), 50 mg of corn starch (native), 10 mg of polyvinylpyrrolidone (PVP 25) (BASF, Ludwigshafen, Germany) and 2 mg of magnesium stearate.

Tablet weight 212 mg. Diameter 8 mm, radius of curvature 12 mm.

Production:

The mixture of compound of the invention, lactose and starch is granulated with a 5% solution (w/w) of the PVP in water. The granules are dried and then mixed with the magnesium stearate for 5 minutes. This mixture is compressed using a conventional tableting press (see above for format of the tablet). The guide value used for the pressing is a pressing force of 15 kN.

Suspension for Oral Administration:

Composition:

1000 mg of the compound of the invention, 1000 mg of ethanol (96%), 400 mg of Rhodigel® (xanthan gum from FMC, Pa., USA) and 99 g of water.

10 ml of oral suspension correspond to a single dose of 100 mg of the compound of the invention.

Production:

The Rhodigel is suspended in ethanol; the compound of the invention is added to the suspension. The water is added while stirring. The mixture is stirred for about 6 h until the swelling of the Rhodigel is complete.

Solution for Oral Administration:

Composition:

500 mg of the compound of the invention, 2.5 g of polysorbate and 97 g of polyethylene glycol 400. 20 g of oral solution correspond to a single dose of 100 mg of the compound of the invention.

Production:

The compound of the invention is suspended in the mixture of polyethylene glycol and polysorbate with stirring. The stirring operation is continued until dissolution of the compound of the invention is complete.

i.v. Solution:

The compound of the invention is dissolved in a concentration below the saturation solubility in a physiologically acceptable solvent (e.g. isotonic saline solution, glucose solution 5% and/or PEG 400 solution 30%). The solution is subjected to sterile filtration and dispensed into sterile and pyrogen-free injection vessels.

Solution for Nasal Administration:

The compound of the invention is dissolved in a concentration below the saturation solubility in a physiologically acceptable solvent (e.g. purified water, phosphate buffer, citrate buffer). The solution may contain further additives for isotonization, for preservation, for adjusting the pH, for improvement in the solubility and/or for stabilization.

The invention claimed is:

1. A compound of the formula (I)

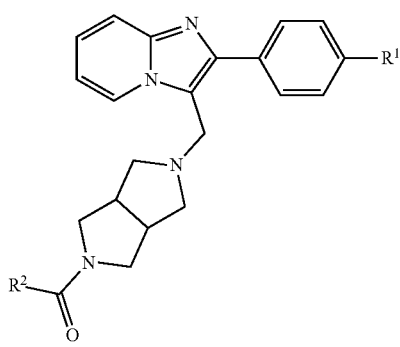

(I)

wherein $R^1$ is halogen, cyano or $(C_1$-$C_4)$-alkyl, and $R^2$ is $(C_4$-$C_6)$-cycloalkyl wherein a ring $CH_2$ group may be replaced by —O—, or $R^2$ is a phenyl group of the formula (a) or a pyridyl group of the formula (b)

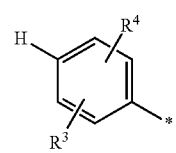

(a)

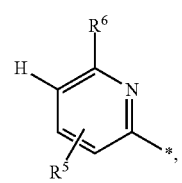

(b)

wherein * marks the bond to the adjacent carbonyl group, and $R^3$ is hydrogen, fluorine, chlorine, bromine, cyano, $(C_1$-$C_3)$-alkyl or $(C_1$-$C_3)$-alkoxy, wherein $(C_1$-$C_3)$-alkyl and $(C_1$-$C_3)$-alkoxy may be up to trisubstituted by fluorine, $R^4$ is hydrogen, fluorine, chlorine, bromine or methyl, $R^5$ is hydrogen, fluorine, chlorine, bromine or methyl, and $R^6$ is hydrogen or $(C_1$-$C_3)$-alkoxy which may be up to trisubstituted by fluorine, or $R^2$ is an —$OR^7$ or —$NR^8R^9$ group wherein $R^7$ and $R^8$ in each case are $(C_1$-$C_4)$-alkyl, $(C_4$-$C_6)$-cycloalkyl, phenyl, benzyl, 1-phenylethyl or 2-phenylethyl, wherein $(C_1$-$C_4)$-alkyl may be up to trisubstituted by fluorine, and wherein phenyl and the phenyl groups in benzyl, 1-phenylethyl and 2-phenylethyl may be up to disubstituted by identical or different radicals selected from the group consisting of fluorine, chlorine, methyl, ethyl, trifluoromethyl, methoxy and ethoxy, and $R^9$ is hydrogen or methyl, or $R^8$ and $R^9$ are attached to one another and, together with the nitrogen atom to which they are bonded, form a tetrahydroquinoline ring of the formula (c) or a tetrahydroisoquinoline ring of the formula (d),

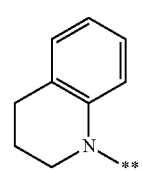

(c)

(d)

wherein ** marks the bond to the carbonyl group,
or a salt, a solvate, or a solvate of a salt thereof.

2. The compound of claim 1, wherein
$R^1$ is chlorine, bromine or isopropyl,
and
$R^2$ is cyclobutyl, cyclopentyl or cyclohexyl,
or
$R^2$ is a phenyl group of the formula (a) or a pyridyl group of the formula (b)

(a)

(b)

wherein * marks the bond to the adjacent carbonyl group, and
$R^3$ is fluorine, chlorine, methyl, trifluoromethyl, methoxy or trifluoromethoxy,
$R^4$ is hydrogen or fluorine,
$R^5$ is hydrogen, fluorine, chlorine or methyl,
and
$R^6$ is methoxy, difluoromethoxy, trifluoromethoxy or isopropoxy,
or
$R^2$ is an —$OR^7$ or —$NR^8R^9$ group wherein
$R^7$ is isopropyl, isobutyl, tert-butyl, cyclopentyl, phenyl or benzyl,
wherein phenyl and the phenyl group in benzyl may be up to disubstituted by identical or different radicals selected from the group consisting of fluorine, chlorine, methyl, trifluoromethyl, methoxy and ethoxy,
$R^8$ is phenyl, benzyl or 1-phenylethyl,
wherein phenyl and the phenyl groups in benzyl and 1-phenylethyl may be up to disubstituted by identical or different radicals selected from the group consisting of fluorine, chlorine, methyl, trifluoromethyl, methoxy and ethoxy,
and
$R^9$ is hydrogen or methyl,
or
$R^8$ and $R^9$ are attached to one another and, together with the nitrogen atom to which they are bonded, form a tetrahydroquinoline ring of the formula (c), (c)

wherein ** marks the bond to the carbonyl group,
or a salt, a solvate, or a solvate of a salt thereof.

3. The compound of claim 1, wherein
$R^1$ is chlorine, bromine or isopropyl,
and
$R^2$ is cyclobutyl or cyclopentyl,
or
$R^2$ is a phenyl group of the formula (a) or a pyridyl group of the formula (b)

(a)

(b)

wherein * marks the bond to the adjacent carbonyl group, and
$R^3$ is fluorine, chlorine, methyl, trifluoromethyl or methoxy,
$R^4$ is hydrogen or fluorine,
$R^5$ is hydrogen, fluorine or methyl,
and
$R^6$ is methoxy,
or
$R^2$ is an —$OR^7$ or —$NR^8R^9$ group wherein
$R^7$ is isopropyl, cyclopentyl, phenyl or benzyl,
wherein phenyl and the phenyl group in benzyl may be up to disubstituted by identical or different radicals selected from the group consisting of fluorine, chlorine, methyl, trifluoromethyl, methoxy and ethoxy,
$R^8$ is phenyl or 1-phenylethyl,
wherein phenyl and the phenyl group in 1-phenylethyl may be up to disubstituted by identical or different radicals selected from the group consisting of fluorine, chlorine, methyl, trifluoromethyl, methoxy and ethoxy,
and
$R^9$ is hydrogen,
or
$R^8$ and $R^9$ are attached to one another and, together with the nitrogen atom to which they are bonded, form a tetrahydroquinoline ring of the formula (c),

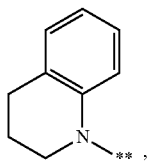

wherein ** marks the bond to the carbonyl group,
or a salt, a solvate, or a solvate of a salt thereof.

4. The compound of claim 1, wherein
R¹ is chlorine or isopropyl,
and
R² is a pyridyl group of the formula (b)

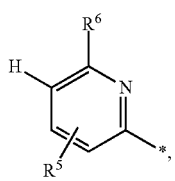

wherein * marks the bond to the adjacent carbonyl group,
$R^5$ is hydrogen, fluorine or methyl,
and
$R^6$ is methoxy,
or a salt, a solvate, or a solvate of a salt thereof.

5. A method for preparing a compound of the formula (I) as defined in claim 1, comprising:
reacting a compound of the formula (II)

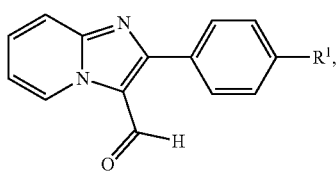

wherein R¹ is as defined in claim 1,
in the presence of a suitable reducing agent either
[A] with a compound of the formula (III)

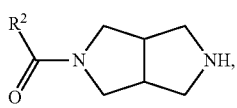

wherein R² is as defined in claim 1,
to give a compound of the formula (I);
or
[B] with a protected perhydropyrrolo[3,4-c]pyrrole of the formula (IV)

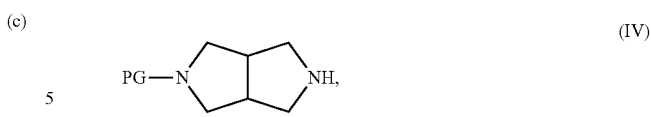

wherein PG is a suitable amino protecting group,
at first to give a compound of the formula (V)

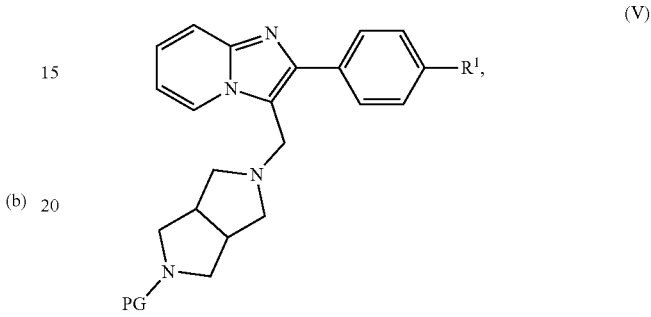

wherein PG is as defined for the compound of formula (IV) and R¹ is as defined in claim 1,
then cleaving the protecting group PG in the compound of formula (V) to give a compound of the formula (VI)

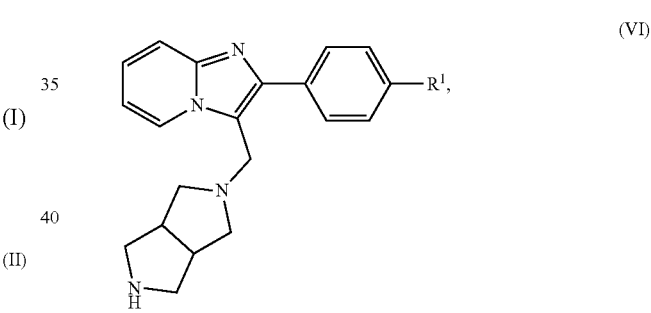

wherein R¹ is as defined in claim 1,
then reacting the compound of the formula (VI), depending on the specific definition of the R² radical,
[B-1] with a carboxylic acid of the formula (VII)

wherein
$R^{24}$ is $(C_4-C_6)$-cycloalkyl wherein a ring $CH_2$ group may be replaced by —O—, or is a phenyl group of the formula (a) or a pyridyl group of the formula (b), as described in claim 1,
with activation of the carboxylic acid function in (VII), or with the corresponding acid chloride of the formula (VIII)

(VIII)

$R^{24}$—C(=O)—Cl, wherein $R^{24}$ is as defined above,
to give a compound of the formula (I-A)

(I-A)

wherein $R^1$ is as defined in claim 1 and $R^{24}$ is as defined above,
or
[B-2] with a chloroformate or carbamoyl chloride of the formula (IX)

(IX)

$R^{2B}$—C(=O)—Cl, wherein
$R^{2B}$ is the —$OR^7$ or —$NR^8R^{9A}$ group wherein
$R^7$ and $R^8$ are as defined in claim 1,
and
$R^{9A}$ has the definition of $R^9$ as defined in claim 1, but is not hydrogen, to give a compound of the formula (I-B)

(I-B)

wherein $R^1$ is as defined in claim 1 and $R^{2B}$ is as defined above have the definitions specified above,
or
[B-3] with an isocyanate of the formula (X)

$R^8$—N=C=O   (X), wherein $R^8$ is as defined in claim 1,
to give a compound of the formula (I-C)

(I-C)

wherein $R^1$ and $R^8$ are as defined in claim 1,
and optionally converting the resulting compound of formula (I), formula (I-A), formula (I-B), or formula (I-C) with an appropriate solvent and/or acid into a salt, a solvate, or a solvate of a salt thereof.

6. A pharmaceutical composition comprising a compound of claim 1 in combination with one or more inert, nontoxic, pharmaceutically suitable excipients.

7. The pharmaceutical composition comprising a compound of claim 1 in combination with one or more further active compounds selected from the group consisting of respiratory stimulants, psychostimulating compounds, serotonin reuptake inhibitors, noradrenergic, serotonergic and tricyclic antidepressants, sGC stimulators, mineralocorticoid receptor antagonists, antiinflammatory drugs, immunomodulators, immunosuppressives and cytotoxic drugs.

8. The method of claim 5, wherein PG is tert-butoxycarbonyl, benzyloxycarbonyl or (9H-fluoren-9-ylmethoxy)carbonyl.

* * * * *